US008580926B2

(12) United States Patent
Muraca

(10) Patent No.: US 8,580,926 B2
(45) Date of Patent: Nov. 12, 2013

(54) GENE AND PROTEIN EXPRESSION PROFILES ASSOCIATED WITH THE THERAPEUTIC EFFICACY OF IRINOTECAN

(75) Inventor: Patrick J. Muraca, Pittsfield, MA (US)

(73) Assignee: Nuclea Biomarkers, LLC, Pittsfield, MA (US)

( * ) Notice: Subject to any disclaimer, the term of this patent is extended or adjusted under 35 U.S.C. 154(b) by 333 days.

(21) Appl. No.: 12/487,061

(22) Filed: Jun. 18, 2009

(65) Prior Publication Data

US 2009/0298084 A1 Dec. 3, 2009

Related U.S. Application Data

(63) Continuation of application No. 11/903,470, filed on Sep. 21, 2007, now abandoned.

(60) Provisional application No. 60/846,298, filed on Sep. 21, 2006, provisional application No. 60/906,438, filed on Mar. 12, 2007.

(51) Int. Cl.
*C07K 16/00* (2006.01)

(52) U.S. Cl.
USPC .......................................................... 530/387.1

(58) Field of Classification Search
USPC .......................................................... 435/7.1
See application file for complete search history.

(56) References Cited

U.S. PATENT DOCUMENTS

| | | | | |
|---|---|---|---|---|
| 5,569,755 | A | 10/1996 | Schweinfest et al. | |
| 5,733,748 | A | 3/1998 | Yu et al. | |
| 5,831,015 | A | 11/1998 | Schweinfest et al. | |
| 6,210,887 | B1 | 4/2001 | Schweinfest et al. | |
| 6,337,195 | B1 | 1/2002 | Yu et al. | |
| 6,455,251 | B1 | 9/2002 | Waldman | |
| 6,455,668 | B1 | 9/2002 | Mack et al. | |
| 6,468,790 | B1 | 10/2002 | Giese | |
| 6,566,502 | B1 | 5/2003 | Mack et al. | |
| 6,602,659 | B1 | 8/2003 | Waldman et al. | |
| 6,635,748 | B2 | 10/2003 | Xin et al. | |
| 6,682,890 | B2 | 1/2004 | Mack et al. | |
| 6,773,878 | B1 | 8/2004 | Mack et al. | |
| 6,794,501 | B2 | 9/2004 | Chen et al. | |
| 6,831,152 | B2 | 12/2004 | Yu et al. | |
| 6,949,339 | B1 | 9/2005 | Macina et al. | |
| 7,056,674 | B2 | 6/2006 | Baker et al. | |
| 7,081,340 | B2 | 7/2006 | Baker et al. | |
| 2004/0146921 | A1 | 7/2004 | Eveleigh et al. | |
| 2004/0157255 | A1 | 8/2004 | Agus et al. | |
| 2004/0203034 | A1 | 10/2004 | Ratain et al. | |
| 2005/0009110 | A1 * | 1/2005 | Chang | 435/7.2 |
| 2005/0227266 | A1 | 10/2005 | Ross et al. | |
| 2005/0260646 | A1 | 11/2005 | Baker et al. | |
| 2006/0094068 | A1 | 5/2006 | Bacus et al. | |
| 2006/0166230 | A1 | 7/2006 | Baker et al. | |
| 2006/0166231 | A1 | 7/2006 | Baker et al. | |
| 2006/0246433 | A1 | 11/2006 | Adorjan et al. | |
| 2007/0105142 | A1 | 5/2007 | Wilhelm | |
| 2007/0190583 | A1 | 8/2007 | Spector et al. | |
| 2007/0212738 | A1 | 9/2007 | Haley et al. | |
| 2008/0014579 | A1 | 1/2008 | Liu et al. | |

OTHER PUBLICATIONS

Mamay et al (Oncogene, 22, 602-614, 2003).*
Cross et al (Histopathology, 46:256-269, 2005).*
Minderman et al., "In vitro and in vivoirinotecan-induced changes in expression profles of cell-cycle and apoptosis-associated genes in acute meloid leukemia cells"; Mel. Cancer Ther,. (2005), 4(6):885-900.
Shah et al., "Drg1 Expression in 131 Colorectal Liver Metastases: Correlation with Clinical Variables and Patient Outcomes"; Clin. Cancer Res. (2005), 11(9):3296-3302.
Yu et al., "Gene Expression Profiling of the irinotecan Pathway in Colorectal Cancer"; Clip. Cancer Res. (2005), 11(5): 2053-2062.
Guo et ai., "Enhanced chemosensitivity to lrinotecan by RNA Interference-mediated down-regulation of the Nuclear Factor KB p65 subunit"; Clin. Cancer Res. (2004), 10(10): 3333-3341.
Fallik et al., "Microsatellite instability is a predictive factor of the tumor response to irinotecan in patients with advanced colorectal cancer"; Cancer Res. (2003), 63(18): 5738-4.
Perdu et al., "Distinctive gene expression patterns in human mammary epithelial cells and breast cancer"; PNAS USA (1999), 96:9212-17.
Cham et al., JBC, (2003) 278(19): 17044-52.
Skolnick et al., Trends in Biotechnology, (2000), 18: 34-39.

* cited by examiner

*Primary Examiner* — Brad Duffy
(74) *Attorney, Agent, or Firm* — DT Ward, PC

(57) ABSTRACT

The present invention includes gene and protein expression profiles indicative of whether a cancer patient is likely to respond to treatment with irinotecan. By identifying such responsiveness, a treatment provider may determine in advance those patients who would benefit from such treatment, as well as identify alternative therapies for non-responders. The present invention further provide methods of using the gene and/or protein expression profiles and assays for identifying the presence of a gene and/or protein expression profile in a patient sample.

13 Claims, 1 Drawing Sheet

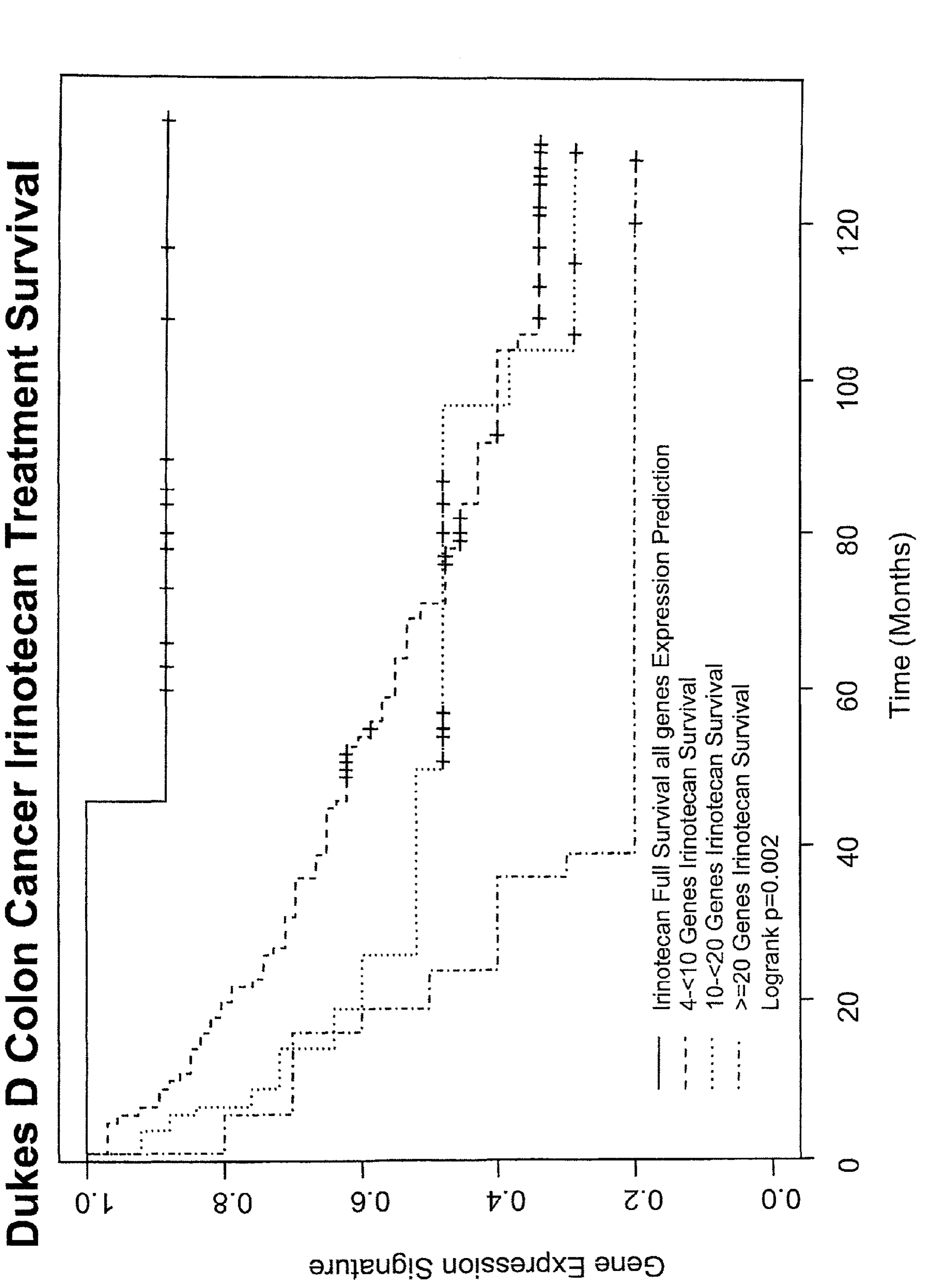
Dukes D Colon Cancer Irinotecan Treatment Survival
Gene Expression Signature
1.0
0.8
0.6
0.4
0.2
0.0
0
20
40
60
80
100
120
Time (Months)
Irinotecan Full Survival all genes Expression Prediction
4-<10 Genes Irinotecan Survival
10-<20 Genes Irinotecan Survival
>=20 Genes Irinotecan Survival
Logrank p=0.002

GENE AND PROTEIN EXPRESSION PROFILES ASSOCIATED WITH THE THERAPEUTIC EFFICACY OF IRINOTECAN

RELATED APPLICATIONS

This application is a continuation of U.S. application Ser. No. 11/903,470, filed Sep. 21, 2007, now abandoned which in turn claims the benefit under 35 U.S.C. §119(e) to U.S. provisional Application Ser. No. 60/846,298 filed Sep. 21, 2006 and Application Ser. No. 60/906,438 filed Mar. 12, 2007, the entirety of which are incorporated herein by reference.

BACKGROUND OF THE INVENTION

Patients diagnosed with cancer are faced with costly and often painful treatment options. These treatments may be ineffective in a subpopulation of patients, and as a result, these patients endure these treatments without little or no therapeutic benefit. Some patients may react adversely to certain agents causing additional suffering and possibly death.

Ineffective treatment also is problematic because time is a key variable when treating cancer. A treatment provider has a far greater chance of containing and managing the disease if the cancer is diagnosed at an early stage and treated with a therapeutically effective agent. An agent may provide great therapeutic benefits if administered at an early stage of the disease; however, with the passage of time, the same agent may cease to be effective.

Colorectal cancer is an example of a condition where early diagnosis is key for effective treatment. Colorectal cancer is cancer that develops in the colon or the rectum. The walls of the colon and rectum have several layers of tissue. Colorectal cancer often starts in the innermost layer and can grow through some or all of the other layers; the stage (extent of spread) of a colorectal cancer depends to a great degree on how deeply it has grown into these layers.

Chemotherapy is often used for treating colorectal cancer. Irinotecan hydrochloride (CAMPTOSAR®) is a chemotherapeutic agent indicated for first-line therapy of colorectal cancers. As with many chemotherapeutic agents, administration of irinotecan hydrochloride ("irinotecan") often causes deleterious side effects for the patient, and some patients do not respond well to the treatment. Some patients thus undergo treatment with irinotecan and suffer the painful side effects only to later realize that the agent has not been therapeutically beneficial to their condition. In addition to the unnecessary suffering, critical time is lost in determining an alternative treatment.

SUMMARY OF THE INVENTION

The present invention provides gene and protein expression profiles and methods of using them to identify those patients who are likely to respond to treatment with irinotecan (these patients are referred to as "responders"), as well as those patients who are not likely to benefit from such treatment (these patients are referred to as "non-responders"). The present invention allows a treatment provider to identify those patients who are responders to irinotecan treatment, and those who are not non-responders to such treatment, prior to administration of the agent.

In one aspect, the present invention comprises gene expression profiles, also referred to as "gene signatures," that are indicative of a cancer patient's tendency to respond to treatment with irinotecan. The gene expression profile (GEP)

comprises at least one, and preferably a plurality, of genes selected from the group consisting of ERBB2, GRB7, Erk1 kinase, JNK1 kinase, BCL2, phospho-GSK-3beta, MMP11, CTSL2, CCNB1, BIRC5, MK167, STK6, MRP14, phospho-Akt, CD68, BAG1 and GSTM1. The gene signature may further include reference or control genes. The currently preferred reference genes are ACTB, GAPD, GUSB, RPLP0 and TFRC. According to the invention, some or all of theses genes are differentially expressed (e.g., up-regulated or down-regulated) in patients who are responders to irinotecan therapy. Specifically, ERBB2, GRB7, JNK1 kinase, BCL2, MK167, phospho-Akt, CD68 and BAG1 are up-regulated (over-expressed) and Erk1 kinase, phospho-GSK-3beta, MMP11, CTSL2, CCNB1, BIRC5, STK6, MRP14 and GSTM1 are down-regulated (under-expressed) in patients who are responders to irinotecan. Reference genes ACTB, GAPD, GUSB, RPLP0 and TFRC are up-regulated (over-expressed).

The present invention further comprises protein expression profiles that are indicative of a cancer patient's tendency to respond to treatment with irinotecan. The protein expression profiles comprise those proteins encoded by the genes of the GEP that also are differentially expressed in colon cancers that are responsive to irinotecan therapy. The present protein expression profile (PEP) comprises at least one, and preferably a plurality, of proteins encoded by the genes selected from the group consisting of ERBB2, GRB7, Erk1 kinase, JNK1 kinase, BCL2, phospho-GSK-3beta, MMP11, CTSL2, CCNB1, BIRC5, MK167, STK6, MRP14, phospho-Akt, CD68, BAG1 and GSTM1. The protein expression profile may further include proteins encoded by reference genes. The currently preferred reference genes are ACTB, GAPD, GUSB, RPLP0 and TFRC. According to the invention, some or all of theses proteins are differentially expressed (e.g., up-regulated or down-regulated) in patients who are responders to irinotecan therapy. Specifically, proteins encoded by the following genes are up-regulated (over-expressed): ERBB2, GRB7, JNK1 kinase, BCL2, MK167, phospho-Akt, CD68 and BAG1; and proteins encoded by the following genes are down-regulated (under expressed): Erk1 kinase, phospho-GSK-3beta, MMP11, CTSL2, CCNB1, BIRC5, STK6, MRP14 and GSTM1, in patients who are responders to irinotecan. Reference proteins ACTB, GAPD, GUSB, RPLP0 and TFRC are up-regulated (over-expressed).

The gene and protein expression profiles of the present invention (referred to hereinafter as GPEPs) comprise a group of genes and proteins that are differentially expressed (e.g., up-regulated or down-regulated) in patients who are responders to irinotecan therapy relative to expression of the same genes in patients who are non-responders to this therapy. Patients having tumors that are non-responsive to irinotecan often experience recurrence of their disease or disease-related death. The GPEPs of the present invention thus can be used to predict not only responsiveness of a colon cancer to irinotecan therapy, but also the likelihood of recurrence of the cancer and/or disease-related death.

The present invention further comprises a method of determining if a patient is a responder or non-responder to treatment with irinotecan. The method comprises obtaining a tumor sample from the patient, determining the gene and/or protein expression profile of the sample, and determining from the gene or protein expression profile whether at least one, preferably at least 4, more preferably at least 10, and most preferably at least 16 of the genes selected from the group consisting of ERBB2, GRB7, Erk 1 kinase, JNK1 kinase, BCL2, phospho-GSK-3beta, MMP11, CTSL2, CCNB1, BIRC5, MK167, STK6, MRP14, phospho-Akt, CD68, BAG1 and GSTM1, or at least one protein selected from the proteins encoded by these genes, is differentially expressed in the sample. From this information, the treatment provider can ascertain whether the patient is likely to benefit from irinotecan therapy. The present method also can be used to predict late recurrence and disease related death associated with the therapy.

The present invention further comprises assays for determining the gene and/or protein expression profile in a patient's sample, and instructions for using the assay. The assay may be based on detection of nucleic acids (e.g., using nucleic acid probes specific for the nucleic acids of interest) or proteins or peptides (e.g., using antibodies specific for the proteins/peptides of interest). In a currently preferred embodiment, the assay comprises an immunohistochemistry (IHC) test in which tissue samples, preferably arrayed in a tissue microarray (TMA), and are contacted with antibodies specific for the proteins/peptides identified in the GPEP as being indicative of a patient's responsiveness to irinotecan.

BRIEF DESCRIPTION OF THE DRAWINGS

FIG. 1 is a graph showing the survival rates for patients treated with irinotecan HCl correlated with the present gene expression profile predicting responsiveness to irinotecan therapy.

DETAILED DESCRIPTION

The present invention provides gene and protein expression profiles and their use for predicting a patient's responsiveness to a cancer treatment. More specifically, the present GPEPs are indicative of whether a patient is a responder or a non-responder to treatment with irinotecan. Those patients identified as responders using the present GPEP are likely to benefit from irinotecan therapy, whereas those patients identified as non-responders may avoid unnecessary treatment with irinotecan and consider other treatment options in a timely manner. The present GPEPs also can be used to predict the likelihood of recurrence of colon cancer and disease related death associated with irinotecan therapy in some patients.

Irinotecan is a chemotherapeutic agent which belongs to the group of medicines called antineoplastics. It is indicated as first-line therapy for treating cancers of the colon or rectum. Irinotecan interferes with the growth of cancer cells, which are eventually destroyed. Because the growth of normal cells may also be affected by the medicine, other effects also may occur. These other effects may include: increased sweating and production of saliva, diarrhea, nausea (feeling sick) and vomiting, loss of appetite, lowered resistance to infection, bruising or bleeding, anemia, hair loss, tiredness and a general feeling of weakness. The present invention enables the treatment provider to determine in advance those patients likely to benefit from irinotecan treatment, and to consider alternative treatment options for non-responders. It is understood that treatment with irinotecan includes administering irinotecan alone and in combination with other therapeutic agents or adjuvants. The current indications for CAMPTOSAR® include administering irinotecan HCl in combination with 5-fluorouracil (5-FU) and leucovorin (LV) as first-line therapy for metastatic colorectal cancer, and alone as a second-line therapy for patients whose disease has returned or progressed following initial 5-FU therapy.

The genes comprising the present GEP include: ERBB2, GRB7, Erk1 kinase, JNK1 kinase, BCL2, phospho-GSK-3beta, MMP11, CTSL2, CCNB1, BIRC5, MK167, STK6, MRP14, phospho-Akt, CD68, BAG1 and GSTM1. In a preferred embodiment, the present gene expression profile further includes the following reference genes: ACTB, GAPD, GUSB, RPLP0 and TFRC. The NCBI Accession Number of a variant of each of these genes is set forth in Table 1; other variants exist which can be readily ascertained by reference to an appropriate database such as NCBI Entrez, and these variants are encompassed by the present invention. These genes are either up- or down-regulated in patients that are responsive to irinotecan therapy, and not in in patients that experience late recurrence of their disease or disease related death associated with the therapy. Accordingly, it is possible to determine in advance if a patient is likely to benefit from irinotecan therapy by obtaining a gene expression profile from the patient's tissue, and determining whether one or more of the genes in the present GEP is up- or down-regulated. Table 1 identifies the genes and indicates whether these genes are up- or down-regulated in patients that are responders to irinotecan therapy.

TABLE 1

| | GENE NAME | ALT GENE NAME | UP- or DOWN-REGULATION | NCBI ACCESSION NO. | SEQ ID NO. |
|---|---|---|---|---|---|
| HER2 Amplicon | ERBB2 | HER2 | Up | NM_004448 | 1 |
| | GRB7 | | Up | NM_005310 | 2 |
| ER Expression Cluster | Erk1 kinase | | Down | X60188 | 3 |
| | JNK1 kinase | | Up | NM_002750 | 4 |
| | BCL2 | | Up | NM_000633 | 5 |
| | GSK-3-beta | | Down | NM_002093 | 6 |
| Invasion Group | MMP11 | STMY3; stromolysin 3 | Down | NM_005940 | 7 |
| | CTSL2 | cathepsin L2 | Down | NM_001333 | 8 |
| Proliferation Cluster | CCNB1 | cyclin B1 | Down | NM_031966 | 9 |
| | BIRC5 | SURV; survivin | Down | NM_001168 | 10 |
| | MKI67 | Ki-67 antigen | Up | NM_002417 | 11 |
| | STK6 | STK15; BTAK | Down | NM_003600 | 12 |
| | Akt (Ser473) | | Up | NM_005163 | 13 |
| Other Genes | CD68 | | Up | NM_001251 | 14 |
| | BAG1 | | Up | NM_004323 | 15 |
| | GSTM1 | glutathione-s-transferase M1 | Down | NM_146421 | 16 |
| | MRP14 | S100 calcium binding protein A9 | Down | NM_002965 | 17 |
| Reference Genes | ACTB | β-Actin | Up | NM_001101 | 18 |
| | GAPD | GAPDH | Up | NM_002046 | 19 |

TABLE 1-continued

| GENE NAME | ALT GENE NAME | UP- or DOWN-REGULATION | NCBI ACCESSION NO. | SEQ ID NO. |
|---|---|---|---|---|
| GUSB | GUS | Up | NM_000181 | 20 |
| RPLP0 | | Up | NM_001002 | 21 |
| TFRC | | Up | NM_003234 | 22 |

In a preferred aspect of the present invention, the gene profile of the present invention comprises at least four, preferably between four and ten, more preferably at least ten, and most preferably at least sixteen, of the genes in the present GEP, up- or down-regulated as applicable, together with one or more reference genes.

The gene expression profiles of the invention can be used to predict the responsiveness of a colon cancer patient to irinotecan therapy. In one aspect, the present method comprises (a) obtaining a gene expression profile from a biological sample of a patient afflicted with colon cancer; (b) determining from the gene expression profile whether one or more of the following genes are up-regulated (over-expressed): ERBB2, GRB7, JNK1 kinase, BCL2, MK167, phospho-Akt, CD68 and BAG1; and/or whether at least one of the following genes are down-regulated (under-expressed): Erk1 kinase, phospho-GSK-3beta, MMP11, CTSL2, CCNB1, BIRC5, STK6, MRP14 and GSTM1. Preferably, expression of at least two reference genes also is measured. The predictive value of the gene profile for determining response to irinotecan increases with the number of these genes that are found to be up- or down-regulated in accordance with the invention. Preferably, at least about four, more preferably at least about ten and most preferably at least about sixteen of the genes in the present GPEP are differentially expressed.

The present invention further comprises protein expression profiles that are indicative of a cancer patient's tendency to respond to treatment with irinotecan. The protein expression profile comprises at least one, preferably a plurality, of proteins encoded by the genes selected from the group consisting of ERBB2, GRB7, Erk1 kinase, JNK1 kinase, BCL2, phospho-GSK-3beta, MMP11, CTSL2, CCNB1, BIRC5, MK167, STK6, MRP14, phospho-Akt, CD68, BAG1 and GSTM1. According to the invention, some or all of theses proteins are differentially expressed (e.g., up-regulated or down-regulated) in patients who are responders to irinotecan therapy. Specifically, the proteins encoded by the following genes are up-regulated (over-expressed): ERBB2, GRB7, JNK1 kinase, BCL2, MK167, phospho-Akt, CD68 and BAG1 and the proteins encoded by the following genes are down-regulated (under expressed): Erk1 kinase, phospho-GSK-3beta, MMP11, CTSL2, CCNB1, BIRC5, STK6, MRP14 and GSTM1, in patients who are responders to irinotecan. The following reference genes may be included: ACTB, GAPD, GUSB, RPLP0 and TFRC.

Table 2 lists the genes in the present GPEP and a variant of a protein encoded thereby. Table 2 also indicates whether expression of the protein is up- or down-regulated in patients responsive to irinotecan therapy. Table 2 includes the NCBI Accession No. of a variant of each protein; other variants of these proteins exist, which can be readily ascertained by reference to an appropriate database such as NCBI Entrez. Alternate names for the proteins listed in Table 2 also can be determined from the NCBI site.

TABLE 2

| GENE NAME | PROTEIN NAME(S) | UP- OR DOWN-REGULATION of PROTEIN | NCBI Accession No. of Protein | SEQ ID NO. of Protein |
|---|---|---|---|---|
| ERBB2 | ErbB-2; HER-2 | Up | NP_004439 | 23 |
| GRB7 | GRB7; growth factor receptor-bound protein 7 | Up | NP_005301 | 24 |
| Erk1 kinase | Erk1 kinase; mitogen activated protein kinase 3 | Down | P 27361 | 25 |
| JNK1 kinase | JNK1 Kinase | Up | NP_002741 | 26 |
| BCL2 | Bcl-2; B-cell lymphoma protein 2 | Up | NP_000624 | 27 |
| GSK-3-beta | Phospho-GSK-3 beta; glycogen synthase kinase 3 beta | Down | NP_002084 | 28 |
| MMP11 | STMY3; stromolysin 3; matrix metalloproteinase 11 | Down | NP_005931 | 29 |
| CTSL2 | cathepsin L2 | Down | NP_001324 | 30 |
| CCNB1 | cyclin B1 | Down | NP_114172 | 31 |
| BIRC5 | BIRC5; survivin | Down | NP_001159 | 32 |
| MKI67 | Ki-67 antigen | Up | NP_002408 | 33 |
| STK6 | STK15; BTAK; aurora-A | Down | NP_003591 | 34 |
| Akt | Phospho-akt; v-akt murine thyoma viral oncogene; RAC protein kinase alpha | Up | NP_005154 | 35 |
| CD68 | CD68 antigen; macrosialin | Up | NP_001242 | 36 |
| BAG1 | Bcl-2 associated athanogene | Up | NP_004314 | 37 |
| GSTM1 | glutathione-s-transferase M1 | Down | NP_666533 | 38 |
| ACTB | β-Actin | Up | NP_001092 | 39 |
| GAPD | GAPD | Up | NP_002037 | 40 |
| GUSB | GUS; gluuronidase beta | Up | NP_000172 | 41 |
| RPLP0 | Ribosomal protein P0 | Up | NP_000993 | 42 |
| TFRC | Transferrin receptor | Up | NP_003225 | 43 |

TABLE 2-continued

| GENE NAME | PROTEIN NAME(S) | UP- OR DOWN-REGULATION of PROTEIN | NCBI Accession No. of Protein | SEQ ID NO. of Protein |
|---|---|---|---|---|
| MRP14 | S100 calcium binding protein A9 | Down | NP_002956 | 44 |

DEFINITIONS

For convenience, the meaning of certain terms and phrases employed in the specification, examples, and appended claims are provided below. The definitions are not meant to be limiting in nature and serve to provide a clearer understanding of certain aspects of the present invention.

The term "genome" is intended to include the entire DNA complement of an organism, including the nuclear DNA component, chromosomal or extrachromosomal DNA, as well as the cytoplasmic domain (e.g., mitochondrial DNA).

The term "gene" refers to a nucleic acid sequence that comprises control and coding sequences necessary for producing a polypeptide or precursor. The polypeptide may be encoded by a full length coding sequence or by any portion of the coding sequence. The gene may be derived in whole or in part from any source known to the art, including a plant, a fungus, an animal, a bacterial genome or episome, eukaryotic, nuclear or plasmid DNA, cDNA, viral DNA, or chemically synthesized DNA. A gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. The gene may constitute an uninterrupted coding sequence or it may include one or more introns, bound by the appropriate splice junctions. The Term "gene" as used herein includes variants of the genes identified in Table 1.

The term "gene expression" refers to the process by which a nucleic acid sequence undergoes successful transcription and translation such that detectable levels of the nucleotide sequence are expressed.

The terms "gene expression profile" or "gene signature" refer to a group of genes expressed by a particular cell or tissue type wherein presence of the genes taken together or the differential expression of such genes, is indicative/predictive of a certain condition.

The term "nucleic acid" as used herein, refers to a molecule comprised of one or more nucleotides, i.e., ribonucleotides, deoxyribonucleotides, or both. The term includes monomers and polymers of ribonucleotides and deoxyribonucleotides, with the ribonucleotides and/or deoxyribonucleotides being bound together, in the case of the polymers, via 5' to 3' linkages. The ribonucleotide and deoxyribonucleotide polymers may be single or double-stranded. However, linkages may include any of the linkages known in the art including, for example, nucleic acids comprising 5' to 3' linkages. The nucleotides may be naturally occurring or may be synthetically produced analogs that are capable of forming base-pair relationships with naturally occurring base pairs. Examples of non-naturally occurring bases that are capable of forming base-pairing relationships include, but are not limited to, aza and deaza pyrimidine analogs, aza and deaza purine analogs, and other heterocyclic base analogs, wherein one or more of the carbon and nitrogen atoms of the pyrimidine rings have been substituted by heteroatoms, e.g., oxygen, sulfur, selenium, phosphorus, and the like. Furthermore, the term "nucleic acid sequences" contemplates the complementary sequence and specifically includes any nucleic acid sequence that is substantially homologous to the both the nucleic acid sequence and its complement.

The terms "array" and "microarray" refer to the type of genes or proteins represented on an array by oligonucleotides or protein-capture agents, and where the type of genes or proteins represented on the array is dependent on the intended purpose of the array (e.g., to monitor expression of human genes or proteins). The oligonucleotides or protein-capture agents on a given array may correspond to the same type, category, or group of genes or proteins. Genes or proteins may be considered to be of the same type if they share some common characteristics such as species of origin (e.g., human, mouse, rat); disease state (e.g., cancer); functions (e.g., protein kinases, tumor suppressors); same biological process (e.g., apoptosis, signal transduction, cell cycle regulation, proliferation, differentiation). For example, one array type may be a "cancer array" in which each of the array oligonucleotides or protein-capture agents correspond to a gene or protein associated with a cancer. An "epithelial array" may be an array of oligonucleotides or protein-capture agents corresponding to unique epithelial genes or proteins. Similarly, a "cell cycle array" may be an array type in which the oligonucleotides or protein-capture agents correspond to unique genes or proteins associated with the cell cycle.

The term "cell type" refers to a cell from a given source (e.g., a tissue, organ) or a cell in a given state of differentiation, or a cell associated with a given pathology or genetic makeup.

The term "activation" as used herein refers to any alteration of a signaling pathway or biological response including, for example, increases above basal levels, restoration to basal levels from an inhibited state, and stimulation of the pathway above basal levels.

The term "differential expression" refers to both quantitative as well as qualitative differences in the temporal and tissue expression patterns of a gene or a protein in diseased tissues or cells versus normal adjacent tissue. For example, a differentially expressed gene may have its expression activated or completely inactivated in normal versus disease conditions, or may be up-regulated (over-expressed) or down-regulated (under-expressed) in a disease condition versus a normal condition. Such a qualitatively regulated gene may exhibit an expression pattern within a given tissue or cell type that is detectable in either control or disease conditions, but is not detectable in both. Stated another way, a gene or protein is differentially expressed when expression of the gene or protein occurs at a higher or lower level in the diseased tissues or cells of a patient relative to the level of its expression in the normal (disease-free) tissues or cells of the patient and/or control tissues or cells.

The term "detectable" refers to an RNA expression pattern which is detectable via the standard techniques of polymerase chain reaction (PCR), reverse transcriptase-(RT) PCR, differential display, and Northern analyses, which are well known to those of skill in the art. Similarly, protein expression patterns may be "detected" via standard techniques such as Western blots.

The term "complementary" refers to the topological compatibility or matching together of the interacting surfaces of a probe molecule and its target. The target and its probe can be described as complementary, and furthermore, the contact surface characteristics are complementary to each other. Hybridization or base pairing between nucleotides or nucleic acids, such as, for example, between the two strands of a double-stranded DNA molecule or between an oligonucleotide probe and a target are complementary.

The term "biological sample" refers to a sample obtained from an organism (e.g., a human patient) or from components (e.g., cells) of an organism. The sample may be of any biological tissue or fluid. The sample may be a "clinical sample" which is a sample derived from a patient. Such samples include, but are not limited to, sputum, blood, blood cells (e.g., white cells), amniotic fluid, plasma, semen, bone marrow, and tissue or fine needle biopsy samples, urine, peritoneal fluid, and pleural fluid, or cells therefrom. Biological samples may also include sections of tissues such as frozen sections taken for histological purposes. A biological sample may also be referred to as a "patient sample."

A "protein" means a polymer of amino acid residues linked together by peptide bonds. The term, as used herein, refers to proteins, polypeptides, and peptides of any size, structure, or function. Typically, however, a protein will be at least six amino acids long. If the protein is a short peptide, it will be at least about 10 amino acid residues long. A protein may be naturally occurring, recombinant, or synthetic, or any combination of these. A protein may also comprise a fragment of a naturally occurring protein or peptide. A protein may be a single molecule or may be a multi-molecular complex. The term protein may also apply to amino acid polymers in which one or more amino acid residues is an artificial chemical analogue of a corresponding naturally occurring amino acid.

A "fragment of a protein," as used herein, refers to a protein that is a portion of another protein. For example, fragments of proteins may comprise polypeptides obtained by digesting full-length protein isolated from cultured cells. In one embodiment, a protein fragment comprises at least about six amino acids. In another embodiment, the fragment comprises at least about ten amino acids. In yet another embodiment, the protein fragment comprises at least about sixteen amino acids.

As used herein, an "expression product" is a biomolecule, such as a protein, which is produced when a gene in an organism is expressed. An expression product may comprise post-translational modifications.

The term "protein expression" refers to the process by which a nucleic acid sequence undergoes successful transcription and translation such that detectable levels of the amino acid sequence or protein are expressed.

The terms "protein expression profile" or "protein expression signature" refer to a group of proteins expressed by a particular cell or tissue type (e.g., neuron, coronary artery endothelium, or disease tissue), wherein presence of the proteins taken together or the differential expression of such proteins, is indicative/predictive of a certain condition.

The term "antibody" means an immunoglobulin, whether natural or partially or wholly synthetically produced. All derivatives thereof that maintain specific binding ability are also included in the term. The term also covers any protein having a binding domain that is homologous or largely homologous to an immunoglobulin binding domain. An antibody may be monoclonal or polyclonal. The antibody may be a member of any immunoglobulin class, including any of the human classes: IgG, IgM, IgA, IgD, and IgE.

The term "antibody fragment" refers to any derivative of an antibody that is less than full-length. In one aspect, the antibody fragment retains at least a significant portion of the full-length antibody's specific binding ability, specifically, as a binding partner. Examples of antibody fragments include, but are not limited to, Fab, Fab', $F(ab')_2$, scFv, Fv, dsFv diabody, and Fd fragments. The antibody fragment may be produced by any means. For example, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may comprise a single chain antibody fragment. In another embodiment, the fragment may comprise multiple chains that are linked together, for example, by disulfide linkages. The fragment may also comprise a multimolecular complex. A functional antibody fragment may typically comprise at least about 50 amino acids and more typically will comprise at least about 200 amino acids.

Determination of Gene Expression Profiles

The method used to identify and validate the present gene expression profiles indicative of whether a colon cancer patient will respond to treatment with irinotecan is described below. Other methods for identifying gene and/or protein expression profiles are known; any of these alternative methods also could be used. See, e.g., Chen et al., *NEJM,* 356 (1): 11-20 (2007); Lu et al., *PLOS Med.,* 3 (12):e467 (2006); Golub et al., *Science,* 286:531-537 (1999).

The present method utilizes parallel testing in which, in one track, those genes which are over-/under-expressed as compared to normal (non-cancerous) tissue samples are identified, and, in a second track, those genes comprising chromosomal insertions or deletions as compared to normal samples are identified, from the same samples. These two tracks of analysis produce two sets of data. The data are analyzed using an algorithm which identifies the genes of the gene expression profile (i.e., those genes that are differentially expressed in cancer tissue). Positive and negative controls may be employed to normalize the results, including eliminating those genes and proteins that also are differentially expressed in normal tissues from the same patients, and confirming that the gene expression profile is unique to the cancer of interest.

In the present instance, as an initial step, biological samples were acquired from patients afflicted with colorectal cancer. Approximately five-hundred (500) tissue samples obtained from colorectal cancer patients were used, including tumor tissue and adjacent normal (undiseased) colon tissue. The tissue samples were obtained from patients suffering from various stages of colon cancer, and included those obtained from patients who have been treated with irinotecan. All of the patients were responders to irinotecan therapy. Clinical information associated with each sample, including treatment with irinotecan and the outcome of the treatment, was recorded in a database. Clinical information also includes information such as age, sex, medical history, treatment history, symptoms, family history, recurrence (yes/no), etc. Control samples, including samples of normal (non-cancerous) tissue also were acquired from the same patients. Samples of normal undiseased colon tissue from a set of healthy individuals were used as positive controls, and colon tumor samples from patients who were non-responders to irinotecan therapy were used as negative controls.

Gene expression profiles (GEPs) then were generated from the biological samples based on total RNA according to well-established methods. Briefly, a typical method involves isolating total RNA from the biological sample, amplifying the RNA, synthesizing cDNA, labeling the cDNA with a detectable label, hybridizing the cDNA with a genomic array, such as the Affymetrix U133 GeneChip®, and determining binding of the labeled cDNA with the genomic array by measuring the intensity of the signal from the detectable label bound to the array. See, e.g., the methods described in Lu, et al., Chen, et al. and Golub, et al., supra, and the references cited therein, which are incorporated herein by reference. The resulting expression data are input into a database.

MRNAs in the tissue samples can be analyzed using commercially available or customized probes or oligonucleotide arrays, such as cDNA or oligonucleotide arrays. The use of these arrays allows for the measurement of steady-state mRNA levels of thousands of genes simultaneously, thereby presenting a powerful tool for identifying effects such as the onset, arrest or modulation of uncontrolled cell proliferation. Hybridization and/or binding of the probes on the arrays to the nucleic acids of interest from the cells can be determined by detecting and/or measuring the location and intensity of the signal received from the labeled probe or used to detect a DNA/RNA sequence from the sample that hybridizes to a nucleic acid sequence at a known location on the microarray. The intensity of the signal is proportional to the quantity of cDNA or mRNA present in the sample tissue. Numerous arrays and techniques are available and useful. Methods for determining gene and/or protein expression in sample tissues are described, for example, in U.S. Pat. No. 6,271,002; U.S. Pat. No. 6,218,122; U.S. Pat. No. 6,218,114; and U.S. Pat. No. 6,004,755; and in Wang et al., *J. Clin. Oncol.,* 22 (9): 1564-1671 (2004); Golub et al, (supra); and Schena et al., *Science,* 270:467-470 (1995); all of which are incorporated herein by reference.

The gene analysis aspect utilized in the present method investigates gene expression as well as insertion/deletion data. As a first step, RNA was isolated from the tissue samples and labeled. Parallel processes were run on the sample to develop two sets of data: (1) over-/under-expression of genes based on mRNA levels; and (2) chromosomal insertion/deletion data. These two sets of data were then correlated by means of an algorithm. Over-/under-expression of the genes in each cancer tissue sample were compared to gene expression in the normal (non-cancerous) samples, and a subset of genes that were differentially expressed in the cancer tissue was identified. Preferably, levels of up- and down-regulation are distinguished based on fold changes of the intensity measurements of hybridized microarray probes. A difference of about 2.0 fold or greater is preferred for making such distinctions, or a p-value of less than about 0.05. That is, before a gene is said to be differentially expressed in diseased versus normal cells, the diseased cell is found to yield at least about 2 times greater or less intensity of expression than the normal cells. Generally, the greater the fold difference (or the lower the p-value), the more preferred is the gene for use as a diagnostic or prognostic tool. Genes selected for the gene signatures of the present invention have expression levels that result in the generation of a signal that is distinguishable from those of the normal or non-modulated genes by an amount that exceeds background using clinical laboratory instrumentation.

Statistical values can be used to confidently distinguish modulated from non-modulated genes and noise. Statistical tests can identify the genes most significantly differentially expressed between diverse groups of samples. The Student's t-test is an example of a robust statistical test that can be used to find significant differences between two groups. The lower the p-value, the more compelling the evidence that the gene is showing a difference between the different groups. Nevertheless, since microarrays allow measurement of more than one gene at a time, tens of thousands of statistical tests may be asked at one time. Because of this, it is unlikely to observe small p-values just by chance, and adjustments using a Sidak correction or similar step as well as a randomization/permutation experiment can be made. A p-value less than about 0.05 by the t-test is evidence that the expression level of the gene is significantly different. More compelling evidence is a p-value less then about 0.05 after the Sidak correction is factored in. For a large number of samples in each group, a p-value less than about 0.05 after the randomization/permutation test is the most compelling evidence of a significant difference.

Another parameter that can be used to select genes that generate a signal that is greater than that of the non-modulated gene or noise is the measurement of absolute signal difference. Preferably, the signal generated by the differentially expressed genes differs by at least about 20% from those of the normal or non-modulated gene (on an absolute basis). It is even more preferred that such genes produce expression patterns that are at least about 30% different than those of normal or non-modulated genes.

This differential expression analysis can be performed using commercially available arrays, for example, Affymetrix U133 GeneChip® arrays (Affymetrix, Inc.). These arrays have probe sets for the whole human genome immobilized on the chip, and can be used to determine up- and down-regulation of genes in test samples. Other substrates having affixed thereon human genomic DNA or probes capable of detecting expression products, such as those available from Affymetrix, Agilent Technologies, Inc. or Illumina, Inc., also may be used. Currently preferred gene microarrays for use in the present invention include Affymetrix U133 GeneChip® arrays and Agilent Technologies genomic cDNA microarrays. Instruments and reagents for performing gene expression analysis are commercially available. See, e.g., Affymetrix GeneChip® System. The expression data obtained from the analysis then is input into the database.

In the second arm of the present method, chromosomal insertion/deletion data for the genes of each sample as compared to samples of normal tissue was obtained. The insertion/deletion analysis was generated using an array-based comparative genomic hybridization ("CGH"). Array CGH measures copy-number variations at multiple loci simultaneously, providing an important tool for studying cancer and developmental disorders and for developing diagnostic and therapeutic targets. Microchips for performing array CGH are commercially available, e.g., from Agilent Technologies. The Agilent chip is a chromosomal array which shows the location of genes on the chromosomes and provides additional data for the gene signature. The insertion/deletion data from this testing is input into the database.

The analyses are carried out on the same samples from the same patients to generate parallel data. The same chips and sample preparation are used to reduce variability.

The expression of certain genes known as "reference genes" "control genes" or "housekeeping genes" also is determined, preferably at the same time, as a means of ensuring the veracity of the expression profile. Reference genes are genes that are consistently expressed in many tissue types, including cancerous and normal tissues, and thus are useful to normalize gene expression profiles. See, e.g., Silvia et al., *BMC Cancer,* 6:200 (2006); Lee et al., *Genome Research,* 12 (2):292-297 (2002); Zhang et al., *BMC Mol. Biol.,* 6:4 (2005).

Determining the expression of reference genes in parallel with the genes in the unique gene expression profile provides further assurance that the techniques used for determination of the gene expression profile are working properly. The expression data relating to the reference genes also is input into the database. In a currently preferred embodiment, the following genes are used as reference genes: ACTB, GAPD, GUSB, RPLP0 and/or TRFC.

Data Correlation

The differential expression data and the insertion/deletion data in the database are correlated with the clinical outcomes information associated with each tissue sample also in the database by means of an algorithm to determine a gene expression profile for determining therapeutic efficacy of irinotecan, as well as late recurrence of disease and/or disease-related death associated with irinotecan therapy. Various algorithms are available which are useful for correlating the data and identifying the predictive gene signatures. For example, algorithms such as those identified in Xu et al., A Smooth Response Surface Algorithm For Constructing A Gene Regulatory Network, *Physiol. Genomics* 11:11-20 (2002), the entirety of which is incorporated herein by reference, may be used for the practice of the embodiments disclosed herein.

Another method for identifying gene expression profiles is through the use of optimization algorithms such as the mean variance algorithm widely used in establishing stock portfolios. One such method is described in detail in the patent application US Patent Application Publication No. 2003/0194734. Essentially, the method calls for the establishment of a set of inputs expression as measured by intensity) that will optimize the return (signal that is generated) one receives for using it while minimizing the variability of the return. The algorithm described in Irizarry et al., *Nucleic Acids Res.,* 31 e15 (2003) also may be used. The currently preferred algorithm is the JMP Genomics algorithm available from JMP Software.

The process of selecting gene expression profiles also may include the application of heuristic rules. Such rules are formulated based on biology and an understanding of the technology used to produce clinical results, and are applied to output from the optimization method. For example, the mean variance method of gene signature identification can be applied to microarray data for a number of genes differentially expressed in subjects with colorectal cancer. Output from the method would be an optimized set of genes that could include some genes that are expressed in peripheral blood as well as in diseased tissue. If samples used in the testing method are obtained from peripheral blood and certain genes differentially expressed in instances of cancer could also be differentially expressed in peripheral blood, then a heuristic rule can be applied in which a portfolio is selected from the efficient frontier excluding those that are differentially expressed in peripheral blood. Of course, the rule can be applied prior to the formation of the efficient frontier by, for example, applying the rule during data pre-selection.

Other heuristic rules can be applied that are not necessarily related to the biology in question. For example, one can apply a rule that only a certain percentage of the portfolio can be represented by a particular gene or group of genes. Commercially available software such as the Wagner software readily accommodates these types of heuristics (Wagner Associates Mean-Variance Optimization Application). This can be useful, for example, when factors other than accuracy and precision have an impact on the desirability of including one or more genes.

As an example, the algorithm may be used for comparing gene expression profiles for various genes (or portfolios) to ascribe prognoses. The gene expression profiles of each of the genes comprising the portfolio are fixed in a medium such as a computer readable medium. This can take a number of forms. For example, a table can be established into which the range of signals (e.g., intensity measurements) indicative of disease is input. Actual patient data can then be compared to the values in the table to determine whether the patient samples are normal or diseased. In a more sophisticated embodiment, patterns of the expression signals (e.g., fluorescent intensity) are recorded digitally or graphically. The gene expression patterns from the gene portfolios used in conjunction with patient samples are then compared to the expression patterns. Pattern comparison software can then be used to determine whether the patient samples have a pattern indicative of recurrence of the disease. Of course, these comparisons can also be used to determine whether the patient is not likely to experience disease recurrence. The expression profiles of the samples are then compared to the portfolio of a control cell. If the sample expression patterns are consistent with the expression pattern for recurrence of a colorectal cancer then (in the absence of countervailing medical considerations) the patient is treated as one would treat a relapse patient. If the sample expression patterns are consistent with the expression pattern from the normal/control cell then the patient is diagnosed negative for colorectal cancer.

A method for analyzing the gene signatures of a patient to determine prognosis of cancer is through the use of a Cox hazard analysis program. The analysis may be conducted using S-Plus software (commercially available from Insightful Corporation). Using such methods, a gene expression profile is compared to that of a profile that confidently represents relapse (i.e., expression levels for the combination of genes in the profile is indicative of relapse). The Cox hazard model with the established threshold is used to compare the similarity of the two profiles (known relapse versus patient) and then determines whether the patient profile exceeds the threshold. If it does, then the patient is classified as one who will relapse and is accorded treatment such as adjuvant therapy. If the patient profile does not exceed the threshold then they are classified as a non-relapsing patient. Other analytical tools can also be used to answer the same question such as, linear discriminate analysis, logistic regression and neural network approaches. See, e.g., software available from JMP statistical software.

Numerous other well-known methods of pattern recognition are available. The following references provide some examples:

Weighted Voting: Golub, T R., Slonim, D K., Tamaya, P., Huard, C., Gaasenbeek, M., Mesirov, J P., Coller, H., Loh, L., Downing, J R., Caligiuri, M A., Bloomfield, C D., Lander, E S. Molecular classification of cancer: class discovery and class prediction by gene expression monitoring. Science 286:531-537, 1999.

Support Vector Machines: Su, A I., Welsh, J B., Sapinoso, L M., Kern, S G., Dimitrov, P., Lapp, H., Schultz, P G., Powell, S M., Moskaluk, C A., Frierson, H F. Jr., Hampton, G M. Molecular classification of human carcinomas by use of gene expression signatures. Cancer Research 61:7388-93, 2001. Ramaswamy, S., Tamayo, P., Rifkin, R., Mukherjee, S., Yeang, C H., Angelo, M., Ladd, C., Reich, M., Latulippe, E., Mesirov, J P., Poggio, T., Gerald, W., Loda, M., Lander, E S., Gould, T R. Multiclass cancer diagnosis using tumor gene expression signatures Proceedings of the National Academy of Sciences of the USA 98:15149-15154, 2001.

K-nearest Neighbors: Ramaswamy, S., Tamayo, P., Rifkin, R., Mukherjee, S., Yeang, C H., Angelo, M., Ladd, C., Reich, M., Latulippe, E., Mesirov, J P., Poggio, T., Gerald, W., Loda, M., Lander, E S., Gould, T R. Multiclass cancer diagnosis using tumor gene expression signatures Proceedings of the National Academy of Sciences of the USA 98:15149-15154, 2001.

Correlation Coefficients: van't Veer L J, Dai H, van de Vijver M J, He Y D, Hart A A, Mao M, Peterse H L, van der Kooy K, Marton M J, Witteveen A T, Schreiber G J, Kerkhoven R M, Roberts C, Linsley P S, Bernards R, Friend S H. Gene expression profiling predicts clinical outcome of breast cancer, Nature. 2002 Jan. 31; 415 (6871):530-6.

The gene expression analysis identifies a gene expression profile (GEP) unique to the cancer samples, that is, those genes which are differentially expressed by the cancer cells. This GEP then is validated, for example, using real-time quantitative polymerase chain reaction (RT-qPCR), which may be carried out using commercially available instruments and reagents, such as those available from Applied Biosystems.

In the present instance, the results of the gene expression analysis showed that in colon cancer patients who were responsive to treatment with irinotecan, the following genes were up-regulated: ERBB2, GRB7, JNK1 kinase, BCL2, MK167, phospho-Akt, CD-68 and BAG1, and the following genes were down-regulated: Erk1 kinase, pospho-GSK-3beta, MMP11, CTSL2, CCNB1, BIRC5, STK6, MRP14 and GSTM1, compared with expression of these genes in the normal colon tissue samples from these patients, and from the negative control patients, i.e., the tissue samples from patients that had experienced a recurrence of their cancer after treatment with irinotecan. Reference genes ACTB, GAPD, GUSB, RPLP0 and TFRC all were up-regulated.

Determination of Protein Expression Profiles

Not all genes expressed by a cell are translated into proteins, therefore, once a GEP has been identified, it is desirable to ascertain whether proteins corresponding to some or all of the differentially expressed genes in the GEP also are differentially expressed by the same cells or tissue. Therefore, protein expression profiles (PEPs) are generated from the same cancer and control tissues used to identify the GEPs. PEPs also are used to validate the GEP in other colon cancer patients.

The preferred method for generating PEPs according to the present invention is by immunohistochemistry (IHC) analysis. In this method antibodies specific for the proteins in the PEP are used to interrogate tissue samples from colon cancer patients. Other methods for identifying PEPs are known, e.g. in situ hybridization (ISH) using protein-specific nucleic acid probes. See, e.g., Hofer et al., *Clin. Can. Res.,* 11 (16):5722 (2005); Volm et al., *Clin. Exp. Metas.,* 19 (5):385 (2002). Any of these alternative methods also could be used.

In the present instance, samples of colon tumor tissue and normal colon tissue were obtained from patients afflicted with colon cancer who had undergone successful treatment with irinotecan; these are the same samples used for identifying the GEP. The tissue samples were arrayed on tissue microarrays (TMAs) to enable simultaneous analysis. TMAs consist of substrates, such as glass slides, on which up to about 1000 separate tissue samples are assembled in array fashion to allow simultaneous histological analysis. The tissue samples may comprise tissue obtained from preserved biopsy samples, e.g., paraffin-embedded or frozen tissues. Techniques for making tissue microarrays are well-known in the art. See, e.g., Simon et al., *BioTechniques,* 36 (1):98-105 (2004); Kallioniemi et al, WO 99/44062; Kononen et al., *Nat. Med.,* 4:844-847 (1998). In the present instance, a hollow needle was used to remove tissue cores as small as 0.6 mm in diameter from regions of interest in paraffin embedded tissues. The "regions of interest" are those that have been identified by a pathologist as containing the desired diseased or normal tissue. These tissue cores then were inserted in a recipient paraffin block in a precisely spaced array pattern. Sections from this block were cut using a microtome, mounted on a microscope slide and then analyzed by standard histological analysis. Each microarray block can be cut into approximately 100 to approximately 500 sections, which can be subjected to independent tests.

The TMAs were prepared using two tissue samples from each patient: one of colon tumor tissue and one of normal colon tissue. Control arrays also were prepared; in a currently preferred embodiment, the following control TMAs were used: an array containing normal colon tissue samples from healthy, cancer-free individuals; an array of "positive controls" containing tumor tissues from cancer patients afflicted with cancers other than colon cancer, e.g., breast cancer, lung cancer, prostate cancer, etc; and an array of "negative controls" containing tumor samples from colon cancer patients that had experienced recurrences of the cancer after treatment with irinotecan—that is, patients who were "non-responders" to the therapy.

Proteins in the tissue samples may be analyzed by interrogating the TMAs using protein-specific agents, such as antibodies or nucleic acid probes, such as aptamers. Antibodies are preferred for this purpose due to their specificity and availability. The antibodies may be monoclonal or polyclonal antibodies, antibody fragments, and/or various types of synthetic antibodies, including chimeric antibodies, or fragments thereof. Antibodies are commercially available from a number of sources (e.g., Abcam, Cell Signaling Technology, Santa Cruz Biotechnology), or may be generated using techniques well-known to those skilled in the art. The antibodies typically are equipped with detectable labels, such as enzymes, chromogens or quantum dots, that permit the antibodies to be detected. The antibodies may be conjugated or tagged directly with a detectable label, or indirectly with one member of a binding pair, of which the other member contains a detectable label. Detection systems for use with are described, for example, in the website of Ventana Medical Systems, Inc. Quantum dots are particularly useful as detectable labels. The use of quantum dots is described, for example, in the following references: Jaiswal et al., *Nat. Biotechnol.,* 21:47-51 (2003); Chan et al., *Curr. Opin. Biotechnol.,* 13:40-46 (2002); Chan et al., *Science,* 281:435-446 (1998).

The use of antibodies to identify proteins of interest in the cells of a tissue, referred to as immunohistochemistry (IHC), is well established. See, e.g., Simon et al., *BioTechniques,* 36 (1):98 (2004); Haedicke et al., *BioTechniques,* 35 (1):164 (2003), which are hereby incorporated by reference. The IHC assay can be automated using commercially available instruments, such as the Benchmark instruments available from Ventana Medical Systems, Inc.

In the present instance, the TMAs were contacted with antibodies specific for the proteins encoded by the genes identified in the gene expression study as being up- or down-regulated in colon cancer patients who were responders to therapy with irinotecan in order to determine expression of these proteins in each type of tissue. The results of the IHC assay showed that in colon cancer patients who were responsive to treatment with irinotecan, the following proteins were up-regulated: ERBB2, GRB7, JNK1 kinase, BCL2, MK167, phospho-Akt, CD-68 and BAG1, and the following proteins were down-regulated: Erk1 kinase, pospho-GSK-3beta, MMP11, CTSL2, CCNB1, BIRC5, STK6, MRP14 and GSTM1, compared with expression of these proteins in the normal colon tissue samples from these patients, and in the negative control samples, i.e., colon tumor samples from patients that had experienced a recurrence of their cancer after treatment with irinotecan (non-responders). Additionally, IHC analysis showed that a majority of these proteins were not up- or down-regulated in the positive control tissue samples. The reference proteins ACTB, GAPD, GUSB, RPLP0 and TFRC all were up-regulated.

Assays

The present invention further comprises methods and assays for determining whether a colon cancer patient is likely to respond to treatment with irinotecan, and/or to predict whether the cancer is likely to recur, or disease-related death. According to one aspect, a formatted IHC assay can be used for determining if a colon cancer tumor exhibits the present GPEP. The assays may be formulated into kits that include all or some of the materials needed to conduct the analysis, including reagents (antibodies, detectable labels, etc.) and instructions.

The assay method of the invention comprises contacting a tumor sample from a colon cancer patient with a group of antibodies specific for some or all of the genes or proteins in the present GPEP, and determining the occurrence of up- or down-regulation of these genes or proteins in the sample. The use of TMAs allows numerous samples, including control samples, to be assayed simultaneously.

In a preferred embodiment, the method comprises contacting a tumor sample from a colon cancer patient and control samples with a group of antibodies specific for some or all of the proteins in the present GPEP, and determining the occurrence of up- or down-regulation of these proteins. Up-regulation of some or all of the following proteins: ERBB2, GRB7, JNK1 kinase, BCL2, MK167, phospho-Akt, CD68 and BAG1; and down-regulation of some or all of the following proteins: Erk1 kinase, phospho-GSK-3beta, MMP11, CTSL2, CCNB1, BIRC5, STK6, MRP14 and GSTM1, is indicative of the patient's responsiveness to irinotecan. Preferably, at least about four, preferably between about four and ten, and most preferably between about ten and sixteen (or more) antibodies are used in the present method.

The method preferably also includes detecting and/or quantitating control or "reference proteins". Detecting and/or quantitating the reference proteins in the samples normalizes the results and thus provides further assurance that the assay is working properly. In a currently preferred embodiment, antibodies specific for one or more of the following reference proteins are included: ACTB, GAPD, GUSB, RPLP0 and/or TRFC.

The present invention further comprises a kit containing reagents for conducting an IHC analysis of tissue samples or cells from colon cancer patients, including antibodies specific for at least four of the proteins in the GPEP and for any reference proteins. The antibodies are preferably tagged with means for detecting the binding of the antibodies to the proteins of interest, e.g., detectable labels. Preferred detectable labels include fluorescent compounds or quantum dots, however other types of detectable labels may be used. Detectable labels for antibodies are commercially available, e.g. from Ventana Medical Systems, Inc.

Immunohistochemical methods for detecting and quantitating protein expression in tissue samples are well known. Any method that permits the determination of expression of several different proteins can be used. See. e.g., Signoretti et al., "Her-2-neu Expression and Progression Toward Androgen Independence in Human Prostate Cancer," *J. Natl. Cancer Instit.,* 92 (23):1918-25 (2000); Gu et al., "Prostate stem cell antigen (PSCA) expression increases with high gleason score, advanced stage and bone metastasis in prostate cancer," *Oncogene,* 19:1288-96 (2000). Such methods can be efficiently carried out using automated instruments designed for immunohistochemical (IHC) analysis. Instruments for rapidly performing such assays are commercially available, e.g., from Ventana Molecular Discovery Systems or Lab Vision Corporation. Methods according to the present invention using such instruments are carried out according to the manufacturer's instructions.

Protein-specific antibodies for use in such methods or assays are readily available or can be prepared using well-established techniques. Antibodies specific for the proteins in the GPEP disclosed herein can be obtained, for example, from Cell Signaling Technology, Inc., Santa Cruz Biotechnology, Inc.

The present invention is illustrated further by the following non-limiting Examples.

EXAMPLES

A series of prognostic factors were tested in order to validate the efficacy of the gene/protein expression profile (GPEP) of the present invention for predicting the therapeutic response of irinotecan therapy. The expression levels of these factors, consisting of the twenty-two (22) proteins in the present GPEP listed in Table 2 (which includes seventeen differentially expressed proteins and five reference proteins), was determined by an immunohistochemical methodology in biopsy tissue samples obtained from late-stage colon cancer patients whose treatment with irinotecan had been successful, as well as samples from patients whose treatment was unsuccessful, e.g., who had experienced late recurrence (LRec) or disease-related death (DRD) associated with the therapy. For purposes of selecting the patients for the study, irinotecan therapy was determined to have failed if a recurrence was present within three years of diagnosis.

According to the current prescribing information for CAMPTOSAR®, irinotecan currently is indicated for first line therapy of colon cancer in combination with 5-fluorouracil (5-FU) and leucovorin, or following initial 5-FU therapy in late stage colon cancer patients. The patients in the study had been treated using the combination therapy according to the prescribing information for CAMPTOSAR®.

Gene/Protein Expression Profile (GPEP):

In this study, formalin fixed paraffin embedded primary colon cancer specimens from 280 patients (median age 63 years) followed for a minimum of 120 months were evaluated for primary tumor size, histologic grade and Duke's status. These patients included only those who had been responsive to irinotecan therapy. No patients received adjuvant treatment prior to the first episode of disease recurrence. Using the techniques described above, a GPEP was generated, consisting of the following seventeen genes and encoded proteins: ERBB2, GRB7, JNK1 kinase, BCL2, MK167, phospho-Akt, CD68, BAG1, Erk1 kinase, phospho-GSK-3beta, MMP11, CTSL2, CCNB1, BIRC5, STK6, MRP14 and GSTM1, and five reference genes and proteins: ACTB, GAPD, GUSB, RPLP0 and TRFC.

Tissue microarrays were prepared using the colon adenocarinomas and normal (non-cancerous) colon tissue from patients described above having late stage cancers who were treated with irinotecan. TMAs also were prepared containing positive and negative control samples. The TMAs used in this study are described in Table A:

TABLE A

| Tissue Micro Arrays | |
|---|---|
| Normal Screening Array | This array contained samples of normal (non-cancerous) colon tissue from 200 patients (2 samples per patient). |
| Colon Treatment Irinotecan | This array contained 280 patient samples obtained from the patients afflicted with late-stage colon adenocarcinoma who had been treated with CAMPTOSAR ® together with normal colon tissue samples from each patient. |
| Cancer Screening Survey Array (Positive control array) | This array contained 200 tumor samples for cancers other than colon cancer, including breast cancer, pancreatic cancer, prostate cancer, ovarian cancer, salivary gland cancer, lung cancer and brain tumor. |
| Colon Cancer Progression (Negative control array - TE30 array) | This array contained samples of colon cancer tissue from thirty patients who had progressed to the next stage of cancer or experienced a recurrence of cancer after treatment with CAMPTOSAR ®. |

The TMAs were constructed according to the following procedure:

Construction: An instrument was used for creating holes in a recipient paraffin block that are then filled with tissue core acquired from a selected donor block. These tissue cores were punched with a thin walled, sharpened borer. An X-Y precision guide allowed for the orderly placement of these tissue samples in an array format.

Presentation: TMA sections were cut at 4 microns and mounted on positively charged glass microslides. Individual elements are 0.6 mm in diameter, spaced 0.2 mm apart.

Elements: In addition to TMAs containing the colon cancer samples, screening and control arrays were prepared containing the tissue samples described in Table A.

Specificity: The TMAs were designed for use with specialty staining and immunohistochemical methods for gene expression screening purposes by using monoclonal and polyclonal antibodies over a wide range of characterized tissue types.

Accompanying each array was an array locator map and spreadsheet containing patient diagnostic, histologic and demographic data for each element.

Immunohistochemical (IHC) staining techniques were used for the visualization of tissue (cell) proteins present in the tissue samples on the TMAs. These techniques were based on the immunoreactivity of antibodies and the chemical properties of enzyme or enzyme complexes, which react with colorless substrate-chromogens to produce a colored end product. Initial immunoenzymatic stains utilized the direct method, which conjugated directly to an antibody with known antigenic specificity (primary antibody).

A modified labeled avidin-biotin technique was employed in which a biotinylated secondary antibody formed a complex with peroxidase-conjugated strepavidin molecules. Endogenous peroxidase activity was quenched by the addition of 3% hydrogen peroxide. The specimens then were incubate with the primary antibodies followed by sequential incubations with the biotinylated secondary link antibody (containing anti-rabbit or anti-mouse immunoglobulins) and peroidase labeled strepavidin. The primary antibody, secondary antibody, and avidin enzyme complex is then visualized utilizing a substrate-chromogen that produces a brown pigment at the antigen site that is visible by light microscopy. The antibodies utilized in this study were antibodies specific for the proteins in the present protein expression profile, i.e., ERBB2, GRB7, JNK1 kinase, BCL2, MK167, phospho-Akt, CD68, BAG1, Erk1 kinase, phospho-GSK-3beta, MMP11, CTSL2, CCNB1, BIRC5, STK6, MRP14 and GSTM1, and reference proteins ACTB, GAPD, GUSB, RPLP0 and TRFC. All antibodies were obtained from Cell Signaling Technology, Inc., and Abeam.

Automated IHC Staining Procedure:

1. Heat-induced epitope retrieval (HIER) using 10 mM Citrate buffer solution. pH 6.0, was performed as follows:
   a. Deparaffinized and rehydrated sections were placed in a slide staining rack.
   b. The rack was placed in a microwaveable pressure cooker, 750 ml of 10 mM Citrate buffer pH 6.0 was added to cover the slides.
   c. The covered pressure cooker was placed in the microwave on high power for 15 minutes.
   d. The pressure cooker was removed from the microwave and cooled until the pressure indicator drops and the cover could be safely removed.
   e. The slides were allowed to cool to room temperature (RT), and IHC staining was carried out.
2. Slides were treated with 3% $H_20_2$ for 10 min. at RT to quench endogenous peroxidase activity.
3. Slides were gently rinsed with phosphate buffered saline (PBS).
4. The primary antibodies were applied at the predetermined dilution (according to Cell Signaling Technology's specifications) for 30 min. at RT. Normal mouse or rabbit serum 1:750 dilution was applied to negative control slides.
5. Slides were gently rinsed with phosphate buffer saline (PBS).
6. Secondary biotinylated link antibodies (secondary antibodies: biotinylated anti-chicken and anti-mouse immunoglobulins in phosphate buffered saline (PBS), containing carrier protein and 1.5 mM sodium azide) were applied for 30 min. at RT.
7. Slides were rinsed with phosphate buffered saline (PBS).
8. The slides were treated with streptavidin-HRP (streptavidin conjugated to horseradish peroxidase in PBS containing carrier protein and anti-microbial agents from Ventana) for 30 min. at room temperature.
9. Slides were rinsed with phosphate buffered saline (PBS).
10. The slides were treated with substrate/chromogen (substrate-imidazole-HCl buffer pH 7.5 containing $H_2O_2$ and anti-microbial agents; DAB-3,3'-diaminobenzidine in chromogen solution from Ventana) for 10 min. at room temperature.
11. Slides were rinsed with distilled water.
12. Counterstain in Hematoxylin was applied for 1 min.
13. Slides were washed in running water for 2 min.
14. The slides were then dehydrated, cleared and the coverglass was mount.

All primary antibodies were titrated to dilutions according to the manufacturer's specifications. Staining of the TE30 test array slides (described below) was performed both with and without epitope retrieval (HIER). The slides were screened by a pathologist to determine the optimal working dilution. Pretreatment with HIER, provided strong specific staining with little to no background. The above-described IHC procedure was carried out using a Benchmark instrument from Ventana Medical Systems, Inc.

Scoring Criteria:

Staining was scored by a pathologist on a 0-3+ scale, with 0=no staining, and trace being less than 1+ but greater than 0. The scoring procedures are described in Signoretti, et al., *J. Nat. Cancer Inst., vol.* 92 (23):1918 (December 2000) and Gu, et al., *Oncogene, vol.* 19, p. 1288 (2000). Grades of 1+ to 3+ represent increased intensity of staining with 3+ being strong, dark brown staining. Scoring criteria was also based on total percentage of staining 0=0%, 1=less than 25%, 2=25-50% and 3=greater than 50%. The percent positivity and the intensity of staining for both Nuclear and Cytoplasmic as well as sub-cellular components were analyzed. Both the intensity and percentage positive scores were multiplied to produce one number 0-9. 3+ staining was determined from known expression of the antigen from the positive controls.

Positive tissue controls were defined via standard Western Blot analysis. This experiment was performed to confirm the level of protein expression in each of the control tissues. Negative controls also were defined by the same methodology. The positive controls consisted of breast, prostate, bung, salivary gland, pancreas and ovarian adenocarcinomas and brain tumor tissue samples unrelated to the colon cancer patients who were the subjects of the study. Colon cancer tissue samples from patients who were non-responsive to irinotecan therapy (i.e., who experienced recurrence of the disease or death from the disease after treatment) were used as negative controls.

Positive expression also was evaluated using a xenograft array. SCID mice were injected with tumor cells derived from patients who were responsive to treatment with irinotecan, and the tumors were allowed to grow in the mice. Once the tumors were established, the mice were injected with 200 mg/kg of irinotecan, and the mice were monitored to observe responsiveness to the drug. As a result of treatment with irinotecan, the tumors formed in the SCID mice were reduced or eliminated. Prior to treatment with the drug, samples of the tumors were extracted from the mice and used to make a TMA. IHC assay of the TMA containing the mouse xenograft tumor tissue showed that the xenograft tumors have the same GPEP as that identified in the human patients who were responsive to irinotecan therapy.

All runs were grouped by antibody and tissue arrays which ensured that the runs were normalized, meaning that all of the tissue arrays were stained under the same conditions with the same antibody on the same run. The reproducibility was compared and validated.

Results:

Univariate analysis of GPEP profiles of the patient samples described above independently and accurately predicted response to irinotecan therapy ($p<0.0001$); late recurrence (LRec, $p<0.0005$); and disease-related death (DRD, $p<0.0001$). When stratified into GPEP negative, borderline positive and highly positive groups, patients with highly positive tumors had a relative risk (adjusted relative hazard) of irinotecan therapy response of 8.3 (range 2.1-32.4); LRec of 4.3 (range 1.7-11.0) and DRD of 11.0 (range 3.0-40.7). Tumor size and histologic grade did not predict irinotecan therapy response, LRec or DRD.

The results from this study demonstrate that in late stage colon cancer patients, GPEP positivity by immunohistochemistry accurately predicted irinotecan therapy response, late disease recurrence and disease related death independent of tumor size, grade and Duke's status. The test accurately detected ninety-two percent (92%) of non-responders to irinotecan therapy (less than 1.5% error rate or mis-classification). For determining irinotecan responsiveness, the test sensitivity rate was determined to be about ninety-six percent (96%), and the test specificity rate to be about ninety-eight percent (98%). "GPEP positivity" means that in the tumor samples from patients who were responders to irinotecan therapy, the following proteins were up-regulated: ERBB2, GRB7, JNK1 kinase, BCL2, MK167, phospho-Akt, CD-68 and BAG1, and the following genes and encoded proteins were down-regulated: Erk1 kinase, phospho-GSK-3beta, MMP11, CTSL2, CCNB1, BIRC5, STK6, MRP14 and GSTM1, compared with expression of these genes and proteins in normal colon tissue from these patients and the normal colon tissue and non-colon cancer tissues from other patients. Reference proteins ACTB, GAPD, GUSB, RPLP0 and TFRC were up-regulated in all tissues.

The results from this study are illustrated in FIG. 1. FIG. 1 is a graph showing the survival rates of colorectal cancer patients treated with irinotecan plotted against the presence of a GPEP of the invention. As shown in FIG. 1, patients with tumors having a gene expression profile in which at least sixteen of the genes in the present GPEP were differentially expressed and had the longest survival rates after treatment with irinotecan. Patients whose gene expression profile showed that ten or more of the genes in the GPEP had the next longest survival rates. The survival rates of patients whose gene expression profiles indicated that four or fewer of these genes were differentially expressed had the lowest survival rates after irinotecan therapy.

The twenty genes noted in the legend to FIG. 1 include five reference proteins.

Validation Studies

Studies using additional colon cancer biopsy tissues (from patients other than those used in the study described above) were performed to further validate the utility of the GPEP of the present invention in predicting a patient's responsiveness to irinotecan therapy. In one such study, formalin fixed paraffin embedded primary colon cancer specimens from 220 patients followed for a minimum of 120 months were evaluated for primary tumor size, histologic grade, Duke's status and expression of the proteins in the present GPEP. None of these patients received adjuvant treatment prior to the first episode of disease recurrence. The study was carried out using the same IHC methodology as described in the preceding Example, and using the same negative and positive control arrays.

Univariate analysis of GPEP profiles of the patient samples described above accurately predicted response to irinotecan therapy ($p<0.0001$); late recurrence (LRec, $p<0.0005$); and disease-related death (DRD, $p<0.0001$). When stratified into GPEP negative, borderline positive and highly positive groups, patients with highly positive tumors had a relative risk (adjusted relative hazard) of irinotecan therapy response of 6.7 (range 2.1-22.4); LRec of 3.3 (range 1.7-9.0) and DRD of 7.0 (range 3.0-30.0).

The results from this study further validates that in late stage colon cancer patients, GPEP positivity accurately predicted irinotecan therapy response, late disease recurrence and disease related death independent of tumor size, grade and Duke's status. For determining irinotecan responsiveness, the test sensitivity rate was determined to be about ninety-six percent (96%), and the test specificity rate to be about ninety-eight percent (98%).

What is claimed is:

1. An assay for determining if a patient diagnosed with colon cancer is a responder to treatment with irinotecan comprising (a) a means for determining expression levels in a tumor cell or tumor tissue, a sample which has been mounted in a tissue microarray (TMA), from the patient of each of ERBB2 consisting of the amino acid sequence of SEQ ID NO. 23, GRB7 consisting of the amino acid sequence of SEQ ID NO. 24, JNK1 kinase consisting of the amino acid sequence of SEQ ID NO. 26, BCL2 consisting of the amino acid sequence of SEQ ID NO. 27, MK167 consisting of the amino acid sequence of SEQ ID NO. 33, phospho-Akt consisting of the amino acid sequence of SEQ ID NO. 35, CD68 consisting of the amino acid sequence of SEQ ID NO. 36, and BAG 1 consisting of the amino acid sequence of SEQ ID NO. 37; wherein the means for determining the expression levels consist of one antibody for each protein; and (b) a system for predicting at least one of response to irinotecan therapy (RR), late recurrence (LRec) or disease-related death (DRD), comprising a database storing information of differential expression of the proteins of (a) in a tumor cell or tumor tissue from the patient as compared to normal colon tissue or cells, along with clinical information of the patient from whom the sample is obtained, an algorithm to correlate the differential expression of proteins to the patient information, and scoring criteria based on total percentage of staining by each antibody.

2. The assay of claim 1 further comprising means for detecting the expression level of at least one reference protein in the cells or tissue of the patient diagnosed with colon cancer.

3. The assay of claim 2 wherein the reference protein is GAPD having the amino acid sequence of SEQ ID NO. 40.

4. The assay of claim 1 further comprising means for determining expression levels in a tumor cell or tumor tissue from the patient of Erk1 kinase consisting of the amino acid sequence of SEQ ID NO. 25, phospho-GSK-3-beta consisting of the amino acid sequence of SEQ ID NO. 28, MMP11 consisting of the amino acid sequence of SEQ ID NO. 29, CTSL2 consisting of the amino acid sequence of SEQ ID NO. 30, CCNBI consisting of the amino acid sequence of SEQ ID NO. 31, BIRC5 consisting of the amino acid sequence of SEQ ID NO. 32, STK6 consisting of the amino acid sequence of SEQ ID NO. 34, MRP14 consisting of the amino acid sequence of SEQ ID NO. 44 or GSTMI consisting of the amino acid sequence of SEQ ID NO. 38.

5. The assay of claim 1, wherein the patient is a responder to treatment with irinotecan if the level of each of ERBB2 consisting of the amino acid sequence of SEQ ID NO. 23, GRB7 consisting of the amino acid sequence of SEQ ID NO. 24, JNK1 kinase consisting of the amino acid sequence of SEQ ID NO. 26, BCL2 consisting of the amino acid sequence of SEQ ID NO. 27, MK167 consisting of the amino acid sequence of SEQ ID NO. 33, phospho-Akt consisting of the amino acid sequence of SEQ ID NO. 35, CD68 consisting of the amino acid sequence of SEQ ID NO. 36 and BAG1 consisting of the amino acid sequence of SEQ ID NO. 37, is elevated in the tissue or cells as compared to the corresponding levels in normal colon tissue or cells.

6. The assay of claim 4, wherein the patient is a responder to treatment with irinotecan if the level of Erk1 kinase consisting of the amino acid sequence of SEQ ID NO. 25, phospho-GSK-3-beta consisting of the amino acid sequence of SEQ ID NO. 28, MMP11 consisting of the amino acid sequence of SEQ ID NO. 29, CTSL2 consisting of the amino acid sequence of SEQ ID NO. 30, CCNB1 consisting of the amino acid sequence of SEQ ID NO. 31, BIRC5 consisting of the amino acid sequence of SEQ ID NO. 32, STK6 consisting of the amino acid sequence of SEQ ID NO. 34, MRP14 consisting of the amino acid sequence of SEQ ID NO. 44, or GSTM1 consisting of the amino acid sequence of SEQ ID NO. 38, is lower in the tissue or cells as compared to the corresponding levels in normal colon tissue or cells.

7. The assay of claim 4, wherein the patient is a responder to treatment with irinotecan if the level of each of ERBB2 consisting of the amino acid sequence of SEQ ID NO. 23, GRB7 consisting of the amino acid sequence of SEQ ID NO. 24, JNK1 kinase consisting of the amino acid sequence of SEQ ID NO. 26, BCL2 consisting of the amino acid sequence of SEQ ID NO. 27, MK167 consisting of the amino acid sequence of SEQ ID NO. 33, phospho-Akt consisting of the amino acid sequence of SEQ ID NO. 35, CD68 consisting of the amino acid sequence of SEQ ID NO. 36 and BAG1 consisting of the amino acid sequence of SEQ ID NO. 37, is elevated in the tissue or cells as compared to the corresponding levels in normal colon tissue or cells, and if the level of Erk1 kinase consisting of the amino acid sequence of SEQ ID NO. 25, phospho-GSK-3-beta consisting of the amino acid sequence of SEQ ID NO. 28, MMP11 consisting of the amino acid sequence of SEQ ID NO. 29, CTSL2 consisting of the amino acid sequence of SEQ ID NO. 30, CCNB1 consisting of the amino acid sequence of SEQ ID NO. 31, BIRC5 consisting of the amino acid sequence of SEQ ID NO. 32, STK6 consisting of the amino acid sequence of SEQ ID NO. 34, MRP14 consisting of the amino acid sequence of SEQ ID NO. 44, or GSTM1 consisting of the amino acid sequence of SEQ ID NO. 38, is lower in the tissue or cells as compared to the corresponding levels in normal colon tissue or cells.

8. An assay for determining if a patient diagnosed with colon cancer is a responder to treatment with irinotecan consisting of (a) a means for determining expression levels in a tumor cell or tumor tissue from the patient of each of Erk1 kinase consisting of the amino acid sequence of SEQ ID NO. 25, phospho-GSK-3-beta consisting of the amino acid sequence of SEQ ID NO. 28, MMP11 consisting of the amino acid sequence of SEQ ID NO. 29, CTSL2 consisting of the amino acid sequence of SEQ ID NO. 30, CCNBI consisting of the amino acid sequence of SEQ ID NO. 31, BIRC5 consisting of the amino acid sequence of SEQ ID NO. 32, STK6 consisting of the amino acid sequence of SEQ ID NO. 34, MRP14 consisting of the amino acid sequence of SEQ ID NO. 44 and GSTMI consisting of the amino acid sequence of SEQ ID NO. 38, wherein the means for determining the expression levels consist of one antibody for each protein; and (b) a system for predicting at least one of response to irinotecan therapy (RR), late recurrence (LRec) or disease-related death (DRD), comprising a database storing information of differential expression of the proteins of (a) in a tumor cell or tumor tissue from the patient as compared to normal colon tissue or cells, along with clinical information of the patient from whom the sample is obtained, an algorithm to correlate the differential expression of proteins to the patient information, and scoring criteria based on total percentage of staining by each antibody.

9. The assay of claim 8, wherein the patient is a responder to treatment with irinotecan if the level of each of Erk1 kinase consisting of the amino acid sequence of SEQ ID NO. 25, phospho-GSK-3-beta consisting of the amino acid sequence of SEQ ID NO. 28, MMP11 consisting of the amino acid sequence of SEQ ID NO. 29, CTSL2 consisting of the amino acid sequence of SEQ ID NO. 30, CCNB1 consisting of the amino acid sequence of SEQ ID NO. 31, BIRC5 consisting of the amino acid sequence of SEQ ID NO. 32, STK6 consisting of the amino acid sequence of SEQ ID NO. 34, MRP14 consisting of the amino acid sequence of SEQ ID NO. 44, and GSTM1 consisting of the amino acid sequence of SEQ ID NO. 38, is lower in the tissue or cells as compared to the corresponding levels in normal colon tissue or cells.

10. The assay of claim 1 wherein each antibody has a detectable label.

11. The assay of claim 1 further comprising a secondary antibody.

12. The assay of claim 11 wherein the secondary antibody is a biotinylated secondary antibody.

13. The assay of claim 12 further comprising peroxidase labeled streptavidin.

* * * * *

SEQUENCE LISTING

<160> NUMBER OF SEQ ID NOS: 44

<210> SEQ ID NO 1
<211> LENGTH: 8704
<212> TYPE: DNA
<213> ORGANISM: Homo sapiens

<400> SEQUENCE: 1
ggaggaggtg gaggaggagg gctgcttgag gaagtataag aatgaagttg tgaagctgag 60
attcccctcc attgggaccg gagaaaccag gggagccccc cgggcagccg cgcgcccctt 120
cccacggggc cctttactgc gccgcgcgcc cggcccccac ccctcgcagc accccgcgcc 180
ccgcgccctc ccagccgggt ccagccggag ccatggggcc ggagccgcag tgagcaccat 240
ggagctggcg gccttgtgcc gctgggggct cctcctcgcc ctcttgcccc ccggagccgc 300
gagcacccaa gtgtgcaccg gcacagacat gaagctgcgg ctccctgcca gtcccgagac 360
ccacctggac atgctccgcc acctctacca gggctgccag gtggtgcagg gaaacctgga 420
actcacctac ctgcccacca atgccagcct gtccttcctg caggatatcc aggaggtgca 480
gggctacgtg ctcatcgctc acaaccaagt gaggcaggtc ccactgcaga ggctgcggat 540
tgtgcgaggc acccagctct ttgaggacaa ctatgccctg gccgtgctag acaatggaga 600
cccgctgaac aataccaccc ctgtcacagg ggcctcccca ggaggcctgc gggagctgca 660
gcttcgaagc ctcacagaga tcttgaaagg aggggtcttg atccagcgga acccccagct 720
ctgctaccag gacacgattt tgtggaagga catcttccac aagaacaacc agctggctct 780
cacactgata gacaccaacc gctctcgggc ctgccacccc tgttctccga tgtgtaaggg 840
ctcccgctgc tggggagaga gttctgagga ttgtcagagc ctgacgcgca ctgtctgtgc 900
cggtggctgt gcccgctgca aggggccact gcccactgac tgctgccatg agcagtgtgc 960
tgccggctgc acgggcccca agcactctga ctgcctggcc tgcctccact tcaaccacag 1020
tggcatctgt gagctgcact gcccagccct ggtcacctac aacacagaca cgtttgagtc 1080
catgcccaat cccgagggcc ggtatacatt cggcgccagc tgtgtgactg cctgtcccta 1140
caactacctt tctacggacg tgggatcctg caccctcgtc tgccccctgc acaaccaaga 1200
ggtgacagca gaggatggaa cacagcggtg tgagaagtgc agcaagccct gtgcccgagt 1260
gtgctatggt ctgggcatgg agcacttgcg agaggtgagg gcagttacca gtgccaatat 1320
ccaggagttt gctggctgca agaagatctt tgggagcctg gcatttctgc cggagagctt 1380
tgatggggac ccagcctcca acactgcccc gctccagcca gagcagctcc aagtgtttga 1440
gactctggaa gagatcacag gttacctata catctcagca tggccggaca gcctgcctga 1500
cctcagcgtc ttccagaacc tgcaagtaat ccggggacga attctgcaca atggcgccta 1560
ctcgctgacc ctgcaagggc tgggcatcag ctggctgggg ctgcgctcac tgagggaact 1620
gggcagtgga ctggccctca tccaccataa cacccacctc tgcttcgtgc acacggtgcc 1680
ctgggaccag ctctttcgga acccgcacca agctctgctc cacactgcca accggccaga 1740
ggacgagtgt gtgggcgagg gcctggcctg ccaccagctg tgcgcccgag ggcactgctg 1800
gggtccaggg cccacccagt gtgtcaactg cagccagttc cttcggggcc aggagtgcgt 1860
ggaggaatgc cgagtactgc aggggctccc cagggagtat gtgaatgcca ggcactgttt 1920
gccgtgccac cctgagtgtc agccccagaa tggctcagtg acctgttttg gaccggaggc 1980
tgaccagtgt gtggcctgtg cccactataa ggaccctccc ttctgcgtgg cccgctgccc 2040

-continued

```
cagcggtgtg aaacctgacc tctcctacat gcccatctgg aagtttccag atgaggaggg   2100
cgcatgccag ccttgcccca tcaactgcac ccactcctgt gtggacctgg atgacaaggg   2160
ctgccccgcc gagcagagag ccagccctct gacgtccatc atctctgcgg tggttggcat   2220
tctgctggtc gtggtcttgg gggtggtctt tgggatcctc atcaagcgac ggcagcagaa   2280
gatccggaag tacacgatgc ggagactgct gcaggaaacg gagctggtgg agccgctgac   2340
acctagcgga gcgatgccca accaggcgca gatgcggatc ctgaaagaga cggagctgag   2400
gaaggtgaag gtgcttggat ctggcgcttt tggcacagtc tacaagggca tctggatccc   2460
tgatggggag aatgtgaaaa ttccagtggc catcaaagtg ttgagggaaa acacatcccc   2520
caaagccaac aaagaaatct tagacgaagc atacgtgatg gctggtgtgg gctccccata   2580
tgtctcccgc cttctgggca tctgcctgac atccacggtg cagctggtga cacagcttat   2640
gccctatggc tgcctcttag accatgtccg ggaaaaccgc ggacgcctgg gctcccagga   2700
cctgctgaac tggtgtatgc agattgccaa ggggatgagc tacctggagg atgtgcggct   2760
cgtacacagg gacttggccg ctcggaacgt gctggtcaag agtcccaacc atgtcaaaat   2820
tacagacttc gggctggctc ggctgctgga cattgacgag acagagtacc atgcagatgg   2880
gggcaaggtg cccatcaagt ggatggcgct ggagtccatt ctccgccggc ggttcaccca   2940
ccagagtgat gtgtggagtt atggtgtgac tgtgtgggag ctgatgactt ttggggccaa   3000
accttacgat gggatcccag cccgggagat ccctgacctg ctggaaaagg gggagcggct   3060
gccccagccc cccatctgca ccattgatgt ctacatgatc atggtcaaat gttggatgat   3120
tgactctgaa tgtcggccaa gattccggga gttggtgtct gaattctccc gcatggccag   3180
ggacccccag cgctttgtgg tcatccagaa tgaggacttg ggcccagcca gtcccttgga   3240
cagcaccttc taccgctcac tgctggagga cgatgacatg gggggacctgg tggatgctga   3300
ggagtatctg gtaccccagc agggcttctt ctgtccagac cctgccccgg gcgctggggg   3360
catggtccac cacaggcacc gcagctcatc taccaggagt ggcggtgggg acctgacact   3420
agggctggag ccctctgaag aggaggcccc caggtctcca ctggcaccct ccgaaggggc   3480
tggctccgat gtatttgatg gtgacctggg aatgggggca gccaaggggc tgcaaagcct   3540
ccccacacat gaccccagcc ctctacagcg gtacagtgag gaccccacag tacccctgcc   3600
ctctgagact gatggctacg ttgccccct gacctgcagc cccagcctg aatatgtgaa   3660
ccagccagat gttcggcccc agcccccttc gccccgagag ggccctctgc ctgctgcccg   3720
acctgctggt gccactctgg aaaggcccaa gactctctcc ccagggaaga atggggtcgt   3780
caaagacgtt tttgcctttg gggtgccgt ggagaacccc gagtacttga caccccaggg   3840
aggagctgcc cctcagcccc accctcctcc tgccttcagc ccagccttcg acaacctcta   3900
ttactgggac caggacccac cagagcgggg ggctccaccc agcaccttca aagggacacc   3960
tacggcagag aacccagagt acctgggtct ggacgtgcca gtgtgaacca gaaggccaag   4020
tccgcagaag ccctgatgtg tcctcaggga gcagggaagg cctgacttct gctggcatca   4080
ggaggaggtg gaggaggagg gctgcttgag gaagtataag aatgaagttg tgaagctgag   4140
attcccctcc attgggaccg gagaaaccag gggagccccc cgggcagccg cgcgcccctt   4200
cccacggggc cctttactgc gccgcgcgcc cggcccccac ccctcgcagc accccgcgcc   4260
ccgcgccctc ccagccgggt ccagccggag ccatggggcc ggagccgcag tgagcaccat   4320
ggagctggcg gccttgtgcc gctgggggct cctcctcgcc ctcttgcccc ccggagccgc   4380
gagcacccaa gtgtgcaccg gcacagacat gaagctgcgg ctccctgcca gtcccgagac   4440
```

-continued

```
ccacctggac atgctccgcc acctctacca gggctgccag gtggtgcagg gaaacctgga   4500

actcacctac ctgcccacca atgccagcct gtccttcctg caggatatcc aggaggtgca   4560

gggctacgtg ctcatcgctc acaaccaagt gaggcaggtc ccactgcaga ggctgcggat   4620

tgtgcgaggc acccagctct ttgaggacaa ctatgccctg gccgtgctag acaatggaga   4680

cccgctgaac aataccaccc ctgtcacagg ggcctcccca ggaggcctgc gggagctgca   4740

gcttcgaagc ctcacagaga tcttgaaagg aggggtcttg atccagcgga acccccagct   4800

ctgctaccag gacacgattt tgtggaagga catcttccac aagaacaacc agctggctct   4860

cacactgata gacaccaacc gctctcgggc ctgccacccc tgttctccga tgtgtaaggg   4920

ctcccgctgc tggggagaga gttctgagga ttgtcagagc ctgacgcgca ctgtctgtgc   4980

cggtggctgt gcccgctgca aggggccact gcccactgac tgctgccatg agcagtgtgc   5040

tgccggctgc acgggcccca agcactctga ctgcctggcc tgcctccact tcaaccacag   5100

tggcatctgt gagctgcact gcccagccct ggtcacctac aacacagaca cgtttgagtc   5160

catgcccaat cccgagggcc ggtatacatt cggcgccagc tgtgtgactg cctgtcccta   5220

caactacctt tctacggacg tggatcctg caccctcgtc tgccccctgc acaaccaaga   5280

ggtgacagca gaggatggaa cacagcggtg tgagaagtgc agcaagccct gtgcccgagt   5340

gtgctatggt ctgggcatgg agcacttgcg agaggtgagg gcagttacca gtgccaatat   5400

ccaggagttt gctggctgca agaagatctt tgggagcctg gcatttctgc cggagagctt   5460

tgatggggac ccagcctcca acactgcccc gctccagcca gagcagctcc aagtgtttga   5520

gactctggaa gagatcacag gttacctata catctcagca tggccggaca gcctgcctga   5580

cctcagcgtc ttccagaacc tgcaagtaat ccggggacga attctgcaca atggcgccta   5640

ctcgctgacc ctgcaagggc tgggcatcag ctggctgggg ctgcgctcac tgagggaact   5700

gggcagtgga ctggccctca tccaccataa cacccacctc tgcttcgtgc acacggtgcc   5760

ctgggaccag ctctttcgga acccgcacca agctctgctc cacactgcca accggccaga   5820

ggacgagtgt gtgggcgagg gcctggcctg ccaccagctg tgcgcccgag ggcactgctg   5880

gggtccaggg cccacccagt gtgtcaactg cagccagttc cttcggggcc aggagtgcgt   5940

ggaggaatgc cgagtactgc aggggctccc cagggagtat gtgaatgcca ggcactgttt   6000

gccgtgccac cctgagtgtc agccccagaa tggctcagtg acctgttttg gaccggaggc   6060

tgaccagtgt gtggcctgtg cccactataa ggaccctccc ttctgcgtgg cccgctgccc   6120

cagcggtgtg aaacctgacc tctcctacat gcccatctgg aagtttccag atgaggaggg   6180

cgcatgccag ccttgcccca tcaactgcac ccactcctgt gtggacctgg atgacaaggg   6240

ctgccccgcc gagcagagag ccagccctct gacgtccatc atctctgcgg tggttggcat   6300

tctgctggtc gtggtcttgg gggtggtctt tgggatcctc atcaagcgac ggcagcagaa   6360

gatccggaag tacacgatgc ggagactgct gcaggaaacg gagctggtgg agccgctgac   6420

acctagcgga gcgatgccca accaggcgca gatgcggatc ctgaaagaga cggagctgag   6480

gaaggtgaag gtgcttggat ctggcgcttt tggcacagtc tacaagggca tctggatccc   6540

tgatggggag aatgtgaaaa ttccagtggc catcaaagtg ttgagggaaa acacatcccc   6600

caaagccaac aaagaaatct tagacgaagc atacgtgatg gctggtgtgg gctccccata   6660

tgtctcccgc cttctgggca tctgcctgac atccacggtg cagctggtga cacagcttat   6720

gccctatggc tgcctcttag accatgtccg ggaaaaccgc ggacgcctgg gctcccagga   6780

cctgctgaac tggtgtatgc agattgccaa ggggatgagc tacctggagg atgtgcggct   6840
```

-continued

```
cgtacacagg gacttggccg ctcggaacgt gctggtcaag agtcccaacc atgtcaaaat   6900

tacagacttc gggctggctc ggctgctgga cattgacgag acagagtacc atgcagatgg   6960

gggcaaggtg cccatcaagt ggatggcgct ggagtccatt ctccgccggc ggttcaccca   7020

ccagagtgat gtgtggagtt atggtgtgac tgtgtgggag ctgatgactt ttggggccaa   7080

accttacgat gggatcccag cccgggagat ccctgacctg ctggaaaagg gggagcggct   7140

gccccagccc cccatctgca ccattgatgt ctacatgatc atggtcaaat gttggatgat   7200

tgactctgaa tgtcggccaa gattccggga gttggtgtct gaattctccc gcatggccag   7260

ggacccccag cgctttgtgg tcatccagaa tgaggacttg ggcccagcca gtcccttgga   7320

cagcaccttc taccgctcac tgctggagga cgatgacatg ggggacctgg tggatgctga   7380

ggagtatctg gtaccccagc agggcttctt ctgtccagac cctgccccgg gcgctggggg   7440

catggtccac cacaggcacc gcagctcatc taccaggagt ggcggtgggg acctgacact   7500

agggctggag ccctctgaag aggaggcccc caggtctcca ctggcaccct ccgaaggggc   7560

tggctccgat gtatttgatg gtgacctggg aatgggggca gccaaggggc tgcaaagcct   7620

ccccacacat gaccccagcc ctctacagcg gtacagtgag gaccccacag taccccctgcc   7680

ctctgagact gatggctacg ttgccccct gacctgcagc cccagcctg aatatgtgaa   7740

ccagccagat gttcggcccc agccccttc gccccgagag ggccctctgc ctgctgcccg   7800

acctgctggt gccactctgg aaaggcccaa gactctctcc ccagggaaga atggggtcgt   7860

caaagacgtt tttgcctttg gggtgccgt ggagaacccc gagtacttga cacccccaggg   7920

aggagctgcc cctcagcccc accctcctcc tgccttcagc ccagccttcg acaacctcta   7980

ttactgggac caggacccac cagagcgggg ggctccaccc agcaccttca aagggacacc   8040

tacggcagag aacccagagt acctgggtct ggacgtgcca gtgtgaacca gaaggccaag   8100

tccgcagaag ccctgatgtg tcctcaggga gcagggaagg cctgacttct gctggcatca   8160

agaggtggga gggccctccg accacttcca ggggaacctg ccatgccagg aacctgtcct   8220

aaggaacctt ccttcctgct tgagttccca gatggctgga aggggtccag cctcgttgga   8280

agaggaacag cactggggag tctttgtgga ttctgaggcc ctgcccaatg agactctagg   8340

gtccagtgga tgccacagcc cagcttggcc ctttccttcc agatcctggg tactgaaagc   8400

cttagggaag ctggcctgag aggggaagcg gccctaaggg agtgtctaag aacaaaagcg   8460

acccattcag agactgtccc tgaaacctag tactgccccc catgaggaag gaacagcaat   8520

ggtgtcagta tccaggcttt gtacagagtg cttttctgtt tagtttttac tttttttgtt   8580

ttgtttttt aaagatgaaa taaagaccca gggggagaat gggtgttgta tggggaggca   8640

agtgtggggg gtccttctcc acacccactt tgtccatttg caaatatatt ttggaaaaca   8700

gcta                                                                  8704
```

<210> SEQ ID NO 2
<211> LENGTH: 2260
<212> TYPE: DNA
<213> ORGANISM: Homo sapiens

<400> SEQUENCE: 2

```
ttttagtttc cttgggcctg gaatctggac acacagggct ccccccgcc tctgacttct     60

ctgtccgaag tcgggacacc ctcctaccac ctgtagagaa gcgggagtgg atctgaaata    120

aaatccagga atctgggggt tcctagacgg agccagactt cggaacgggt gtcctgctac    180

tcctgctggg gctcctccag gacaagggca cacaactggt tccgttaagc ccctctcttg    240
```

-continued

```
ctcagacgcc atggagctgg atctgtctcc acctcatctt agcagctctc cggaagacct    300

ttgcccagcc cctgggaccc ctcctgggac tccccggccc cctgataccc ctctgcctga    360

ggaggtaaag aggtcccagc ctctcctcat cccaaccacc ggcaggaaac ttcgagagga    420

ggagaggcgt gccacctccc tcccctctat ccccaacccc ttccctgagc tctgcagtcc    480

tccctcacag agcccaattc tcgggggccc ctccagtgca agggggctgc tccccgcga     540

tgccagccgc cccatgtag taaaggtgta cagtgaggat ggggcctgca ggtctgtgga     600

ggtggcagca ggtgccacag ctcgccacgt gtgtgaaatg ctggtgcagc gagctcacgc    660

cttgagcgac gagacctggg ggctggtgga gtgccacccc cacctagcac tggagcgggg    720

tttggaggac cacgagtccg tggtggaagt gcaggctgcc tggcccgtgg gcggagatag    780

ccgcttcgtc ttccggaaaa acttcgccaa gtacgaactg ttcaagagct ccccacactc    840

cctgttccca gaaaaaatgg tctccagctg tctcgatgca cacactggta tatcccatga    900

agacctcatc cagaacttcc tgaatgctgg cagctttcct gagatccagg gctttctgca    960

gctgcggggt tcaggacgga agctttggaa acgcttttc tgcttcttgc gccgatctgg    1020

cctctattac tccaccaagg gcacctctaa ggatccgagg cacctgcagt acgtggcaga    1080

tgtgaacgag tccaacgtgt acgtggtgac gcagggccgc aagctctacg ggatgcccac    1140

tgacttcggt ttctgtgtca agcccaacaa gcttcgaaat ggccacaagg ggcttcggat    1200

cttctgcagt gaagatgagc agagccgcac ctgctggctg gctgccttcc gcctcttcaa    1260

gtacggggtg cagctgtaca agaattacca gcaggcacag tctcgccatc tgcatccatc    1320

ttgtttgggc tccccaccct tgagaagtgc ctcagataat accctggtgg ccatggactt    1380

ctctggccat gctgggcgtg tcattgagaa cccccgggag gctctgagtg tggccctgga    1440

ggaggcccag gcctggagga agaagacaaa ccaccgcctc agcctgccca tgccagcctc    1500

cggcacgagc ctcagtgcag ccatccaccg cacccaactc tggttccacg ggcgcatttc    1560

ccgtgaggag agccagcggc ttattggaca gcagggcttg gtagacggcc tgttcctggt    1620

ccgggagagt cagcggaacc cccagggctt tgtcctctct ttgtgccacc tgcagaaagt    1680

gaagcattat ctcatcctgc cgagcgagga ggagggccgc ctgtacttca gcatggatga    1740

tggccagacc cgcttcactg acctgctgca gctcgtggag ttccaccagc tgaaccgcgg    1800

catcctgccg tgcttgctgc gccattgctg cacgcgggtg gccctctgac caggccgtgg    1860

actggctcat gcctcagccc gccttcaggc tgcccgccgc ccctccaccc atccagtgga    1920

ctctggggcg cggccacagg ggacgggatg aggagcggga gggttccgcc actccagttt    1980

tctcctctgc ttctttgcct ccctcagata gaaaacagcc cccactccag tccactcctg    2040

acccctctcc tcaagggaag gccttgggtg gccccctctc cttctcctag ctctggaggt    2100

gctgctctag ggcagggaat tatgggagaa gtgggggcag cccaggcggt ttcacgcccc    2160

acactttgta cagaccgaga ggccagttga tctgctctgt tttatactag tgacaataaa    2220

gattattttt tgatacaaaa aaaaaaaaaa aaaaaaaaaa                          2260
```

<210> SEQ ID NO 3
<211> LENGTH: 1866
<212> TYPE: DNA
<213> ORGANISM: Homo sapiens

<400> SEQUENCE: 3

```
cgttcctcgg cgccgccggg gccccagagg gcagcggcag caacagcagc agcagcagca     60

gcgggagtgg agatggcggc ggcggcggct caggggggcg ggggcgggga gccccgtaga    120
```

-continued accgaggggg tcggcccggg ggtcccgggg gaggtggaga tggtgaaggg gcagccgttc 180
gacgtgggcc cgcgctacac gcagttgcag tacatcggcg agggcgcgta cggcatggtc 240
agctcggcct atgaccacgt gcgcaagact cgcgtggcca tcaagaagat cagccccttc 300
gaacatcaga cctactgcca gcgcacgctc cgggagatcc agatcctgct gcgcttccgc 360
catgagaatg tcatcggcat ccgagacatt ctgcgggcgt ccaccctgga agccatgaga 420
gatgtctaca ttgtgcagga cctgatggag actgacctgt acaagttgct gaaaagccag 480
cagctgagca atgaccatat ctgctacttc ctctaccaga tcctgcgggg cctcaagtac 540
atccactccg ccaacgtgct ccaccgagat ctaaagccct ccaacctgct cagcaacacc 600
acctgcgacc ttaagatttg tgatttcggc ctggcccgga ttgccgatcc tgagcatgac 660
cacaccggct tcctgacgga gtatgtggct acgcgctggt accgggcccc agagatcatg 720
ctgaactcca agggctatac caagtccatc gacatctggt ctgtgggctg cattctggct 780
gagatgctct ctaaccggcc catcttccct ggcaagcact acctggatca gctcaaccac 840
attctgggca tcctgggctc cccatcccag gaggacctga attgtatcat caacatgaag 900
gcccgaaact acctacagtc tctgccctcc aagaccaagg tggcttgggc caagcttttc 960
cccaagtcag actccaaagc ccttgacctg ctggaccgga tgttaacctt taaccccaat 1020
aaacggatca cagtggagga agcgctggct caccccctacc tggagcagta ctatgacccg 1080
acggatgagc cagtggccga ggagcccttc accttcgcca tggagctgga tgacctacct 1140
aaggagcggc tgaaggagct catcttccag gagacagcac gcttccagcc cggagtgctg 1200 gaggcccccct agcccagaca gacatctctg caccctgggg cctggacctg cctcctgcct 1260
gcccctctcc cgccagactg ttagaaaatg gacactgtgc ccagcccgga ccttggcagc 1320
ccaggccggg gtggagcatg ggcctggcca cctctctcct ttgctgaggc ctccagcttc 1380
aggcaggcca aggccttctc ctccccaccc gccctcccca cggggcctcg ggagctcagg 1440
tggccccagt tcaatctccc gctgctgctg ctgctgcgcc cttaccttcc ccagcgtccc 1500
agtctctggc agttctggaa tggaagggtt ctggctgccc caacctgctg aagggcagag 1560
gtggagggtg gggggcgctg agtagggact cagggccatg cctgcccccc tcatctcatt 1620
caaaccccac cctagtttcc ctgaaggaac attccttagt ctcaagggct agcatccctg 1680
aggagccagg ccgggccgaa tcccctccct gtcaaagctg tcacttcgcg tgccctcgct 1740
gcttctgtgt gtggtgagca gaagtggagc tggggggcgt ggagagcccg gcgcccctgc 1800
cacctccctg acccgtctaa tatataaata tagagatgtg tctatggctg aaaaaaaaaa 1860
aaaaaa 1866

<210> SEQ ID NO 4
<211> LENGTH: 1417
<212> TYPE: DNA
<213> ORGANISM: Homo sapiens

<400> SEQUENCE: 4
attaattgct tgccatcatg agcagaagca agcgtgacaa caatttttat agtgtagaga 60
ttggagattc tacattcaca gtcctgaaac gatatcagaa tttaaaacct ataggctcag 120
gagctcaagg aatagtatgc gcagcttatg atgccattct tgaaagaaat gttgcaatca 180
agaagctaag ccgaccattt cagaatcaga ctcatgccaa gcgggcctac agagagctag 240
ttcttatgaa atgtgttaat cacaaaaata taattggcct tttgaatgtt ttcacaccac 300
agaaatccct agaagaattt caagatgttt acatagtcat ggagctcatg gatgcaaatc 360

-continued

```
tttgccaagt gattcagatg gagctagatc atgaaagaat gtcctacctt ctctatcaga    420
tgctgtgtgg aatcaagcac cttcattctg ctggaattat tcatcgggac ttaaagccca    480
gtaatatagt agtaaaatct gattgcactt tgaagattct tgacttcggt ctggccagga    540
ctgcaggaac gagttttatg atgacgcctt atgtagtgac tcgctactac agagcacccg    600
aggtcatcct tggcatgggc tacaaggaaa acgtggattt atggtctgtg ggtgcatta    660
tgggagaaat ggtttgccac aaaatcctct ttccaggaag ggactatatt gatcagtgga    720
ataaagttat tgaacagctt ggaacaccat gtcctgaatt catgaagaaa ctgcaaccaa    780
cagtaaggac ttacgttgaa aacagaccta aatatgctgg atatagcttt gagaaactct    840
tccctgatgt ccttttccca gctgactcag aacacaacaa acttaaagcc agtcaggcaa    900
gggatttgtt atccaaaatg ctggtaatag atgcatctaa aaggatctct gtagatgaag    960
ctctccaaca cccgtacatc aatgtctggt atgatccttc tgaagcagaa gctccaccac   1020
caaagatccc tgacaagcag ttagatgaaa gggaacacac aatagaagag tggaaagaat   1080
tgatatataa ggaagttatg gacttggagg agagaaccaa gaatggagtt atacgggggc   1140
agccctctcc tttagcacag gtgcagcagt gatcaatggc tctcagcatc catcatcatc   1200
gtcgtctgtc aatgatgtgt cttcaatgtc aacagatccg actttggcct ctgatacaga   1260
cagcagtcta gaagcagcag ctgggcctct gggctgctgt agatgactac ttgggccatc   1320
ggggggtggg agggatgggg agtcggttag tcattgatag aactactttg aaaacaattc   1380
agtggtctta tttttgggtg atttttcaaa aaatgta                            1417
```

<210> SEQ ID NO 5
<211> LENGTH: 6492
<212> TYPE: DNA
<213> ORGANISM: Homo sapiens

<400> SEQUENCE: 5

```
tttctgtgaa gcagaagtct gggaatcgat ctggaaatcc tcctaatttt tactccctct     60
ccccgcgact cctgattcat tgggaagttt caaatcagct ataactggag agtgctgaag    120
attgatggga tcgttgcctt atgcatttgt tttggtttta caaaaaggaa acttgacaga    180
ggatcatgct gtacttaaaa aatacaacat cacagaggaa gtagactgat attaacaata    240
cttactaata ataacgtgcc tcatgaaata aagatccgaa aggaattgga ataaaaattt    300
cctgcatctc atgccaaggg ggaaacacca gaatcaagtg ttccgcgtga ttgaagacac    360
cccctcgtcc aagaatgcaa agcacatcca ataaaaatagc tggattataa ctcctcttct    420
ttctctgggg gccgtggggt gggagctggg gcgagaggtg ccgttggccc ccgttgcttt    480
tcctctggga aggatggcgc acgctgggag aacagggtac gataaccggg agatagtgat    540
gaagtacatc cattataagc tgtcgcagag ggctacgag tgggatgcgg gagatgtggg    600
cgccgcgccc ccgggggccg cccccgcacc gggcatcttc tcctcccagc ccgggcacac    660
gccccatcca gccgcatccc gggacccggt cgccaggacc tcgccgctgc agaccccggc    720
tgcccccggc gccgccgcgg ggcctgcgct cagcccggtg ccacctgtgg tccacctgac    780
cctccgccag gccggcgacg acttctcccg ccgctaccgc cgcgacttcg ccgagatgtc    840
cagccagctg cacctgacgc ccttcaccgc gcggggacgc tttgccacgg tggtggagga    900
gctcttcagg gacggggtga actgggggag gattgtggcc ttctttgagt tcggtggggt    960
catgtgtgtg gagagcgtca accgggagat gtcgcccctg gtggacaaca tcgccctgtg   1020
gatgactgag tacctgaacc ggcacctgca cacctggatc caggataacg gaggctggga   1080
```

-continued

```
tgcctttgtg gaactgtacg gccccagcat gcggcctctg tttgatttct cctggctgtc   1140
tctgaagact ctgctcagtt tggccctggt gggagcttgc atcaccctgg gtgcctatct   1200
gggccacaag tgaagtcaac atgcctgccc caaacaaata tgcaaaaggt tcactaaagc   1260
agtagaaata atatgcattg tcagtgatgt accatgaaac aaagctgcag gctgtttaag   1320
aaaaaataac acacatataa acatcacaca cacagacaga cacacacaca cacaacaatt   1380
aacagtcttc aggcaaaacg tcgaatcagc tatttactgc caaagggaaa tatcatttat   1440
tttttacatt attaagaaaa aaagatttat ttatttaaga cagtcccatc aaaactcctg   1500
tctttggaaa tccgaccact aattgccaag caccgcttcg tgtggctcca cctggatgtt   1560
ctgtgcctgt aaacatagat tcgctttcca tgttgttggc cggatcacca tctgaagagc   1620
agacggatgg aaaaaggacc tgatcattgg ggaagctggc tttctggctg ctggaggctg   1680
gggagaaggt gttcattcac ttgcatttct ttgccctggg ggctgtgata ttaacagagg   1740
gagggttcct gtggggggaa gtccatgcct ccctggcctg aagaagagac tctttgcata   1800
tgactcacat gatgcatacc tggtgggagg aaaagagttg ggaacttcag atggacctag   1860
tacccactga gatttccacg ccgaaggaca gcgatgggaa aaatgccctt aaatcatagg   1920
aaagtatttt tttaagctac caattgtgcc gagaaaagca ttttagcaat tttatacaata   1980
tcatccagta ccttaagccc tgattgtgta tattcatata ttttggatac gcacccccca   2040
actcccaata ctggctctgt ctgagtaaga aacagaatcc tctggaactt gaggaagtga   2100
acatttcggt gacttccgca tcaggaaggc tagagttacc cagagcatca ggccgccaca   2160
agtgcctgct tttaggagac cgaagtccgc agaacctgcc tgtgtcccag cttggaggcc   2220
tggtcctgga actgagccgg ggccctcact ggcctcctcc agggatgatc aacagggcag   2280
tgtggtctcc gaatgtctgg aagctgatgg agctcagaat tccactgtca agaaagagca   2340
gtagaggggt gtggctgggc ctgtcaccct ggggccctcc aggtaggccc gttttcacgt   2400
ggagcatggg agccacgacc cttcttaaga catgtatcac tgtagaggga aggaacagag   2460
gccctgggcc cttcctatca gaaggacatg gtgaaggctg ggaacgtgag gagaggcaat   2520
ggccacggcc cattttggct gtagcacatg gcacgttggc tgtgtggcct tggcccacct   2580
gtgagtttaa agcaaggctt taaatgactt tggagagggt cacaaatcct aaaagaagca   2640
ttgaagtgag gtgtcatgga ttaattgacc cctgtctatg gaattacatg taaaacatta   2700
tcttgtcact gtagtttggt tttatttgaa aacctgacaa aaaaaaagtt ccaggtgtgg   2760
aatatggggg ttatctgtac atcctggggc attaaaaaaa aaatcaatgg tggggaacta   2820
taaagaagta acaaaagaag tgacatcttc agcaaataaa ctaggaaatt tttttttctt   2880
ccagtttaga atcagccttg aaacattgat ggaataactc tgtggcatta ttgcattata   2940
taccatttat ctgtattaac tttggaatgt actctgttca atgtttaatg ctgtggttga   3000
tatttcgaaa gctgctttaa aaaaatacat gcatctcagc gtttttttgt ttttaattgt   3060
atttagttat ggcctataca ctatttgtga gcaaaggtga tcgttttctg tttgagattt   3120
ttatctcttg attcttcaaa agcattctga gaaggtgaga taagccctga gtctcagcta   3180
cctaagaaaa acctggatgt cactggccac tgaggagctt tgtttcaacc aagtcatgtg   3240
catttccacg tcaacagaat tgtttattgt gacagttata tctgttgtcc ctttgacctt   3300
gtttcttgaa ggtttcctcg tccctgggca attccgcatt taattcatgg tattcaggat   3360
tacatgcatg tttggttaaa cccatgagat tcattcagtt aaaaatccag atggcaaatg   3420
accagcagat tcaaatctat ggtggtttga cctttagaga gttgctttac gtggcctgtt   3480
```

-continued

```
tcaacacaga cccacccaga gccctcctgc cctccttccg cgggggcttt ctcatggctg   3540
tccttcaggg tcttcctgaa atgcagtggt gcttacgctc caccaagaaa gcaggaaacc   3600
tgtggtatga agccagacct ccccggcggg cctcagggaa cagaatgatc agacctttga   3660
atgattctaa tttttaagca aaatattatt ttatgaaagg tttacattgt caaagtgatg   3720
aatatggaat atccaatcct gtgctgctat cctgccaaaa tcattttaat ggagtcagtt   3780
tgcagtatgc tccacgtggt aagatcctcc aagctgcttt agaagtaaca atgaagaacg   3840
tggacgtttt taatataaag cctgttttgt cttttgttgt tgttcaaacg ggattcacag   3900
agtatttgaa aaatgtatat atattaagag gtcacggggg ctaattgctg gctggctgcc   3960
ttttgctgtg gggttttgtt acctggtttt aataacagta aatgtgccca gcctcttggc   4020
cccagaactg tacagtattg tggctgcact tgctctaaga gtagttgatg ttgcattttc   4080
cttattgtta aaaacatgtt agaagcaatg aatgtatata aaagcctcaa ctagtcattt   4140
ttttctcctc ttcttttttt tcattatatc taattatttt gcagttgggc aacagagaac   4200
catccctatt ttgtattgaa gagggattca catctgcatc ttaactgctc tttatgaatg   4260
aaaaaacagt cctctgtatg tactcctctt tacactggcc agggtcagag ttaaatagag   4320
tatatgcact ttccaaattg gggacaaggg ctctaaaaaa agccccaaaa ggagaagaac   4380
atctgagaac ctcctcggcc ctcccagtcc ctcgctgcac aaatactccg caagagaggc   4440
cagaatgaca gctgacaggg tctatggcca tcgggtcgtc tccgaagatt tggcaggggc   4500
agaaaactct ggcaggctta agatttggaa taaagtcaca gaattaagga agcacctcaa   4560
tttagttcaa acaagacgcc aacattctct ccacagctca cttacctctc tgtgttcaga   4620
tgtggccttc catttatatg tgatctttgt tttattagta aatgcttatc atctaaagat   4680
gtagctctgg cccagtggga aaaattagga agtgattata aatcgagagg agttataata   4740
atcaagatta aatgtaaata atcagggcaa tcccaacaca tgtctagctt tcacctccag   4800
gatctattga gtgaacagaa ttgcaaatag tctctatttg taattgaact tatcctaaaa   4860
caaatagttt ataaatgtga acttaaactc taattaattc caactgtact tttaaggcag   4920
tggctgtttt tagactttct tatcacttat agttagtaat gtacacctac tctatcagag   4980
aaaaacagga aaggctcgaa atacaagcca ttctaaggaa attagggagt cagttgaaat   5040
tctattctga tcttattctg tggtgtcttt tgcagcccag acaaatgtgg ttacacactt   5100
tttaagaaat acaattctac attgtcaagc ttatgaaggt tccaatcaga tctttattgt   5160
tattcaattt ggatctttca gggatttttt ttttaaatta ttatgggaca aaggacattt   5220
gttggagggg tgggagggag gaagaatttt taaatgtaaa acattcccaa gtttggatca   5280
gggagttgga agttttcaga ataaccagaa ctaagggtat gaaggacctg tattggggtc   5340
gatgtgatgc ctctgcgaag aaccttgtgt gacaaatgag aaacattttg aagtttgtgg   5400
tacgaccttt agattccaga gacatcagca tggctcaaag tgcagctccg tttggcagtg   5460
caatggtata aatttcaagc tggatatgtc taatgggtat ttaaacaata aatgtgcagt   5520
tttaactaac aggatattta atgacaacct tctggttggt agggacatct gtttctaaat   5580
gtttattatg tacaatacag aaaaaaattt tataaaatta agcaatgtga aactgaattg   5640
gagagtgata atacaagtcc tttagtctta cccagtgaat cattctgttc catgtctttg   5700
gacaaccatg accttggaca atcatgaaat atgcatctca ctggatgcaa agaaaatcag   5760
atggagcatg aatggtactg taccggttca tctggactgc cccagaaaaa taacttcaag   5820
caaacatcct atcaacaaca aggttgttct gcataccaag ctgagcacag aagatgggaa   5880
```

-continued

```
cactggtgga ggatggaaag gctcgctcaa tcaagaaaat tctgagacta ttaataaata   5940

agactgtagt gtagatactg agtaaatcca tgcacctaaa ccttttggaa aatctgccgt   6000

gggccctcca gatagctcat ttcattaagt ttttccctcc aaggtagaat ttgcaagagt   6060

gacagtggat tgcatttctt ttggggaagc tttcttttgg tggttttgtt tattatacct   6120

tcttaagttt tcaaccaagg tttgcttttg ttttgagtta ctggggttat ttttgtttta   6180

aataaaaata agtgtacaat aagtgttttt gtattgaaag cttttgttat caagattttc   6240

atacttttac cttccatggc tctttttaag attgatactt ttaagaggtg gctgatattc   6300

tgcaacactg tacacataaa aaatacggta aggatacttt acatggttaa ggtaaagtaa   6360

gtctccagtt ggccaccatt agctataatg gcactttgtt tgtgttgttg gaaaaagtca   6420

cattgccatt aaactttcct tgtctgtcta gttaatattg tgaagaaaaa taaagtacag   6480

tgtgagatac tg                                                       6492
```

<210> SEQ ID NO 6
<211> LENGTH: 1639
<212> TYPE: DNA
<213> ORGANISM: Homo sapiens

<400> SEQUENCE: 6

```
atcatctata tgttaaatat ccgtgccgat ctgtcttgaa ggagaaatat atcgcttgtt     60

ttgtttttta tagtatacaa aaggagtgaa aagccaagag gacgaagtct ttttcttttt    120

cttctgtggg agaacttaat gctgcattta tcgttaacct aacaccccaa cataaagaca    180

aaaggaagaa aaggaggaag gaaggaaaag gtgattcgcg aagagagtga tcatgtcagg    240

gcggcccaga accacctcct ttgcggagag ctgcaagccg gtgcagcagc cttcagcttt    300

tggcagcatg aaagttagca gagacaagga cggcagcaag gtgacaacag tggtggcaac    360

tcctgggcag ggtccagaca ggccacaaga agtcagctat acagacacta aagtgattgg    420

aaatggatca tttggtgtgg tatatcaagc caaactttgt gattcaggag aactggtcgc    480

catcaagaaa gtattgcagg acaagagatt taagaatcga gagctccaga tcatgagaaa    540

gctagatcac tgtaacatag tccgattgcg ttatttcttc tactccagtg gtgagaagaa    600

agatgaggtc tatcttaatc tggtgctgga ctatgttccg gaaacagtat acagagttgc    660

cagacactat agtcgagcca aacagacgct ccctgtgatt tatgtcaagt tgtatatgta    720

tcagctgttc cgaagtttag cctatatcca ttcctttgga atctgccatc gggatattaa    780

accgcagaac ctcttgttgg atcctgatac tgctgtatta aaactctgtg actttggaag    840

tgcaaagcag ctggtccgag gagaacccaa tgtttcgtat atctgttctc ggtactatag    900

ggcaccagag ttgatctttg gagccactga ttatacctct agtatagatg tatggtctgc    960

tggctgtgtg ttggctgagc tgttactagg acaaccaata tttccagggg atagtggtgt   1020

ggatcagttg gtagaaataa tcaaggtcct gggaactcca acaagggagc aaatcagaga   1080

aatgaaccca aactacacag aatttaaatt ccctcaaatt aaggcacatc cttggactaa   1140

ggattcgtca ggaacaggac atttcacctc aggagtgcgg gtcttccgac cccgaactcc   1200

accggaggca attgcactgt gtagccgtct gctggagtat acaccaactg cccgactaac   1260

accactggaa gcttgtgcac attcattttt tgatgaatta cgggacccaa atgtcaaact   1320

accaaatggg cgagacacac ctgcactctt caacttcacc actcaagaac tgtcaagtaa   1380

tccacctctg gctaccatcc ttattcctcc tcatgctcgg attcaagcag ctgcttcaac   1440

ccccacaaat gccacagcag cgtcagatgc taatactgga gaccgtggac agaccaataa   1500
```

tgctgcttct gcatcagctt ccaactccac ctgaacagtc ccgagcagcc agctgcacag 1560
gaaaaaccac cagttacttg agtgtcactc agcaacactg gtcacgtttg gaaagaatat 1620
taaaaaaaaa aaaaaaaaa 1639

<210> SEQ ID NO 7
<211> LENGTH: 2276
<212> TYPE: DNA
<213> ORGANISM: Homo sapiens

<400> SEQUENCE: 7
aagcccagca gccccggggc ggatggctcc ggccgcctgg ctccgcagcg cggccgcgcg 60
cgccctcctg cccccgatgc tgctgctgct gctccagccg ccgccgctgc tggcccgggc 120
tctgccgccg gacgcccacc acctccatgc cgagaggagg gggccacagc cctggcatgc 180
agccctgccc agtagcccgg cacctgcccc tgccacgcag gaagcccccc ggcctgccag 240
cagcctcagg cctccccgct gtggcgtgcc cgacccatct gatgggctga gtgcccgcaa 300
ccgacagaag aggttcgtgc tttctggcgg gcgctgggag aagacggacc tcacctacag 360
gatccttcgg ttcccatggc agttggtgca ggagcaggtg cggcagacga tggcagaggc 420
cctaaaggta tggagcgatg tgacgccact cacctttact gaggtgcacg agggccgtgc 480
tgacatcatg atcgacttcg ccaggtactg gcatggggac gacctgccgt ttgatgggcc 540
tgggggcatc ctggcccatg ccttcttccc caagactcac cgagaagggg atgtccactt 600
cgactatgat gagacctgga ctatcgggga tgaccagggc acagacctgc tgcaggtggc 660
agcccatgaa tttggccacg tgctggggct gcagcacaca acagcagcca aggccctgat 720
gtccgccttc tacacctttc gctacccact gagtctcagc ccagatgact gcaggggcgt 780
tcaacaccta tatggccagc cctggcccac tgtcacctcc aggaccccag ccctgggccc 840
ccaggctggg atagacacca atgagattgc accgctggag ccagacgccc cgccagatgc 900
ctgtgaggcc tcctttgacg cggtctccac catccgaggc gagctctttt tcttcaaagc 960
gggctttgtg tggcgcctcc gtgggggcca gctgcagccc ggctacccag cattggcctc 1020
tcgccactgg cagggactgc ccagccctgt ggacgctgcc ttcgaggatg cccagggcca 1080
catttggttc ttccaaggtg ctcagtactg ggtgtacgac ggtgaaaagc cagtcctggg 1140
ccccgcaccc ctcaccgagc tgggcctggt gaggttcccg gtccatgctg ccttggtctg 1200
gggtcccgag aagaacaaga tctacttctt ccgaggcagg gactactggc gtttccaccc 1260
cagcacccgg cgtgtagaca gtcccgtgcc ccgcagggcc actgactgga gaggggtgcc 1320
ctctgagatc gacgctgcct tccaggatgc tgatggctat gcctacttcc tgcgcggccg 1380
cctctactgg aagtttgacc ctgtgaaggt gaaggctctg gaaggcttcc ccgtctcgt 1440 gggtcctgac ttctttggct gtgccgagcc tgccaacact ttcctctgac catggcttgg 1500
atgccctcag ggtgctgac ccctgccagg ccacgaatat caggctagag acccatggcc 1560
atctttgtgg ctgtgggcac caggcatggg actgagccca tgtctcctca gggggatggg 1620
gtggggtaca accaccatga caactgccgg gagggccacg caggtcgtgg tcacctgcca 1680
gcgactgtct cagactgggc agggaggctt tggcatgact taagaggaag ggcagtcttg 1740
ggcccgctat gcaggtcctg gcaaacctgg ctgccctgtc tccatccctg tccctcaggg 1800
tagcaccatg gcaggactgg gggaactgga gtgtccttgc tgtatccctg ttgtgaggtt 1860
ccttccaggg gctggcactg aagcaagggt gctggggccc catggccttc agccctggct 1920
gagcaactgg gctgtagggc agggccactt cctgaggtca ggtcttggta ggtgcctgca 1980

-continued tctgtctgcc ttctggctga caatcctgga aatctgttct ccagaatcca ggccaaaaag 2040
ttcacagtca aatggggagg ggtattcttc atgcaggaga ccccaggccc tggaggctgc 2100
aacatacctc aatcctgtcc caggccggat cctcctgaag cccttttcgc agcactgcta 2160
tcctccaaag ccattgtaaa tgtgtgtaca gtgtgtataa accttcttct tcttttttt 2220 tttttaaact gaggattgtc attaaacaca gttgttttct aaaaaaaaaa aaaaaa 2276

<210> SEQ ID NO 8
<211> LENGTH: 1496
<212> TYPE: DNA
<213> ORGANISM: Homo sapiens

<400> SEQUENCE: 8
gctctaagcg cccggggccc cgcccagtgg ccggcacagc caatcgcagc gcgggaaggc 60
ggtgggggcg gggaaggccg cctggaaact taaatcccga ggcgggcgaa cctgcaccag 120
accgcggacg tctgtaatct cagaggcttg tttgctgagg gtgcctgcgc agctgcgacg 180
gctgctggtt ttgaaacatg aatctttcgc tcgtcctggc tgccttttgc ttgggaatag 240
cctccgctgt tccaaaattt gaccaaaatt tggatacaaa gtggtaccag tggaaggcaa 300
cacacagaag attatatggc gcgaatgaag aaggatggag gagagcagtg tgggaaaaga 360
atatgaaaat gattgaactg cacaatgggg aatacagcca agggaaacat ggcttcacaa 420
tggccatgaa tgcttttggt gacatgacca atgaagaatt caggcagatg atgggttgct 480
ttcgaaacca gaaattcagg aaggggaaag tgttccgtga gcctctgttt cttgatcttc 540
ccaaatctgt ggattggaga aagaaaggct acgtgacgcc agtgaagaat cagaaacagt 600
gtggttcttg ttgggctttt agtgcgactg gtgctcttga aggacagatg ttccggaaaa 660
ctgggaaact tgtctcactg agcgagcaga atctggtgga ctgttcgcgt cctcaaggca 720
atcagggctg caatggtggc ttcatggcta gggccttcca gtatgtcaag gagaacggag 780
gcctggactc tgaggaatcc tatccatatg tagcagtgga tgaaatctgt aagtacagac 840
ctgagaattc tgttgctaat gacactggct tcacagtggt cgcacctgga aaggagaagg 900
ccctgatgaa agcagtcgca actgtggggc ccatctccgt tgctatggat gcaggccatt 960
cgtccttcca gttctacaaa tcaggcattt attttgaacc agactgcagc agcaaaaacc 1020
tggatcatgg tgttctggtg gttggctacg gctttgaagg agcaaattcg aataacagca 1080
agtattggct cgtcaaaaac agctggggtc cagaatgggg ctcgaatggc tatgtaaaaa 1140
tagccaaaga caagaacaac cactgtggaa tcgccacagc agccagctac cccaatgtgt 1200
gagctgatgg atggtgagga ggaaggactt aaggacagca tgtctgggga aattttatct 1260
tgaaactgac caaacgctta ttgtgtaaga taaaccagtt gaatcattga ggatccaagt 1320
tgagatttta attctgtgac atttttacaa gggtaaaatg ttaccactac tttaattatt 1380
gttatacaca gctttatgat atcaaagact cattgcttaa ttctaagact tttgaatttt 1440 catttttttaa aaagatgtac aaaacagttt gaaataaatt ttaattcgta tataaa 1496

<210> SEQ ID NO 9
<211> LENGTH: 2101
<212> TYPE: DNA
<213> ORGANISM: Homo sapiens

<400> SEQUENCE: 9
acgaacaggc caataaggag ggagcagtgc ggggtttaaa tctgaggcta ggctggctct 60
tctcggcgtg ctgcggcgga acggctgttg gtttctgctg ggtgtaggtc cttggctggt 120

-continued

```
cgggcctccg gtgttctgct tctccccgct gagctgctgc ctggtgaaga ggaagccatg    180

gcgctccgag tcaccaggaa ctcgaaaatt aatgctgaaa ataaggcgaa gatcaacatg    240

gcaggcgcaa agcgcgttcc tacggcccct gctgcaacct ccaagcccgg actgaggcca    300

agaacagctc ttggggacat tggtaacaaa gtcagtgaac aactgcaggc caaaatgcct    360

atgaagaagg aagcaaaacc ttcagctact ggaaaagtca ttgataaaaa actaccaaaa    420

cctcttgaaa aggtacctat gctggtgcca gtgccagtgt ctgagccagt gccagagcca    480

gaacctgagc cagaacctga gcctgttaaa gaagaaaaac tttcgcctga gcctattttg    540

gttgatactg cctctccaag cccaatggaa acatctggat gtgcccctgc agaagaagac    600

ctgtgtcagg ctttctctga tgtaattctt gcagtaaatg atgtggatgc agaagatgga    660

gctgatccaa acctttgtag tgaatatgtg aaagatattt atgcttatct gagacaactt    720

gaggaagagc aagcagtcag accaaaatac ctactgggtc gggaagtcac tggaaacatg    780

agagccatcc taattgactg gctagtacag gttcaaatga aattcaggtt gttgcaggag    840

accatgtaca tgactgtctc cattattgat cggttcatgc agaataattg tgtgcccaag    900

aagatgctgc agctggttgg tgtcactgcc atgtttattg caagcaaata tgaagaaatg    960

taccctccag aaattggtga ctttgctttt gtgactgaca acacttatac taagcaccaa   1020

atcagacaga tggaaatgaa gattctaaga gctttaaact ttggtctggg tcggcctcta   1080

cctttgcact tccttcggag agcatctaag attggagagg ttgatgtcga gcaacatact   1140

ttggccaaat acctgatgga actaactatg ttggactatg acatggtgca ctttcctcct   1200

tctcaaattg cagcaggagc tttttgctta gcactgaaaa ttctggataa tggtgaatgg   1260

acaccaactc tacaacatta cctgtcatat actgaagaat ctcttcttcc agttatgcag   1320

cacctggcta agaatgtagt catggtaaat caaggactta caaagcacat gactgtcaag   1380

aacaagtatg ccacatcgaa gcatgctaag atcagcactc taccacagct gaattctgca   1440

ctagttcaag atttagccaa ggctgtggca aaggtgtaac ttgtaaactt gagttggagt   1500

actatattta caaataaaat tggcaccatg tgccatctgt acatattact gttgcattta   1560

cttttaataa agcttgtggc ccctttttact tttttatagc ttaactaatt tgaatgtggt   1620

tacttcctac tgtagggtag cggaaaagtt gtcttaaaag gtatggtggg gatattttta   1680

aaaactcctt ttggtttacc tggggatcca attgatgtat atgtttatat actgggttct   1740

tgttttatat acctggcttt tactttatta atatgagtta ctgaaggtga tggaggtatt   1800

tgaaaatttt acttccatag gacatactgc atgtaagcca agtcatggag aatctgctgc   1860

atagctctat tttaaagtaa aagtctacca ccgaatccct agtcccccctg ttttctgttt   1920

cttcttgtga ttgctgccat aattctaagt tatttacttt taccactatt taagttatca   1980

actttagcta gtatcttcaa actttcactt tgaaaaatga gaattttata ttctaagcca   2040

gttttcattt tggttttgtg ttttggttaa taaaacaata ctcaaataca aaaaaaaaaa   2100

a                                                                    2101
```

<210> SEQ ID NO 10
<211> LENGTH: 2655
<212> TYPE: DNA
<213> ORGANISM: Homo sapiens

<400> SEQUENCE: 10

```
cccagaaggc cgcgggggt ggaccgccta agagggcgtg cgctcccgac atgccccgcg     60

gcgcgccatt aaccgccaga tttgaatcgc gggacccgtt ggcagaggtg gcggcggcgg    120
```

-continued

```
catgggtgcc ccgacgttgc cccctgcctg gcagcccttt ctcaaggacc accgcatctc    180
tacattcaag aactggccct tcttggaggg ctgcgcctgc accccggagc ggatggccga    240
ggctggcttc atccactgcc ccactgagaa cgagccagac ttggcccagt gtttcttctg    300
cttcaaggag ctggaaggct gggagccaga tgacgacccc atagaggaac ataaaaagca    360
ttcgtccggt tgcgctttcc tttctgtcaa gaagcagttt gaagaattaa cccttggtga    420
atttttgaaa ctggacagag aaagagccaa gaacaaaatt gcaaaggaaa ccaacaataa    480
gaagaaagaa tttgaggaaa ctgcggagaa agtgcgccgt gccatcgagc agctggctgc    540
catggattga ggcctctggc cggagctgcc tggtcccaga gtggctgcac cacttccagg    600
gtttattccc tggtgccacc agccttcctg tgggcccctt agcaatgtct taggaaagga    660
gatcaacatt ttcaaattag atgtttcaac tgtgctcttg ttttgtcttg aaagtggcac    720
cagaggtgct tctgcctgtg cagcgggtgc tgctggtaac agtggctgct tctctctctc    780
tctctctttt ttgggggctc atttttgctg ttttgattcc cgggcttacc aggtgagaag    840
tgagggagga agaaggcagt gtcccttttg ctagagctga cagctttgtt cgcgtgggca    900
gagccttcca cagtgaatgt gtctggacct catgttgttg aggctgtcac agtcctgagt    960
gtggacttgg caggtgcctg ttgaatctga gctgcaggtt ccttatctgt cacacctgtg   1020
cctcctcaga ggacagtttt tttgttgttg tgtttttttg tttttttttt tttggtagat   1080
gcatgacttg tgtgtgatga gagaatggag acagagtccc tggctcctct actgtttaac   1140
aacatggctt tcttattttg tttgaattgt taattcacag aatagcacaa actacaatta   1200
aaactaagca caaagccatt ctaagtcatt ggggaaacgg ggtgaacttc aggtggatga   1260
ggagacagaa tagagtgata ggaagcgtct ggcagatact ccttttgcca ctgctgtgtg   1320
attagacagg cccagtgagc cgcggggcac atgctggccg ctcctccctc agaaaaaggc   1380
agtggcctaa atcctttta aatgacttgg ctcgatgctg tgggggactg gctgggctgc   1440
tgcaggccgt gtgtctgtca gcccaacctt cacatctgtc acgttctcca cacgggggag   1500
agacgcagtc cgcccaggtc cccgctttct ttggaggcag cagctcccgc agggctgaag   1560
tctggcgtaa gatgatggat ttgattcgcc ctcctccctg tcatagagct gcagggtgga   1620
ttgttacagc ttcgctggaa acctctggag gtcatctcgg ctgttcctga gaaataaaaa   1680
gcctgtcatt tcaaacactg ctgtggaccc tactgggttt ttaaaatatt gtcagttttt   1740
catcgtcgtc cctagcctgc caacagccat ctgcccagac agccgcagtg aggatgagcg   1800
tcctggcaga gacgcagttg tctctgggcg cttgccagag ccacgaaccc cagacctgtt   1860
tgtatcatcc gggctccttc cgggcagaaa caactgaaaa tgcacttcag acccacttat   1920
ttctgccaca tctgagtcgg cctgagatag acttttccct ctaaactggg agaatatcac   1980
agtggttttt gttagcagaa aatgcactcc agcctctgta ctcatctaag ctgcttattt   2040
ttgatatttg tgtcagtctg taaatggata cttcacttta ataactgttg cttagtaatt   2100
ggctttgtag agaagctgga aaaaaatggt tttgtcttca actcctttgc atgccaggcg   2160
gtgatgtgga tctcggcttc tgtgagcctg tgctgtgggc agggctgagc tggagccgcc   2220
cctctcagcc cgcctgccac ggcctttcct taaaggccat ccttaaaacc agaccctcat   2280
ggctaccagc acctgaaagc ttcctcgaca tctgttaata aagccgtagg ccccttgtcta  2340
agtgcaaccg cctagacttt ctttcagata catgtccaca tgtccatttt tcaggttctc   2400
taagttggag tggagtctgg gaagggttgt gaatgaggct tctgggctat gggtgaggtt   2460
ccaatggcag gttagagccc ctcgggccaa ctgccatcct ggaaagtaga gacagcagtg   2520
```

-continued cccgctgccc agaagagacc agcaagccaa actggagccc ccattgcagg ctgtcgccat 2580
gtggaaagag taactcacaa ttgccaataa agtctcatgt ggttttatct aaaaaaaaaa 2640
aaaaaaaaaa aaaaa 2655

<210> SEQ ID NO 11
<211> LENGTH: 12684
<212> TYPE: DNA
<213> ORGANISM: Homo sapiens

<400> SEQUENCE: 11
gcgggcgggc gggaggactc gactcggtgg gagccgctag agccgggcgc ccggggacgt 60
agcctgtagg gccaccgggt ccccgtcaga ggcggcggcg ggagcagcgg ggactgcagg 120
ccggggtgca gcgaacgcga ccccgcgggc tgcggcccgg tgtgtgcgga gcgtggcggg 180
cgcagcttac cgggcggagg tgagcgcggc gccggctcct cctgcggcgg actttgggtg 240
cgacttgacg agcggtggtt cgacaagtgg ccttgcgggc cggatcgtcc cagtggaaga 300
gttgtaaatt tgcttctggc cttcccctac ggattatacc tggccttccc ctacggatta 360
tactcaactt actgtttaga aaatgtggcc cacgagacgc ctggttacta tcaaaaggag 420
cggggtcgac ggtccccact ttcccctgag cctcagcacc tgcttgtttg gaaggggtat 480
tgaatgtgac atccgtatcc agcttcctgt tgtgtcaaaa caacattgca aaattgaaat 540
ccatgagcag gaggcaatat tacataattt cagttccaca aatccaacac aagtaaatgg 600
gtctgttatt gatgagcctg tacggctaaa acatggagat gtaataacta ttattgatcg 660
ttccttcagg tatgaaaatg aaagtcttca gaatggaagg aagtcaactg aatttccaag 720
aaaaatacgt gaacaggagc cagcacgtcg tgtctcaaga tctagcttct cttctgaccc 780
tgatgagaaa gctcaagatt ccaaggccta ttcaaaaatc actgaaggaa aagtttcagg 840
aaatcctcag gtacatatca agaatgtcaa agaagacagt accgcagatg actcaaaaga 900
cagtgttgct cagggaacaa ctaatgttca ttcctcagaa catgctggac gtaatggcag 960
aaatgcagct gatcccattt ctggggattt taaagaaatt tccagcgtta aattagtgag 1020
ccgttatgga gaattgaagt ctgttcccac tacacaatgt cttgacaata gcaaaaaaaa 1080
tgaatctccc ttttggaagc tttatgagtc agtgaagaaa gagttggatg taaaatcaca 1140
aaaagaaaat gtcctacagt attgtagaaa atctggatta caaactgatt acgcaacaga 1200
gaaagaaagt gctgatggtt tacaggggga gacccaactg ttggtctcgc gtaagtcaag 1260
accaaaatct ggtgggagcg gccacgctgt ggcagagcct gcttcacctg aacaagagct 1320
tgaccagaac aaggggaagg gaagagacgt ggagtctgtt cagactccca gcaaggctgt 1380
gggcgccagc tttcctctct atgagccggc taaaatgaag acccctgtac aatattcaca 1440
gcaacaaaat tctccacaaa aacataagaa caaagacctg tatactactg gtagaagaga 1500
atctgtgaat ctgggtaaaa gtgaaggctt caaggctggt gataaaactc ttactcccag 1560
gaagctttca actagaaatc gaacaccagc taaagttgaa gatgcagctg actctgccac 1620
taagccagaa aatctctctt ccaaaaccag aggaagtatt cctacagatg tggaagttct 1680
gcctacggaa actgaaattc acaatgagcc atttttaact ctgtggctca ctcaagttga 1740
gaggaagatc caaaaggatt ccctcagcaa gcctgagaaa ttgggcacta cagctggaca 1800
gatgtgctct gggttacctg gtcttagttc agttgatatc aacaactttg gtgattccat 1860
taatgagagt gagggaatac ctttgaaaag aaggcgtgtg tcctttggtg ggcacctaag 1920
acctgaacta tttgatgaaa acttgcctcc taatacgcct ctcaaaaggg gagaagcccc 1980

-continued

```
aaccaaaaga aagtctctgg taatgcacac tccacctgtc ctgaagaaaa tcatcaagga   2040
acagcctcaa ccatcaggaa aacaagagtc aggttcagaa atccatgtgg aagtgaaggc   2100
acaaagcttg gttataagcc ctccagctcc tagtcctagg aaaactccag ttgccagtga   2160
tcaacgccgt aggtcctgca aaacagcccc tgcttccagc agcaaatctc agacagaggt   2220
tcctaagaga ggagggagaa agagtggcaa cctgccttca aagagagtgt ctatcagccg   2280
aagtcaacat gatattttac agatgatatg ttccaaaaga agaagtggtg cttcggaagc   2340
aaatctgatt gttgcaaaat catgggcaga tgtagtaaaa cttggtgcaa aacaaacaca   2400
aactaaagtc ataaaacatg gtcctcaaag gtcaatgaac aaaaggcaaa gaagacctgc   2460
tactccaaag aagcctgtgg gcgaagttca cagtcaattt agtacaggcc acgcaaactc   2520
tccttgtacc ataataatag ggaaagctca tactgaaaaa gtacatgtgc ctgctcgacc   2580
ctacagagtg ctcaacaact tcatttccaa ccaaaaaatg gactttaagg aagatctttc   2640
aggaatagct gaaatgttca agaccccagt gaaggagcaa ccgcagttga caagcacatg   2700
tcacatcgct atttcaaatt cagagaattt gcttggaaaa cagtttcaag gaactgattc   2760
aggagaagaa cctctgctcc ccacctcaga gagttttgga ggaaatgtgt tcttcagtgc   2820
acagaatgca gcaaaacagc catctgataa atgctctgca agccctccct taagacggca   2880
gtgtattaga gaaaatggaa acgtagcaaa aacgcccagg aacacctaca aaatgacttc   2940
tctggagaca aaaacttcag atactgagac agagccttca aaaacagtat ccactgcaaa   3000
caggtcagga aggtctacag agttcaggaa tatacagaag ctacctgtgg aaagtaagag   3060
tgaagaaaca aatacagaaa ttgttgagtg catcctaaaa agaggtcaga aggcaacact   3120
actacaacaa aggagagaag gagagatgaa ggaaatagaa agaccttttg agacatataa   3180
ggaaaatatt gaattaaaag aaaacgatga aaagatgaaa gcaatgaaga gatcaagaac   3240
ttgggggcag aaatgtgcac caatgtctga cctgacagac ctcaagagct tgcctgatac   3300
agaactcatg aaagacacgg cacgtggcca gaatctcctc caaacccaag atcatgccaa   3360
ggcaccaaag agtgagaaag gcaaaatcac taaaatgccc tgccagtcat tacaaccaga   3420
accaataaac accccaacac acacaaaaca acagttgaag gcatccctgg ggaaagtagg   3480
tgtgaaagaa gagctcctag cagtcggcaa gttcacacgg acgtcagggg agaccacgca   3540
cacgcacaga gagccagcag gagatggcaa gagcatcaga acgtttaagg agtctccaaa   3600
gcagatcctg gacccagcag cccgtgtaac tggaatgaag aagtggccaa gaacgcctaa   3660
ggaagaggcc cagtcactag aagacctggc tggcttcaaa gagctcttcc agacaccagg   3720
tccctctgag gaatcaatga ctgatgagaa aactaccaaa atagcctgca aatctccacc   3780
accagaatca gtggacactc caacaagcac aaagcaatgg cctaagagaa gtctcaggaa   3840
agcagatgta gaggaagaat tcttagcact caggaaacta acaccatcag cagggaaagc   3900
catgcttacg cccaaaccag caggaggtga tgagaaagac attaaagcat ttatgggaac   3960
tccagtgcag aaactggacc tggcaggaac tttacctggc agcaaaagac agctacagac   4020
tcctaaggaa aaggcccagg ctctagaaga cctggctggc tttaaagagc tcttccagac   4080
tcctggtcac accgaggaat tagtggctgc tggtaaaacc actaaaatac cctgcgactc   4140
tccacagtca gacccagtgg acaccccaac aagcacaaag caacgaccca agagaagtat   4200
caggaaagca gatgtagagg gagaactctt agcgtgcagg aatctaatgc catcagcagg   4260
caaagccatg cacacgccta aaccatcagt aggtgaagag aaagacatca tcatatttgt   4320
gggaactcca gtgcagaaac tggacctgac agagaactta accggcagca agagacggcc   4380
```

-continued

```
acaaactcct aaggaagagg cccaggctct ggaagacctg actggcttta aagagctctt   4440
ccagacccct ggtcatactg aagaagcagt ggctgctggc aaaactacta aaatgccctg   4500
cgaatcttct ccaccagaat cagcagacac ccccaacaagc acaagaaggc agcccaagac   4560
acctttggag aaaagggacg tacagaagga gctctcagcc ctgaagaagc tcacacagac   4620
atcaggggaa accacacaca cagataaagt accaggaggt gaggataaaa gcatcaacgc   4680
gtttagggaa actgcaaaac agaaactgga cccagcagca agtgtaactg gtagcaagag   4740
gcacccaaaa actaaggaaa aggcccaacc cctagaagac ctggctggct tgaaagagct   4800
cttccagaca ccagtatgca ctgacaagcc cacgactcac gagaaaacta ccaaaatagc   4860
ctgcagatca caaccagacc cagtggacac accaacaagc tccaagccac agtccaagag   4920
aagtctcagg aaagtggacg tagaagaaga attcttcgca ctcaggaaac gaacaccatc   4980
agcaggcaaa gccatgcaca cacccaaacc agcagtaagt ggtgagaaaa acatctacgc   5040
atttatggga actccagtgc agaaactgga cctgacagag aacttaactg gcagcaagag   5100
acggctacaa actcctaagg aaaaggccca ggctctagaa gacctggctg gctttaaaga   5160
gctcttccag acacgaggtc acactgagga atcaatgact aacgataaaa ctgccaaagt   5220
agcctgcaaa tcttcacaac cagacccaga caaaaaccca gcaagctcca agcgacggct   5280
caagacatcc ctggggaaag tgggcgtgaa agaagagctc ctagcagttg gcaagctcac   5340
acagacatca ggagagacta cacacacaca cacagagcca acaggagatg gtaagagcat   5400
gaaagcattt atggagtctc caaagcagat cttagactca gcagcaagtc taactggcag   5460
caagaggcag ctgagaactc ctaagggaaa gtctgaagtc cctgaagacc tggccggctt   5520
catcgagctc ttccagacac caagtcacac taaggaatca atgactaacg aaaaaactac   5580
caaagtatcc tacagagctt cacagccaga cctagtggac accccaacaa gctccaagcc   5640
acagcccaag agaagtctca ggaaagcaga cactgaagaa gaatttttag catttaggaa   5700
acaaacgcca tcagcaggca aagccatgca cacacccaaa ccagcagtag gtgaagagaa   5760
agacatcaac acgtttttgg gaactccagt gcagaaactg gaccagccag gaaatttacc   5820
tggcagcaat agacggctac aaactcgtaa ggaaaaggcc caggctctag aagaactgac   5880
tggcttcaga gagcttttcc agacaccatg cactgataac cccacgactg atgagaaaac   5940
taccaaaaaa atactctgca aatctccgca atcagaccca gcggacaccc caacaaacac   6000
aaagcaacgg cccaagagaa gcctcaagaa agcagacgta gaggaagaat ttttagcatt   6060
caggaaacta acaccatcag caggcaaagc catgcacacg cctaaagcag cagtaggtga   6120
agagaaagac atcaacacat ttgtggggac tccagtggag aaactggacc tgctaggaaa   6180
tttacctggc agcaagagac ggccacaaac tcctaaagaa aaggccaagg ctctagaaga   6240
tctggctggc ttcaaagagc tcttccagac accaggtcac actgaggaat caatgaccga   6300
tgacaaaatc acagaagtat cctgcaaatc tccacaacca gacccagtca aaaccccaac   6360
aagctccaag caacgactca agatatcctt ggggaaagta ggtgtgaaag aagaggtcct   6420
accagtcggc aagctcacac agacgtcagg gaagaccaca cagacacaca gagagacagc   6480
aggagatgga aagagcatca aagcgtttaa ggaatctgca aagcagatgc tggacccagc   6540
aaactatgga actgggatgg agaggtggcc aagaacacct aaggaagagg cccaatcact   6600
agaagacctg gccggcttca aagagctctt ccagacacca gaccacactg aggaatcaac   6660
aactgatgac aaaactacca aaatagcctg caaatctcca ccaccagaat caatggacac   6720
tccaacaagc acaaggaggc ggcccaaaac acctttgggg aaaagggata tagtggaaga   6780
```

-continued gctctcagcc ctgaagcagc tcacacagac cacacacaca gacaaagtac caggagatga 6840
ggataaaggc atcaacgtgt tcagggaaac tgcaaaacag aaactggacc cagcagcaag 6900
tgtaactggt agcaagaggc agccaagaac tcctaaggga aaagcccaac ccctagaaga 6960
cttggctggc ttgaaagagc tcttccagac accaatatgc actgacaagc ccacgactca 7020
tgagaaaact accaaaatag cctgcagatc tccacaacca gacccagtgg gtaccccaac 7080
aatcttcaag ccacagtcca agagaagtct caggaaagca gacgtagagg aagaatcctt 7140
agcactcagg aaacgaacac catcagtagg gaaagctatg gacacaccca aaccagcagg 7200
aggtgatgag aaagacatga aagcatttat gggaactcca gtgcagaaat tggacctgcc 7260
aggaaattta cctggcagca aaagatggcc acaaactcct aaggaaaagg cccaggctct 7320
agaagacctg gctggcttca aagagctctt ccagacacca ggcactgaca agcccacgac 7380
tgatgagaaa actaccaaaa tagcctgcaa atctccacaa ccagacccag tggacacccc 7440
agcaagcaca aagcaacggc ccaagagaaa cctcaggaaa gcagacgtag aggaagaatt 7500
tttagcactc aggaaacgaa caccatcagc aggcaaagcc atggacacac caaaaccagc 7560
agtaagtgat gagaaaaata tcaacacatt tgtggaaact ccagtgcaga aactggacct 7620
gctaggaaat ttacctggca gcaagagaca gccacagact cctaaggaaa aggctgaggc 7680
tctagaggac ctggttggct tcaaagaact cttccagaca ccaggtcaca ctgaggaatc 7740
aatgactgat gacaaaatca cagaagtatc ctgtaaatct ccacagccag agtcattcaa 7800
aacctcaaga agctccaagc aaaggctcaa gatacccctg gtgaaagtgg acatgaaaga 7860
agagccccta gcagtcagca agctcacacg gacatcaggg gagactacgc aaacacacac 7920
agagccaaca ggagatagta agagcatcaa agcgtttaag gagtctccaa agcagatcct 7980
ggacccagca gcaagtgtaa ctggtagcag gaggcagctg agaactcgta aggaaaaggc 8040
ccgtgctcta gaagacctgg ttgacttcaa agagctcttc tcagcaccag gtcacactga 8100
agagtcaatg actattgaca aaaacacaaa aattccctgc aaatctcccc caccagaact 8160
aacagacact gccacgagca caaagagatg ccccaagaca cgtcccagga aagaagtaaa 8220
agaggagctc tcagcagttg agaggctcac gcaaacatca gggcaaagca cacacacaca 8280
caaagaacca gcaagcggtg atgagggcat caaagtattg aagcaacgtg caaagaagaa 8340
accaaaccca gtagaagagg aacccagcag gagaaggcca agagcaccta aggaaaaggc 8400
ccaacccctg gaagacctgg ccggcttcac agagctctct gaaacatcag gtcacactca 8460
ggaatcactg actgctggca aagccactaa aataccctgc gaatctcccc cactagaagt 8520
ggtagacacc acagcaagca caaagaggca tctcaggaca cgtgtgcaga aggtacaagt 8580
aaaagaagag ccttcagcag tcaagttcac acaaacatca ggggaaacca cggatgcaga 8640
caaagaacca gcaggtgaag ataaaggcat caaagcattg aaggaatctg caaaacagac 8700
accggctcca gcagcaagtg taactggcag caggagacgg ccaagagcac ccagggaaag 8760
tgcccaagcc atagaagacc tagctggctt caaagaccca gcagcaggtc acactgaaga 8820
atcaatgact gatgacaaaa ccactaaaat accctgcaaa tcatcaccag aactagaaga 8880
caccgcaaca agctcaaaga gacggcccag gacacgtgcc cagaaagtag aagtgaagga 8940
ggagctgtta gcagttggca agctcacaca aacctcaggg gagaccacgc acaccgacaa 9000
agagccggta ggtgagggca aaggcacgaa agcatttaag caacctgcaa agcggaagct 9060
ggacgcagaa gatgtaattg gcagcaggag acagccaaga gcacctaagg aaaaggccca 9120
acccctggaa gatctggcca gcttccaaga gctctctcaa acaccaggcc acactgagga 9180

-continued

```
actggcaaat ggtgctgctg atagctttac aagcgctcca aagcaaacac ctgacagtgg   9240
aaaacctcta aaaatatcca gaagagttct tcgggcccct aaagtagaac ccgtgggaga   9300
cgtggtaagc accagagacc ctgtaaaatc acaaagcaaa agcaacactt ccctgccccc   9360
actgcccttc aagaggggag gtggcaaaga tggaagcgtc acgggaacca agaggctgcg   9420
ctgcatgcca gcaccagagg aaattgtgga ggagctgcca gccagcaaga agcagagggt   9480
tgctcccagg gcaagaggca aatcatccga acccgtggtc atcatgaaga gaagtttgag   9540
gacttctgca aaaagaattg aacctgcgga agagctgaac agcaacgaca tgaaaaccaa   9600
caaagaggaa cacaaattac aagactcggt ccctgaaaat aagggaatat ccctgcgctc   9660
cagacgccaa aataagactg aggcagaaca gcaaataact gaggtctttg tattagcaga   9720
aagaatagaa ataaacagaa atgaaaagaa gcccatgaag acctccccag agatggacat   9780
tcagaatcca gatgatggag cccggaaacc catacctaga gacaaagtca ctgagaacaa   9840
aaggtgcttg aggtctgcta gacagaatga gagctcccag cctaaggtgg cagaggagag   9900
cggagggcag aagagtgcga aggttctcat gcagaatcag aaagggaaag gagaagcagg   9960
aaattcagac tccatgtgcc tgagatcaag aaagacaaaa agccagcctg cagcaagcac  10020
tttggagagc aaatctgtgc agagagtaac gcggagtgtc aagaggtgtg cagaaaatcc  10080
aaagaaggct gaggacaatg tgtgtgtcaa gaaaataaga accagaagtc atagggacag  10140
tgaagatatt tgacagaaaa atcgaactgg gaaaaatata ataaagttag ttttgtgata  10200
agttctagtg cagtttttgt cataaattac aagtgaattc tgtaagtaag gctgtcagtc  10260
tgcttaaggg aagaaaactt tggatttgct gggtctgaat cggcttcata aactccactg  10320
ggagcactgc tgggctcctg gactgagaat agttgaacac cgggggcttt gtgaaggagt  10380
ctgggccaag gtttgccctc agctttgcag aatgaagcct tgaggtctgt caccacccac  10440
agccacccta cagcagcctt aactgtgaca cttgccacac tgtgtcgtcg tttgtttgcc  10500
tatgtcctcc agggcacggt ggcaggaaca actatcctcg tctgtcccaa cactgagcag  10560
gcactcggta aacacgaatg aatggatgag cgcacggatg aatggagctt acaagatctg  10620
tctttccaat ggccgggggc atttggtccc caaattaagg ctattggaca tctgcacagg  10680
acagtcctat ttttgatgtc ctttcctttc tgaaaataaa gttttgtgct ttggagaatg  10740
actcgtgagc acatctttag ggaccaagag tgactttctg taaggagtga ctcgtggctt  10800
gccttggtct cttgggaata cttttctaac tagggttgct ctcacctgag acattctcca  10860
cccgcggaat ctcagggtcc caggctgtgg gccatcacga cctcaaactg gctcctaatc  10920
tccagctttc ctgtcattga aagcttcgga agtttactgg ctctgctccc gcctgttttc  10980
tttctgactc tatctggcag cccgatgcca cccagtacag gaagtgacac cagtactctg  11040
taaagcatca tcatccttgg agagactgag cactcagcac cttcagccac gatttcagga  11100
tcgcttcctt gtgagccgct gcctccgaaa tctcctttga agcccagaca tctttctcca  11160
gcttcagact tgtagatata actcgttcat cttcatttac tttccacttt gccccctgtc  11220
ctctctgtgt tccccaaatc agagaatagc ccgccatccc ccaggtcacc tgtctggatt  11280
cctccccatt cacccacctt gccaggtgca ggtgaggatg gtgcaccaga cagggtagct  11340
gtcccccaaa atgtgccctg tgcgggcagt gccctgtctc cacgtttgtt tccccagtgt  11400
ctggcgggga gccaggtgac atcataaata cttgctgaat gaatgcagaa atcagcggta  11460
ctgacttgta ctatattggc tgccatgata gggttctcac agcgtcatcc atgatcgtaa  11520
gggagaatga cattctgctt gagggaggga atagaaaggg gcagggaggg gacatctgag  11580
```

ggcttcacag ggctgcaaag ggtacaggga ttgcaccagg gcagaacagg ggagggtgtt 11640
caaggaagag tggctcttag cagaggcact ttggaaggtg tgaggcataa atgcttcctt 11700
ctacgtaggc caacctcaaa actttcagta ggaatgttgc tatgatcaag ttgttctaac 11760
actttagact tagtagtaat tatgaacctc acatagaaaa atttcatcca gccatatgcc 11820
tgtggagtgg aatattctgt ttagtagaaa aatcctttag agttcagctc taaccagaaa 11880
tcttgctgaa gtatgtcagc accttttctc accctggtaa gtacagtatt tcaagagcac 11940
gctaagggtg gttttcattt tacagggctg ttgatgatgg gttaaaaatg ttcatttaag 12000
ggctaccccc gtgtttaata gatgaacacc acttctacac aaccctcctt ggtactgggg 12060
gagggagaga tctgacaaat actgcccatt cccctaggct gactggattt gagaacaaat 12120
acccacccat ttccaccatg gtatggtaac ttctctgagc ttcagtttcc aagtgaattt 12180
ccatgtaata ggacattccc attaaataca agctgttttt actttttcgc ctcccagggc 12240
ctgtgggatc tggtccccca gcctctcttg ggctttctta cactaactct gtacctacca 12300
tctcctgcct cccttaggca ggcacctcca accaccacac actccctgct gttttccctg 12360
cctggaactt tccctcctgc cccaccaaga tcatttcatc cagtcctgag ctcagcttaa 12420
gggaggcttc ttgcctgtgg gttccctcac ccccatgcct gtcctccagg ctggggcagg 12480
ttcttagttt gcctggaatt gttctgtacc tctttgtagc acgtagtgtt gtggaaacta 12540
agccactaat tgagtttctg gctcccctcc tggggttgta agttttgttc attcatgagg 12600
gccgactgca tttcctggtt actctatccc agtgaccagc cacaggagat gtccaataaa 12660
gtatgtgatg aaatggtctt aaaa 12684

<210> SEQ ID NO 12
<211> LENGTH: 2346
<212> TYPE: DNA
<213> ORGANISM: Homo sapiens

<400> SEQUENCE: 12
acaaggcagc ctcgctcgag cgcaggccaa tcggctttct agctagaggg tttaactcct 60
atttaaaaag aagaaccttt gaattctaac ggctgagctc ttggaagact tgggtccttg 120
ggtcgcaggt gggagccgac gggtgggtag accgtggggg atatctcagt ggcggacgag 180
gacggcgggg acaaggggcg gctggtcgga gtggcggagc gtcaagtccc ctgtcggttc 240
ctccgtccct gagtgtcctt ggcgctgcct tgtgcccgcc cagcgccttt gcatccgctc 300
ctgggcaccg aggcgccctg taggatactg cttgttactt attacagcta gaggcatcat 360
ggaccgatct aaagaaaact gcatttcagg acctgttaag gctacagctc cagttggagg 420
tccaaaacgt gttctcgtga ctcagcaatt tccttgtcag aatccattac ctgtaaatag 480
tggccaggct cagcgggtct tgtgtccttc aaattcttcc cagcgcattc ctttgcaagc 540
acaaaagctt gtctccagtc acaagccggt tcagaatcag aagcagaagc aattgcaggc 600
aaccagtgta cctcatcctg tctccaggcc actgaataac acccaaaaga gcaagcagcc 660
cctgccatcg gcacctgaaa ataatcctga ggaggaactg gcatcaaaac agaaaaatga 720
agaatcaaaa aagaggcagt gggctttgga agactttgaa attggtcgcc ctctgggtaa 780
aggaaagttt ggtaatgttt atttggcaag agaaaagcaa agcaagttta ttctggctct 840
taaagtgtta tttaaagctc agctggagaa agccggagtg gagcatcagc tcagaagaga 900
agtagaaata cagtcccacc ttcggcatcc taatattctt agactgtatg gttatttcca 960
tgatgctacc agagtctacc taattctgga atatgcacca cttggaacag tttatagaga 1020
acttcagaaa ctttcaaagt ttgatgagca gagaactgct acttatataa cagaattggc 1080
aaatgccctg tcttactgtc attcgaagag agttattcat agagacatta agccagagaa 1140
cttacttctt ggatcagctg gagagcttaa aattgcagat tttgggtggt cagtacatgc 1200
tccatcttcc aggaggacca ctctctgtgg caccctggac tacctgcccc ctgaaatgat 1260
tgaaggtcgg atgcatgatg agaaggtgga tctctggagc cttggagttc tttgctatga 1320
atttttagtt gggaagcctc cttttgaggc aaacacatac caagagacct acaaaagaat 1380
atcacgggtt gaattcacat tccctgactt tgtaacagag ggagccaggg acctcatttc 1440
aagactgttg aagcataatc ccagccagag gccaatgctc agagaagtac ttgaacaccc 1500
ctggatcaca gcaaattcat caaaaccatc aaattgccaa aacaaagaat cagctagcaa 1560
acagtcttag gaatcgtgca gggggagaaa tccttgagcc agggctgcca tataacctga 1620
caggaacatg ctactgaagt ttattttacc attgactgct gccctcaatc tagaacgcta 1680
cacaagaaat atttgtttta ctcagcaggt gtgccttaac ctccctattc agaaagctcc 1740
acatcaataa acatgacact ctgaagtgaa agtagccacg agaattgtgc tacttatact 1800
ggttcataat ctggaggcaa ggttcgactg cagccgcccc gtcagcctgt gctaggcatg 1860
gtgtcttcac aggaggcaaa tccagagcct ggctgtgggg aaagtgacca ctctgccctg 1920
accccgatca gttaaggagc tgtgcaataa ccttcctagt acctgagtga gtgtgtaact 1980
tattgggttg gcgaagcctg gtaaagctgt tggaatgagt atgtgattct ttttaagtat 2040
gaaaataaag atatatgtac agacttgtat tttttctctg gtggcattcc tttaggaatg 2100
ctgtgtgtct gtccggcacc ccggtaggcc tgattgggtt tctagtcctc cttaaccact 2160
tatctcccat atgagagtgt gaaaaatagg aacacgtgct ctacctccat ttagggattt 2220
gcttgggata cagaagaggc catgtgtctc agagctgtta agggcttatt tttttaaaac 2280
attggagtca tagcatgtgt gtaaacttta aatatgcaaa taaataagta tctatgtcta 2340
aaaaaa 2346

<210> SEQ ID NO 13
<211> LENGTH: 3008
<212> TYPE: DNA
<213> ORGANISM: Homo sapiens

<400> SEQUENCE: 13
taattatggg tctgtaacca ccctggactg ggtgctcctc actgacggac ttgtctgaac 60
ctctctttgt ctccagcgcc cagcactggg cctggcaaaa cctgagacgc ccggtacatg 120
ttggccaaat gaatgaacca gattcagacc ggcaggggcg ctgtggttta ggaggggcct 180
ggggtttctc ccaggaggtt tttgggcttg cgctggaggg ctctggactc ccgtttgcgc 240
cagtggcctg catcctggtc ctgtcttcct catgtttgaa tttctttgct ttcctagtct 300
ggggagcagg gaggagccct gtgccctgtc ccaggatcca tgggtaggaa caccatggac 360
agggagagca aacggggcca tctgtcacca ggggcttagg gaaggccgag ccagcctggg 420
tcaaagaagt caaaggggct gcctggagga ggcagcctgt cagctggtgc atcagaggct 480
gtggccaggc cagctgggct cggggagcgc cagcctgaga ggagcgcgtg agcgtcgcgg 540
gagcctcggg caccatgagc gacgtggcta ttgtgaagga gggttggctg cacaaacgag 600
gggagtacat caagacctgg cggccacgct acttcctcct caagaatgat ggcaccttca 660
ttggctacaa ggagcggccg caggatgtgg accaacgtga ggctcccctc aacaacttct 720
ctgtggcgca gtgccagctg atgaagacgg agcggccccg gcccaacacc ttcatcatcc 780

```
gctgcctgca gtggaccact gtcatcgaac gcaccttcca tgtggagact cctgaggagc    840
gggaggagtg gacaaccgcc atccagactg tggctgacgg cctcaagaag caggaggagg    900
aggagatgga cttccggtcg ggctcaccca gtgacaactc aggggctgaa gagatggagg    960
tgtccctggc caagcccaag caccgcgtga ccatgaacga gtttgagtac ctgaagctgc   1020
tgggcaaggg cactttcggc aaggtgatcc tggtgaagga gaaggccaca ggccgctact   1080
acgccatgaa gatcctcaag aaggaagtca tcgtggccaa ggacgaggtg gcccacacac   1140
tcaccgagaa ccgcgtcctg cagaactcca ggcacccctt cctcacagcc ctgaagtact   1200
ctttccagac ccacgaccgc ctctgctttg tcatggagta cgccaacggg ggcgagctgt   1260
tcttccacct gtcccgggag cgtgtgttct ccgaggaccg ggcccgcttc tatggcgctg   1320
agattgtgtc agccctggac tacctgcact cggagaagaa cgtggtgtac cgggacctca   1380
agctggagaa cctcatgctg gacaaggacg ggcacattaa gatcacagac ttcgggctgt   1440
gcaaggaggg gatcaaggac ggtgccacca tgaagacctt ttgcggcaca cctgagtacc   1500
tggcccccga ggtgctggag gacaatgact acggccgtgc agtggactgg tgggggctgg   1560
gcgtggtcat gtacgagatg atgtgcggtc gcctgccctt ctacaaccag gaccatgaga   1620
agctttttga gctcatcctc atggaggaga tccgcttccc gcgcacgctt ggtcccgagg   1680
ccaagtcctt gctttcaggg ctgctcaaga aggaccccaa gcagaggctt ggcgggggct   1740
ccgaggacgc caaggagatc atgcagcatc gcttctttgc cggtatcgtg tggcagcacg   1800
tgtacgagaa gaagctcagc ccacccttca agccccaggt cacgtcggag actgacacca   1860
ggtattttga tgaggagttc acggcccaga tgatcaccat cacaccacct gaccaagatg   1920
acagcatgga gtgtgtggac agcgagcgca ggcccccactt cccccagttc tcctactcgg   1980
ccagcggcac ggcctgaggc ggcggtggac tgcgctggac gatagcttgg agggatggag   2040
aggcggcctc gtgccatgat ctgtatttaa tggtttttat ttctcgggtg catttgagag   2100
aagccacgct gtcctctcga gcccagatgg aaagacgttt ttgtgctgtg ggcagcaccc   2160
tcccccgcag cggggtaggg aagaaaacta tcctgcgggt tttaatttat ttcatccagt   2220
ttgttctccg ggtgtggcct cagccctcag aacaatccga ttcacgtagg gaaatgttaa   2280
ggacttctgc agctatgcgc aatgtggcat tggggggccg ggcaggtcct gcccatgtgt   2340
cccctcactc tgtcagccag ccgccctggg ctgtctgtca ccagctatct gtcatctctc   2400
tggggccctg ggcctcagtt caacctggtg gcaccagatg caacctcact atggtatgct   2460
ggccagcacc ctctcctggg ggtggcaggc acacagcagc cccccagcac taaggccgtg   2520
tctctgagga cgtcatcgga ggctgggccc ctgggatggg accagggatg ggggatgggc   2580
cagggtttac ccagtgggac agaggagcaa ggtttaaatt tgttattgtg tattatgttg   2640
ttcaaatgca ttttgggggt ttttaatctt tgtgacagga aagccctccc ccttcccctt   2700
ctgtgtcaca gttcttggtg actgtcccac cgggagcctc cccctcagat gatctctcca   2760
cggtagcact tgacctttc gacgcttaac ctttccgctg tcgccccagg ccctccctga   2820
ctccctgtgg gggtggccat ccctgggccc ctccacgcct cctggccaga cgctgccgct   2880
gccgctgcac cacggcgttt ttttacaaca ttcaacttta gtatttttac tattataata   2940
taatatggaa ccttccctcc aaattcttca ataaaagttg cttttcaaaa aaaaaaaaaa   3000
aaaaaaaa                                                            3008
```

<210> SEQ ID NO 14
<211> LENGTH: 1872
<212> TYPE: DNA

-continued

<213> ORGANISM: Homo sapiens

<400> SEQUENCE: 14
ttaattacaa aaactaatga ctaagagaga ggtggctaga gctgaggccc ctgagtcagg 60
ctgtgggtgg gatcatctcc agtacaggaa gtgagacttt catttcctcc tttccaagag 120
agggctgagg gagcagggtt gagcaactgg tgcagacagc ctagctggac tttgggtgag 180
gcggttcagc catgaggctg gctgtgcttt tctcgggggc cctgctgggg ctactggcag 240
cccaggggac agggaatgac tgtcctcaca aaaaatcagc tactttgctg ccatccttca 300
cggtgacacc cacggttaca gagagcactg gaacaaccag ccacaggact accaagagcc 360
acaaaaccac cactcacagg acaaccacca caggcaccac cagccacgga cccacgactg 420
ccactcacaa ccccaccacc accagccatg gaaacgtcac agttcatcca acaagcaata 480
gcactgccac cagccaggga ccctcaactg ccactcacag tcctgccacc actagtcatg 540
gaaatgccac ggttcatcca acaagcaaca gcactgccac cagcccagga ttcaccagtt 600
ctgcccaccc agaaccacct ccaccctctc cgagtcctag cccaacctcc aaggagacca 660
ttggagacta cacgtggacc aatggttccc agccctgtgt ccacctccaa gcccagattc 720
agattcgagt catgtacaca acccagggtg gaggagaggc ctggggcatc tctgtactga 780
accccaacaa aaccaaggtc cagggaagct gtgagggtgc ccatccccac ctgcttctct 840
cattccccta tggacacctc agctttggat tcatgcagga cctccagcag aaggttgtct 900
acctgagcta catggcggtg gagtacaatg tgtccttccc ccacgcagca cagtggacat 960
tctcggctca gaatgcatcc cttcgagatc tccaagcacc cctggggcag agcttcagtt 1020
gcagcaactc gagcatcatt ctttcaccag ctgtccacct cgacctgctc tccctgaggc 1080
tccaggctgc tcagctgccc cacacagggg tctttgggca aagtttctcc tgccccagtg 1140
accggtccat cttgctgcct ctcatcatcg gcctgatcct tcttggcctc ctcgccctgg 1200
tgcttattgc tttctgcatc atccggagac gcccatccgc ctaccaggcc ctctgagcat 1260
ttgcttcaaa ccccagggca ctgagggggt tggggtgtgg tggggggggta cccttatttc 1320 ctcgacacgc aactggctca aagacaatgt tattttcctt ccctttcttg aagaacaaaa 1380
agaaagccgg gcatgacggc tcatgcctgt aatcccagca ctttgggagg ctgaggcagg 1440
tggatcactg gaggtcagga gtttgagacc agcctggcca acatggtgaa accctgtctc 1500
tactaaaaat acaattagcc aggtgtggcg gcgtaatccc agctggcctg taatcccagc 1560
tacttgggag gctgaggcag aactgcttga acccaggagg tggaggttgc agtgagccgt 1620
catcgcgcca ctaagccaag atcgcgccac tgcactccag cctgggcgac agagccagac 1680
tgtctcaaat aaataaatat gagataatgc agtcgggaga agggagggag agaattttat 1740
taaatgtgac gaactgcccc cccccccccc ccagcaggag agcagcaaaa tttatgcaaa 1800
tctttgacgg ggttttcctt gtcctgccag gattaaaagc catgagtttc ttgtcaaaaa 1860
aaaaaaaaaa aa 1872

<210> SEQ ID NO 15
<211> LENGTH: 3885
<212> TYPE: DNA
<213> ORGANISM: Homo sapiens

<400> SEQUENCE: 15
gcaggccggg gcggggctgg gaagtagtcg ggcggggttg tgagacgccg cgctcagctt 60
ccatcgctgg gcggtcaaca agtgcgggcc tggctcagcg cggggggggcg cggagaccgc 120

-continued

```
gaggcgaccg ggagcggctg ggttcccggc tgcgcgccct tcggccaggc cgggagccgc    180
gccagtcgga gcccccggcc cagcgtggtc cgcctccctc tgggcgtcca cctgcccgga    240
gtactgccag cgggcatgac cgacccacca ggggcgccgc cgccggcgct cgcaggccgc    300
ggatgaagaa gaaaacccgg cgccgctcga cccggagcga ggagttgacc cggagcgagg    360
agttgaccct gagtgaggaa gcgacctgga gtgaagaggc gacccagagt gaggaggcga    420
cccagggcga agagatgaat cggagccagg aggtgacccg ggacgaggag tcgacccgga    480
gcgaggaggt gaccagggag gaaatggcgg cagctgggct caccgtgact gtcacccaca    540
gcaatgagaa gcacgacctt catgttacct cccagcaggg cagcagtgaa ccagttgtcc    600
aagacctggc ccaggttgtt gaagaggtca taggggttcc acagtctttt cagaaactca    660
tatttaaggg aaaatctctg aaggaaatgg aaacaccgtt gtcagcactt ggaatacaag    720
atggttgccg ggtcatgtta attgggaaaa agaacagtcc acaggaagag gttgaactaa    780
agaagttgaa acatttggag aagtctgtgg agaagatagc tgaccagctg gaagagttga    840
ataaagagct tactggaatc cagcagggtt ttctgcccaa ggatttgcaa gctgaagctc    900
tctgcaaact tgataggaga gtaaaagcca caatagagca gtttatgaag atcttggagg    960
agattgacac actgatcctg ccagaaaatt tcaaagacag tagattgaaa aggaaaggct   1020
tggtaaaaaa ggttcaggca ttcctagccg agtgtgacac agtggagcag aacatctgcc   1080
aggagactga gcggctgcag tctacaaact ttgccctggc cgagtgaggt gtagcagaaa   1140
aaggctgtgc tgccctgaag aatggcgcca ccagctctgc cgtctctgga gcggaattta   1200
cctgatttct tcagggctgc tgggggcaac tggccatttg ccaattttcc tactctcaca   1260
ctggttctca atgaaaaata gtgtctttgt gattttgagt aaagctccta tctgttttct   1320
ccttctgtct ctgtggttgt actgtccagc aatccacctt ttctggagag ggccacctct   1380
gcccaaattt tcccagctgt ttggacctct gggtgctttc tttgggctgg tgagagctct   1440
aatttgcctt gggccagttt caggtttata ggcccccctca gtcttcagat acatgagggc   1500
ttctttgctc ttgtgatcgt gtagtcccat agctgtaaaa ccagaatcac caggaggttg   1560
cacctagtca ggaatattgg gaatggccta gaacaaggtg tttggcacat aagtagacca   1620
cttatccctc attgtgacct aattccagag catctggctg ggttgttggg ttctagactt   1680
tgtcctcacc tcccagtgac cctgactagc cacaggccat gagataccag ggggccgttc   1740
cttggatgga gcctgtggtt gatgcaaggc ttccttgtcc ccaagcaagt cttcagaagg   1800
ttagaaccca gtgttgactg agtctgtgct tgaaaccagg ccagagccat ggattaggaa   1860
gggcaaagag aaggcaccag aatgagtaaa gcaggcaggt ggtgaagcca accataaact   1920
tctcaggagt gacatgtgct tccttcaaag gcatttttgt taaccatatc cttctgagtt   1980
ctatgtttcc ttcacagctg ttctatccat tttgtggact gtcccccacc cccaccccat   2040
cattgttttt aaaaaattaa ggcctggcgc agcagctcat gcctataatc ccagcacttt   2100
gggaggctga ggcgggcgga tcacttgagg ccaggagttt gagaccagcc caggcaacat   2160
agcaaaaccc cattctgctt taaaaaaaaa aaaaaaaaaa attagcttgg cgtagtggca   2220
tgtgcctata atcccagcta ctggggaggc tgaggcacaa gaatcatttg aacctgggag   2280
gtagaggttg ctgtgagccg agattacgcc cctgcactcc agcctgggtc acagagtgag   2340
actccatctc agaaaaaaaa aaaattgagt caggtgcagt agctccttcc tgtagtccca   2400
gctacttggg aggctgaggc tagaggatca cttgagccca ggagtttgag tctagtctgg   2460
gcaacatagc aagaccccat ctctaaaatt taagtaagta aaagtagata aataaaaaga   2520
```

aaaaaaaact gtttatgtgc tcatcataaa gtagaagagt ggtttgcttt tttttttttt 2580
tttggattaa tgaggaaatc attctgtggc tctagtcata atttatgctt aataacattg 2640
atagtagccc tttgcgctat aactctacct aaagactcac atcatttggc agagagagag 2700
tcgttgaagt cccaggaatt caggactggg caggttaaga cctcagacaa ggtagtagag 2760
gtagacttgt ggacaaggct cgggtcccag cccaccgcac cccaacttta atcagagtgg 2820
ttcactattg atctattttt gtgtgatagc tgtgtggcgt gggccacaac atttaatgag 2880
aagttactgt gcaccaaact gccgaacacc attctaaact attcatatat attagtcatt 2940
taattcttac ataacttgag aggtagacag atatccttat tttagagatg aggaaaccaa 3000
gagaacttag gtcattagcg caaggttgta gagtaagcgg caaagccaag acacaaagct 3060
gggtggtttg gtttcagagc cagtgctttt cccctctact gtactgcctc tcaaccaaca 3120
cagggttgca caggcccatt ctctgatttt tttcctcttg tcctctgcct ctccctctag 3180
ctcccacttc ctctctgctc tagttcattt tctttagagc agcccgagtg atcatgaagt 3240
gcaaatcttg ccatgtcagt cccctgctta gaaccctcca atggctcact ttctctttag 3300
gcaaaagtct ttaccccatg ccttctccca tctcatctca accccctcat ttgttggctg 3360
tctgctgtca gccactcttc tttcaggtcc tcagatgcac tgcaccctct cctgcctggg 3420
ggtctttgct cctgctacta cctctgcttg aacagctcct caccttcctt cctccaaccc 3480
tacccttgta taggtgactt ttgttcatcc ttcagaattc aactcacatg tctcttgcat 3540
ggagaaccct cacctactgt gttgagaccc tgtccagccc ccaggtggga tcctctctcg 3600
acttcccata catttctttc acagcattta catagtccat gatagtttac ttgtgggatt 3660
atttggttaa tctttgcctt taacaccagg gttccttggg tgaaggagct tctttatctt 3720
ggtaacagca ttatttcaag cataacttgt aatatagtta tattacatat ataacatata 3780
tatatataac ataacatata taacatatat aacaagcata acttgttata tagtcttgta 3840
tatagtaaga cctcaataaa tatttggaga acaaaaaaaa aaaaa 3885

<210> SEQ ID NO 16
<211> LENGTH: 1050
<212> TYPE: DNA
<213> ORGANISM: Homo sapiens

<400> SEQUENCE: 16
ctctgagccc tgctcggttt aggcctgtct gcggaatccg caccaaccag caccatgccc 60
atgatactgg ggtactggga catccgcggg ctggcccacg ccatccgcct gctcctggaa 120
tacacagact caagctatga ggaaaagaag tacacgatgg gggacgctcc tgattatgac 180
agaagccagt ggctgaatga aaaattcaag ctgggcctgg actttcccaa tctgccctac 240
ttgattgatg gggctcacaa gatcacccag agcaacgcca tcttgtgcta cattgcccgc 300
aagcacaacc tgtgtgggga gacagaagag gagaagattc gtgtggacat tttggagaac 360
cagaccatgg acaaccatat gcagctgggc atgatctgct acaatccaga atttgagaaa 420
ctgaagccaa agtacttgga ggaactccct gaaaagctaa agctctactc agagtttctg 480
gggaagcggc catggtttgc aggaaacaag ggcttggaga agatctctgc ctacatgaag 540
tccagccgct tcctcccaag acctgtgttc tcaaagatgg ctgtctgggg caacaagtag 600
ggccttgaag gccaggaggt gggagtgagg agcccatact cagcctgctg cccaggctgt 660
gcagcgcagc tggactctgc atcccagcac ctgcctcctc gttcctttct cctgtttatt 720
cccatcttta ctcccaagac ttcattgtcc ctcttcactc cccctaaacc cctgtcccat 780

-continued gcaggccctt tgaagcctca gctacccact atccttcgtg aacatcccct cccatcatta 840
cccttccctg cactaaagcc agcctgacct tccttcctgt tagtggttgt gtctgcttta 900
aagggcctgc ctggcccctc gcctgtggag ctcagccccg agctgtcccc gtgttgcatg 960
aaggagcagc attgactggt ttacaggccc tgctcctgca gcatggtccc tgccttaggc 1020
ctacctgatg gaagtaaagc ctcaaccaca 1050

<210> SEQ ID NO 17
<211> LENGTH: 586
<212> TYPE: DNA
<213> ORGANISM: Homo sapiens

<400> SEQUENCE: 17
aaacactctg tgtggctcct cggctttgac agagtgcaag acgatgactt gcaaaatgtc 60
gcagctggaa cgcaacatag agaccatcat caacaccttc caccaatact ctgtgaagct 120
ggggcaccca gacaccctga accaggggga attcaaagag ctggtgcgaa aagatctgca 180
aaattttctc aagaaggaga ataagaatga aaaggtcata gaacacatca tggaggacct 240
ggacacaaat gcagacaagc agctgagctt cgaggagttc atcatgctga tggcgaggct 300
aacctgggcc tcccacgaga agatgcacga gggtgacgag ggccctggcc accaccataa 360
gccaggcctc ggggagggca ccccctaaga ccacagtggc caagatcaca gtggccacgg 420
ccacggccac agtcatggtg gccacggcca cagccactaa tcaggaggcc aggccaccct 480
gcctctaccc aaccagggcc ccggggcctg ttatgtcaaa ctgtcttggc tgtggggcta 540
ggggctgggg ccaaataaag tctcttcctc caagtcaaaa aaaaaa 586

<210> SEQ ID NO 18
<211> LENGTH: 1793
<212> TYPE: DNA
<213> ORGANISM: Homo sapiens

<400> SEQUENCE: 18
cgcgtccgcc ccgcgagcac agagcctcgc ctttgccgat ccgccgcccg tccacacccg 60
ccgccagctc accatggatg atgatatcgc cgcgctcgtc gtcgacaacg gctccggcat 120
gtgcaaggcc ggcttcgcgg gcgacgatgc cccccgggcc gtcttcccct ccatcgtggg 180
gcgccccagg caccagggcg tgatggtggg catgggtcag aaggattcct atgtgggcga 240
cgaggcccag agcaagagag gcatcctcac cctgaagtac cccatcgagc acggcatcgt 300
caccaactgg gacgacatgg agaaaatctg gcaccacacc ttctacaatg agctgcgtgt 360
ggctcccgag gagcaccccg tgctgctgac cgaggccccc ctgaacccca aggccaaccg 420
cgagaagatg acccagatca tgtttgagac cttcaacacc ccagccatgt acgttgctat 480
ccaggctgtg ctatccctgt acgcctctgg ccgtaccact ggcatcgtga tggactccgg 540
tgacggggtc acccacactg tgcccatcta cgaggggtat gccctccccc atgccatcct 600
gcgtctggac ctggctggcc gggacctgac tgactacctc atgaagatcc tcaccgagcg 660
cggctacagc ttcaccacca cggccgagcg ggaaatcgtg cgtgacatta aggagaagct 720
gtgctacgtc gccctggact tcgagcaaga gatggccacg gctgcttcca gctcctccct 780
ggagaagagc tacgagctgc ctgacggcca ggtcatcacc attggcaatg agcggttccg 840
ctgccctgag gcactcttcc agccttcctt cctgggcatg gagtcctgtg gcatccacga 900
aactaccttc aactccatca tgaagtgtga cgtggacatc cgcaaagacc tgtacgccaa 960
cacagtgctg tctggcggca ccaccatgta ccctggcatt gccgacagga tgcagaagga 1020

```
gatcactgcc ctggcaccca gcacaatgaa gatcaagatc attgctcctc ctgagcgcaa   1080

gtactccgtg tggatcggcg gctccatcct ggcctcgctg tccaccttcc agcagatgtg   1140

gatcagcaag caggagtatg acgagtccgg cccctccatc gtccaccgca aatgcttcta   1200

ggcggactat gacttagttg cgttacaccc tttcttgaca aaacctaact tgcgcagaaa   1260

acaagatgag attggcatgg ctttatttgt ttttttgtt ttgttttggt tttttttttt    1320

tttttggctt gactcaggat ttaaaaactg gaacggtgaa ggtgacagca gtcggttgga   1380

gcgagcatcc cccaaagttc acaatgtggc cgaggacttt gattgcacat tgttgttttt   1440

ttaatagtca ttccaaatat gagatgcatt gttacaggaa gtcccttgcc atcctaaaag   1500

ccaccccact tctctctaag gagaatggcc cagtcctctc ccaagtccac acaggggagg   1560

tgatagcatt gctttcgtgt aaattatgta atgcaaaatt tttttaatct tcgccttaat   1620

actttttat tttgttttat tttgaatgat gagccttcgt gcccccccctt ccccctttt   1680

gtcccccaac ttgagatgta tgaaggcttt tggtctccct gggagtgggt ggaggcagcc   1740

agggcttacc tgtacactga cttgagacca gttgaataaa agtgcacacc tta          1793
```

<210> SEQ ID NO 19
<211> LENGTH: 1310
<212> TYPE: DNA
<213> ORGANISM: Homo sapiens

<400> SEQUENCE: 19

```
aaattgagcc cgcagcctcc cgcttcgctc tctgctcctc ctgttcgaca gtcagccgca     60

tcttcttttg cgtcgccagc cgagccacat cgctcagaca ccatggggaa ggtgaaggtc    120

ggagtcaacg gatttggtcg tattgggcgc ctggtcacca gggctgcttt taactctggt    180

aaagtggata ttgttgccat caatgacccc ttcattgacc tcaactacat ggtttacatg    240

ttccaatatg attccaccca tggcaaattc catggcaccg tcaaggctga gaacgggaag    300

cttgtcatca atggaaatcc catcaccatc ttccaggagc gagatccctc caaaatcaag    360

tggggcgatg ctggcgctga gtacgtcgtg gagtccactg gcgtcttcac caccatggag    420

aaggctgggg ctcatttgca gggggggagcc aaaagggtca tcatctctgc cccctctgct    480

gatgccccca tgttcgtcat gggtgtgaac catgagaagt atgacaacag cctcaagatc    540

atcagcaatg cctcctgcac caccaactgc ttagcacccc tggccaaggt catccatgac    600

aactttggta tcgtggaagg actcatgacc acagtccatg ccatcactgc cacccagaag    660

actgtggatg gcccctccgg gaaactgtgg cgtgatggcc gcggggctct ccagaacatc    720

atccctgcct ctactggcgc tgccaaggct gtgggcaagg tcatccctga gctgaacggg    780

aagctcactg gcatggcctt ccgtgtcccc actgccaacg tgtcagtggt ggacctgacc    840

tgccgtctag aaaaacctgc caaatatgat gacatcaaga aggtggtgaa gcaggcgtcg    900

gagggccccc tcaagggcat cctgggctac actgagcacc aggtggtctc ctctgacttc    960

aacagcgaca cccactcctc cacctttgac gctggggctg gcattgccct caacgaccac   1020

tttgtcaagc tcatttcctg gtatgacaac gaatttggct acagcaacag ggtggtggac   1080

ctcatggccc acatggcctc caaggagtaa gacccctgga ccaccagccc cagcaagagc   1140

acaagaggaa gagagagacc ctcactgctg gggagtccct gccacactca gtcccccacc   1200

acactgaatc tcccctcctc acagttgcca tgtagacccc ttgaagaggg gaggggccta   1260

gggagccgca ccttgtcatg taccatcaat aaagtaccct gtgctcaacc              1310
```

<210> SEQ ID NO 20

<211> LENGTH: 2245
<212> TYPE: DNA
<213> ORGANISM: Homo sapiens

<400> SEQUENCE: 20

```
acgcgacccg ccctacgggc acctcccgcg cttttcttag cgccgcagac ggtggccgag     60
cgggggaccg ggaagcatgg cccgggggtc ggcggttgcc tgggcggcgc tcgggccgtt    120
gttgtggggc tgcgcgctgg ggctgcaggg cgggatgctg tacccccagg agagcccgtc    180
gcgggagtgc aaggagctgg acggcctctg gagcttccgc gccgacttct ctgacaaccg    240
acgccggggc ttcgaggagc agtggtaccg gcggccgctg tgggagtcag gccccaccgt    300
ggacatgcca gttccctcca gcttcaatga catcagccag gactggcgtc tgcggcattt    360
tgtcggctgg gtgtggtacg aacgggaggt gatcctgccg gagcgatgga cccaggacct    420
gcgcacaaga gtggtgctga ggattggcag tgcccattcc tatgccatcg tgtgggtgaa    480
tggggtcgac acgctagagc atgagggggg ctacctcccc ttcgaggccg acatcagcaa    540
cctggtccag gtggggcccc tgccctcccg gctccgaatc actatcgcca tcaacaacac    600
actcaccccc accaccctgc caccagggac catccaatac ctgactgaca cctccaagta    660
tcccaagggt tactttgtcc agaacacata ttttgacttt ttcaactacg ctggactgca    720
gcggtctgta cttctgtaca cgacacccac cacctacatc gatgacatca ccgtcaccac    780
cagcgtggag caagacagtg ggctggtgaa ttaccagatc tctgtcaagg gcagtaacct    840
gttcaagttg gaagtgcgtc ttttggatgc agaaaacaaa gtcgtggcga atgggactgg    900
gacccagggc caacttaagg tgccaggtgt cagcctctgg tggccgtacc tgatgcacga    960
acgccctgcc tatctgtatt cattggaggt gcagctgact gcacagacgt cactggggcc   1020
tgtgtctgac ttctacacac tccctgtggg gatccgcact gtggctgtca ccaagagcca   1080
gttcctcatc aatgggaaac ctttctattt ccacggtgtc aacaagcatg aggatgcgga   1140
catccgaggg aagggcttcg actggccgct gctggtgaag gacttcaacc tgcttcgctg   1200
gcttggtgcc aacgctttcc gtaccagcca ctacccctat gcagaggaag tgatgcagat   1260
gtgtgaccgc tatgggattg tggtcatcga tgagtgtccc ggcgtgggcc tggcgctgcc   1320
gcagttcttc aacaacgttt ctctgcatca ccacatgcag gtgatggaag aagtggtgcg   1380
tagggacaag aaccaccccg cggtcgtgat gtggtctgtg gccaacgagc ctgcgtccca   1440
cctagaatct gctggctact acttgaagat ggtgatcgct cacaccaaat ccttggaccc   1500
ctcccggcct gtgacctttg tgagcaactc taactatgca gcagacaagg gggctccgta   1560
tgtggatgtg atctgtttga acagctacta ctcttggtat cacgactacg ggcacctgga   1620
gttgattcag ctgcagctgg ccacccagtt tgagaactgg tataagaagt atcagaagcc   1680
cattattcag agcgagtatg gagcagaaac gattgcaggg tttcaccagg atccacctct   1740
gatgttcact gaagagtacc agaaaagtct gctagagcag taccatctgg gtctggatca   1800
aaaacgcaga aaatacgtgg ttggagagct catttggaat tttgccgatt tcatgactga   1860
acagtcaccg acgagagtgc tggggaataa aaaggggatc ttcactcggc agagacaacc   1920
aaaaagtgca gcgttccttt tgcgagagag atactggaag attgccaatg aaaccaggta   1980
tccccactca gtagccaagt cacaatgttt ggaaaacagc ccgtttactt gagcaagact   2040
gataccacct gcgtgtccct tcctccccga gtcagggcga cttccacagc agcagaacaa   2100
gtgcctcctg gactgttcac ggcagaccag aacgtttctg gcctgggttt tgtggtcatc   2160
tattctagca gggaacacta aaggtggaaa taaaagattt tctattatgg aaataaagag   2220
```

ttggcatgaa agtggctact gaaaa 2245

<210> SEQ ID NO 21
<211> LENGTH: 1229
<212> TYPE: DNA
<213> ORGANISM: Homo sapiens

<400> SEQUENCE: 21
gtctgacggg cgatggcgca gccaatagac aggagcgcta tccgcggttt ctgattggct 60
actttgttcg cattataaaa ggcacgcgcg ggcgcgaggc ccttctctcg ccaggcgtcc 120
tcgtggaagt gacatcgtct ttaaaccctg cgtggcaatc cctgacgcac cgccgtgatg 180
cccagggaag acagggcgac ctggaagtcc aactacttcc ttaagatcat ccaactattg 240
gatgattatc cgaaatgttt cattgtggga gcagacaatg tgggctccaa gcagatgcag 300
cagatccgca tgtcccttcg cgggaaggct gtggtgctga tgggcaagaa caccatgatg 360
cgcaaggcca tccgagggca cctggaaaac aacccagctc tggagaaact gctgcctcat 420
atccggggga atgtgggctt tgtgttcacc aaggaggacc tcactgagat cagggacatg 480
ttgctggcca ataaggtgcc agctgctgcc cgtgctggtg ccattgcccc atgtgaagtc 540
actgtgccag cccagaacac tggtctcggg cccgagaaga cctccttttt ccaggcttta 600
ggtatcacca ctaaaatctc caggggcacc attgaaatcc tgagtgatgt gcagctgatc 660
aagactggag acaaagtggg agccagcgaa gccacgctgc tgaacatgct caacatctcc 720
cccttctcct ttgggctggt catccagcag gtgttcgaca atggcagcat ctacaaccct 780
gaagtgcttg atatcacaga ggaaactctg cattctcgct tcctggaggg tgtccgcaat 840
gttgccagtg tctgtctgca gattggctac ccaactgttg catcagtacc ccattctatc 900
atcaacgggt acaaacgagt cctggccttg tctgtggaga cggattacac cttcccactt 960
gctgaaaagg tcaaggcctt cttggctgat ccatctgcct ttgtggctgc tgcccctgtg 1020
gctgctgcca ccacagctgc tcctgctgct gctgcagccc cagctaaggt tgaagccaag 1080
gaagagtcgg aggagtcgga cgaggatatg ggatttggtc tctttgacta atcaccaaaa 1140
agcaaccaac ttagccagtt ttatttgcaa aacaaggaaa taaaggctta cttctttaaa 1200
aagtaaaaaa aaaaaaaaaa aaaaaaaaa 1229

<210> SEQ ID NO 22
<211> LENGTH: 5010
<212> TYPE: DNA
<213> ORGANISM: Homo sapiens

<400> SEQUENCE: 22
ggcggctcgg gacggaggac gcgctagtgt gagtgcgggc ttctagaact acaccgaccc 60
tcgtgtcctc ccttcatcct gcggggctgg ctggagcggc cgctccggtg ctgtccagca 120
gccataggga gccgcacggg gagcgggaaa gcggtcgcgg ccccaggcgg ggcggccggg 180
atggagcggg gccgcgagcc tgtggggaag gggctgtggc ggcgcctcga gcggctgcag 240
gttcttctgt gtggcagttc agaatgatgg atcaagctag atcagcattc tctaacttgt 300
ttggtggaga accattgtca tatacccggt tcagcctggc tcggcaagta gatggcgata 360
acagtcatgt ggagatgaaa cttgctgtag atgaagaaga aaatgctgac aataacacaa 420
aggccaatgt cacaaaacca aaaaggtgta gtggaagtat ctgctatggg actattgctg 480
tgatcgtctt tttcttgatt ggatttatga ttggctactt gggctattgt aaaggggtag 540
aaccaaaaac tgagtgtgag agactggcag gaaccgagtc tccagtgagg gaggagccag 600

-continued

```
gagaggactt ccctgcagca cgtcgcttat attgggatga cctgaagaga aagttgtcgg    660
agaaactgga cagcacagac ttcaccagca ccatcaagct gctgaatgaa aattcatatg    720
tccctcgtga ggctggatct caaaaagatg aaaatcttgc gttgtatgtt gaaaatcaat    780
ttcgtgaatt taaactcagc aaagtctggc gtgatcaaca ttttgttaag attcaggtca    840
aagacagcgc tcaaaactcg gtgatcatag ttgataagaa cggtagactt gtttacctgg    900
tggagaatcc tgggggttat gtggcgtata gtaaggctgc aacagttact ggtaaactgg    960
tccatgctaa ttttggtact aaaaaagatt ttgaggattt atacactcct gtgaatggat   1020
ctatagtgat tgtcagagca gggaaaatca cctttgcaga aaaggttgca aatgctgaaa   1080
gcttaaatgc aattggtgtg ttgatataca tggaccagac taaatttccc attgttaacg   1140
cagaactttc attctttgga catgctcatc tggggacagg tgacccttac acacctggat   1200
tcccttcctt caatcacact cagtttccac catctcggtc atcaggattg cctaatatac   1260
ctgtccagac aatctccaga gctgctgcag aaaagctgtt tgggaatatg gaaggagact   1320
gtccctctga ctggaaaaca gactctacat gtaggatggt aacctcagaa agcaagaatg   1380
tgaagctcac tgtgagcaat gtgctgaaag agataaaaat tcttaacatc tttggagtta   1440
ttaaaggctt tgtagaacca gatcactatg ttgtagttgg ggcccagaga gatgcatggg   1500
gccctggagc tgcaaaatcc ggtgtaggca cagctctcct attgaaactt gcccagatgt   1560
tctcagatat ggtcttaaaa gatgggtttc agcccagcag aagcattatc tttgccagtt   1620
ggagtgctgg agactttgga tcggttggtg ccactgaatg gctagaggga tacctttcgt   1680
ccctgcattt aaaggctttc acttatatta atctggataa agcggttctt ggtaccagca   1740
acttcaaggt ttctgccagc ccactgttgt atacgcttat tgagaaaaca atgcaaaatg   1800
tgaagcatcc ggttactggg caatttctat atcaggacag caactgggcc agcaaagttg   1860
agaaactcac tttagacaat gctgctttcc ctttccttgc atattctgga atcccagcag   1920
tttctttctg tttttgcgag gacacagatt atccttattt gggtaccacc atggacacct   1980
ataaggaact gattgagagg attcctgagt tgaacaaagt ggcacgagca gctgcagagg   2040
tcgctggtca gttcgtgatt aaactaaccc atgatgttga attgaacctg gactatgaga   2100
ggtacaacag ccaactgctt tcatttgtga gggatctgaa ccaatacaga gcagacataa   2160
aggaaatggg cctgagttta cagtggctgt attctgctcg tggagacttc ttccgtgcta   2220
cttccagact aacaacagat ttcgggaatg ctgagaaaac agacagattt gtcatgaaga   2280
aactcaatga tcgtgtcatg agagtggagt atcacttcct ctctccctac gtatctccaa   2340
aagagtctcc tttccgacat gtcttctggg gctccggctc tcacacgctg ccagctttac   2400
tggagaactt gaaactgcgt aaacaaaata acggtgcttt taatgaaacg ctgttcagaa   2460
accagttggc tctagctact tggactattc agggagctgc aaatgccctc tctggtgacg   2520
tttgggacat tgacaatgag ttttaaatgt gatacccata gcttccatga gaacagcagg   2580
gtagtctggt ttctagactt gtgctgatcg tgctaaattt tcagtagggc tacaaaacct   2640
gatgttaaaa ttccatccca tcatcttggt actactagat gtctttaggc agcagctttt   2700
aatacagggt agataacctg tacttcaagt taaagtgaat aaccacttaa aaaatgtcca   2760
tgatggaata ttcccctatc tctagaattt taagtgcttt gtaatgggaa ctgcctcttt   2820
cctgttgttg ttaatgaaaa tgtcagaaac cagttatgtg aatgatctct ctgaatccta   2880
agggctggtc tctgctgaag gttgtaagtg gttcgcttac tttgagtgat cctccaactt   2940
catttgatgc taaataggag ataccaggtt gaaagacctc tccaaatgag atctaagcct   3000
```

-continued ttccataagg aatgtagcag gtttcctcat tcctgaaaga aacagttaac tttcagaaga 3060
gatgggcttg ttttcttgcc aatgaggtct gaaatggagg tccttctgct ggataaaatg 3120
aggttcaact gttgattgca ggaataaggc cttaatatgt taacctcagt gtcatttatg 3180
aaaagagggg accagaagcc aaagacttag tatattttct ttcctctgt cccttccccc 3240 ataagcctcc atttagttct ttgttatttt tgtttcttcc aaagcacatt gaaagagaac 3300
cagtttcagg tgtttagttg cagactcagt ttgtcagact ttaaagaata atatgctgcc 3360
aaattttggc caaagtgtta atcttagggg agagctttct gtccttttgg cactgagata 3420
tttattgttt atttatcagt gacagagttc actataaatg gtgttttttt aatagaatat 3480
aattatcgga agcagtgcct tccataatta tgacagttat actgtcggtt tttttaaat 3540 aaaagcagca tctgctaata aaacccaaca gatactggaa gttttgcatt tatggtcaac 3600
acttaagggt tttagaaaac agccgtcagc caaatgtaat tgaataaagt tgaagctaag 3660
atttagagat gaattaaatt taattagggg ttgctaagaa gcgagcactg accagataag 3720
aatgctggtt ttcctaaatg cagtgaattg tgaccaagtt ataaatcaat gtcacttaaa 3780
ggctgtggta gtactcctgc aaaattttat agctcagttt atccaaggtg taactctaat 3840
tcccatttgc aaaatttcca gtacctttgt cacaatccta acacattatc gggagcagtg 3900
tcttccataa tgtataaaga acaaggtagt ttttacctac cacagtgtct gtatcggaga 3960
cagtgatctc catatgttac actaagggtg taagtaatta tcgggaacag tgtttcccat 4020
aattttcttc atgcaatgac atcttcaaag cttgaagatc gttagtatct aacatgtatc 4080
ccaactccta taattcccta tcttttagtt ttagttgcag aaacattttg tggtcattaa 4140
gcattgggtg ggtaaattca accactgtaa aatgaaatta ctacaaaatt tgaaatttag 4200
cttgggtttt tgttaccttt atggtttctc caggtcctct acttaatgag atagcagcat 4260
acatttataa tgtttgctat tgacaagtca ttttaattta tcacattatt tgcatgttac 4320
ctcctataaa cttagtgcgg acaagtttta atccagaatt gaccttttga cttaaagcag 4380
agggactttg tatagaaggt ttgggggctg tggggaagga gagtcccctg aaggtctgac 4440
acgtctgcct acccattcgt ggtgatcaat taaatgtagg tatgaataag ttcgaagctc 4500
cgtgagtgaa ccatcatata aacgtgtagt acagctgttt gtcatagggc agttggaaac 4560
ggcctcctag ggaaaagttc atagggtctc ttcaggttct tagtgtcact tacctagatt 4620
tacagcctca cttgaatgtg tcactactca cagtctcttt aatcttcagt tttatcttta 4680
atctcctctt ttatcttgga ctgacattta gcgtagctaa gtgaaaaggt catagctgag 4740
attcctggtt cgggtgttac gcacacgtac ttaaatgaaa gcatgtggca tgttcatcgt 4800
ataacacaat atgaatacag ggcatgcatt ttgcagcagt gagtctcttc agaaaaccct 4860
tttctacagt tagggttgag ttacttccta tcaagccagt acgtgctaac aggctcaata 4920
ttcctgaatg aaatatcaga ctagtgacaa gctcctggtc ttgagatgtc ttctcgttaa 4980
ggagtagggc cttttggagg taaaggtata 5010

<210> SEQ ID NO 23
<211> LENGTH: 1255
<212> TYPE: PRT
<213> ORGANISM: Homo sapiens

<400> SEQUENCE: 23

Met Glu Leu Ala Ala Leu Cys Arg Trp Gly Leu Leu Leu Ala Leu Leu
1 5 10 15

Pro Pro Gly Ala Ala Ser Thr Gln Val Cys Thr Gly Thr Asp Met Lys

-continued

```
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445
```

-continued

```
Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880
```

```
Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
        995                 1000                1005

Leu Glu  Asp Asp Asp Met Gly  Asp Leu Val Asp Ala  Glu Glu Tyr
    1010                1015                1020

Leu Val  Pro Gln Gln Gly Phe  Phe Cys Pro Asp Pro  Ala Pro Gly
    1025                1030                1035

Ala Gly  Gly Met Val His His  Arg His Arg Ser Ser  Ser Thr Arg
    1040                1045                1050

Ser Gly  Gly Gly Asp Leu Thr  Leu Gly Leu Glu Pro  Ser Glu Glu
    1055                1060                1065

Glu Ala  Pro Arg Ser Pro Leu  Ala Pro Ser Glu Gly  Ala Gly Ser
    1070                1075                1080

Asp Val  Phe Asp Gly Asp Leu  Gly Met Gly Ala Ala  Lys Gly Leu
    1085                1090                1095

Gln Ser  Leu Pro Thr His Asp  Pro Ser Pro Leu Gln  Arg Tyr Ser
    1100                1105                1110

Glu Asp  Pro Thr Val Pro Leu  Pro Ser Glu Thr Asp  Gly Tyr Val
    1115                1120                1125

Ala Pro  Leu Thr Cys Ser Pro  Gln Pro Glu Tyr Val  Asn Gln Pro
    1130                1135                1140

Asp Val  Arg Pro Gln Pro Pro  Ser Pro Arg Glu Gly  Pro Leu Pro
    1145                1150                1155

Ala Ala  Arg Pro Ala Gly Ala  Thr Leu Glu Arg Pro  Lys Thr Leu
    1160                1165                1170

Ser Pro  Gly Lys Asn Gly Val  Val Lys Asp Val Phe  Ala Phe Gly
    1175                1180                1185

Gly Ala  Val Glu Asn Pro Glu  Tyr Leu Thr Pro Gln  Gly Gly Ala
    1190                1195                1200

Ala Pro  Gln Pro His Pro Pro  Pro Ala Phe Ser Pro  Ala Phe Asp
    1205                1210                1215

Asn Leu  Tyr Tyr Trp Asp Gln  Asp Pro Pro Glu Arg  Gly Ala Pro
    1220                1225                1230

Pro Ser  Thr Phe Lys Gly Thr  Pro Thr Ala Glu Asn  Pro Glu Tyr
    1235                1240                1245

Leu Gly  Leu Asp Val Pro Val
    1250                1255
```

<210> SEQ ID NO 24
<211> LENGTH: 532
<212> TYPE: PRT

<213> ORGANISM: Homo sapiens

<400> SEQUENCE: 24

```
Met Glu Leu Asp Leu Ser Pro Pro His Leu Ser Ser Ser Pro Glu Asp
1               5                   10                  15

Leu Cys Pro Ala Pro Gly Thr Pro Pro Gly Thr Pro Arg Pro Pro Asp
            20                  25                  30

Thr Pro Leu Pro Glu Glu Val Lys Arg Ser Gln Pro Leu Leu Ile Pro
        35                  40                  45

Thr Thr Gly Arg Lys Leu Arg Glu Glu Glu Arg Arg Ala Thr Ser Leu
    50                  55                  60

Pro Ser Ile Pro Asn Pro Phe Pro Glu Leu Cys Ser Pro Pro Ser Gln
65                  70                  75                  80

Ser Pro Ile Leu Gly Gly Pro Ser Ser Ala Arg Gly Leu Leu Pro Arg
                85                  90                  95

Asp Ala Ser Arg Pro His Val Val Lys Val Tyr Ser Glu Asp Gly Ala
            100                 105                 110

Cys Arg Ser Val Glu Val Ala Ala Gly Ala Thr Ala Arg His Val Cys
        115                 120                 125

Glu Met Leu Val Gln Arg Ala His Ala Leu Ser Asp Glu Thr Trp Gly
    130                 135                 140

Leu Val Glu Cys His Pro His Leu Ala Leu Glu Arg Gly Leu Glu Asp
145                 150                 155                 160

His Glu Ser Val Val Glu Val Gln Ala Ala Trp Pro Val Gly Gly Asp
                165                 170                 175

Ser Arg Phe Val Phe Arg Lys Asn Phe Ala Lys Tyr Glu Leu Phe Lys
            180                 185                 190

Ser Ser Pro His Ser Leu Phe Pro Glu Lys Met Val Ser Ser Cys Leu
        195                 200                 205

Asp Ala His Thr Gly Ile Ser His Glu Asp Leu Ile Gln Asn Phe Leu
    210                 215                 220

Asn Ala Gly Ser Phe Pro Glu Ile Gln Gly Phe Leu Gln Leu Arg Gly
225                 230                 235                 240

Ser Gly Arg Lys Leu Trp Lys Arg Phe Phe Cys Phe Leu Arg Arg Ser
                245                 250                 255

Gly Leu Tyr Tyr Ser Thr Lys Gly Thr Ser Lys Asp Pro Arg His Leu
            260                 265                 270

Gln Tyr Val Ala Asp Val Asn Glu Ser Asn Val Tyr Val Val Thr Gln
        275                 280                 285

Gly Arg Lys Leu Tyr Gly Met Pro Thr Asp Phe Gly Phe Cys Val Lys
    290                 295                 300

Pro Asn Lys Leu Arg Asn Gly His Lys Gly Leu Arg Ile Phe Cys Ser
305                 310                 315                 320

Glu Asp Glu Gln Ser Arg Thr Cys Trp Leu Ala Ala Phe Arg Leu Phe
                325                 330                 335

Lys Tyr Gly Val Gln Leu Tyr Lys Asn Tyr Gln Gln Ala Gln Ser Arg
            340                 345                 350

His Leu His Pro Ser Cys Leu Gly Ser Pro Pro Leu Arg Ser Ala Ser
        355                 360                 365

Asp Asn Thr Leu Val Ala Met Asp Phe Ser Gly His Ala Gly Arg Val
    370                 375                 380

Ile Glu Asn Pro Arg Glu Ala Leu Ser Val Ala Leu Glu Glu Ala Gln
385                 390                 395                 400

Ala Trp Arg Lys Lys Thr Asn His Arg Leu Ser Leu Pro Met Pro Ala
```

```
                405                 410                 415

Ser Gly Thr Ser Leu Ser Ala Ala Ile His Arg Thr Gln Leu Trp Phe
            420                 425                 430

His Gly Arg Ile Ser Arg Glu Glu Ser Gln Arg Leu Ile Gly Gln Gln
        435                 440                 445

Gly Leu Val Asp Gly Leu Phe Leu Val Arg Glu Ser Gln Arg Asn Pro
    450                 455                 460

Gln Gly Phe Val Leu Ser Leu Cys His Leu Gln Lys Val Lys His Tyr
465                 470                 475                 480

Leu Ile Leu Pro Ser Glu Glu Glu Gly Arg Leu Tyr Phe Ser Met Asp
                485                 490                 495

Asp Gly Gln Thr Arg Phe Thr Asp Leu Leu Gln Leu Val Glu Phe His
            500                 505                 510

Gln Leu Asn Arg Gly Ile Leu Pro Cys Leu Leu Arg His Cys Cys Thr
        515                 520                 525

Arg Val Ala Leu
    530


<210> SEQ ID NO 25
<211> LENGTH: 379
<212> TYPE: PRT
<213> ORGANISM: Homo sapiens

<400> SEQUENCE: 25

Met Ala Ala Ala Ala Ala Gln Gly Gly Gly Gly Gly Glu Pro Arg Arg
1               5                   10                  15

Thr Glu Gly Val Gly Pro Gly Val Pro Gly Glu Val Glu Met Val Lys
            20                  25                  30

Gly Gln Pro Phe Asp Val Gly Pro Arg Tyr Thr Gln Leu Gln Tyr Ile
        35                  40                  45

Gly Glu Gly Ala Tyr Gly Met Val Ser Ser Ala Tyr Asp His Val Arg
    50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
    130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
    210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
```

```
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
    290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Pro Val Ala Glu Glu Pro Phe Thr Phe Ala Met Glu Leu
            340                 345                 350

Asp Asp Leu Pro Lys Glu Arg Leu Lys Glu Leu Ile Phe Gln Glu Thr
        355                 360                 365

Ala Arg Phe Gln Pro Gly Val Leu Glu Ala Pro
    370                 375


<210> SEQ ID NO 26
<211> LENGTH: 384
<212> TYPE: PRT
<213> ORGANISM: Homo sapiens

<400> SEQUENCE: 26

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
            20                  25                  30

Gly Ser Gly Ala Gln Gly Ile Val Cys Ala Ala Tyr Asp Ala Ile Leu
        35                  40                  45

Glu Arg Asn Val Ala Ile Lys Lys Leu Ser Arg Pro Phe Gln Asn Gln
    50                  55                  60

Thr His Ala Lys Arg Ala Tyr Arg Glu Leu Val Leu Met Lys Cys Val
65                  70                  75                  80

Asn His Lys Asn Ile Ile Gly Leu Leu Asn Val Phe Thr Pro Gln Lys
                85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
        115                 120                 125

Ser Tyr Leu Leu Tyr Gln Met Leu Cys Gly Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Leu
        195                 200                 205

Trp Ser Val Gly Cys Ile Met Gly Glu Met Val Cys His Lys Ile Leu
    210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
```

```
                245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
        275                 280                 285

Leu Lys Ala Ser Gln Ala Arg Asp Leu Leu Ser Lys Met Leu Val Ile
    290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
        355                 360                 365

Asn Gly Val Ile Arg Gly Gln Pro Ser Pro Leu Ala Gln Val Gln Gln
    370                 375                 380


<210> SEQ ID NO 27
<211> LENGTH: 239
<212> TYPE: PRT
<213> ORGANISM: Homo sapiens

<400> SEQUENCE: 27

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235
```

<210> SEQ ID NO 28
<211> LENGTH: 433
<212> TYPE: PRT
<213> ORGANISM: Homo sapiens

<400> SEQUENCE: 28

Met Ser Gly Arg Pro Arg Thr Thr Ser Phe Ala Glu Ser Cys Lys Pro
1 5 10 15

Val Gln Gln Pro Ser Ala Phe Gly Ser Met Lys Val Ser Arg Asp Lys
20 25 30

Asp Gly Ser Lys Val Thr Thr Val Val Ala Thr Pro Gly Gln Gly Pro
35 40 45

Asp Arg Pro Gln Glu Val Ser Tyr Thr Asp Thr Lys Val Ile Gly Asn
50 55 60

Gly Ser Phe Gly Val Val Tyr Gln Ala Lys Leu Cys Asp Ser Gly Glu
65 70 75 80

Leu Val Ala Ile Lys Lys Val Leu Gln Asp Lys Arg Phe Lys Asn Arg
85 90 95

Glu Leu Gln Ile Met Arg Lys Leu Asp His Cys Asn Ile Val Arg Leu
100 105 110

Arg Tyr Phe Phe Tyr Ser Ser Gly Glu Lys Lys Asp Glu Val Tyr Leu
115 120 125

Asn Leu Val Leu Asp Tyr Val Pro Glu Thr Val Tyr Arg Val Ala Arg
130 135 140

His Tyr Ser Arg Ala Lys Gln Thr Leu Pro Val Ile Tyr Val Lys Leu
145 150 155 160

Tyr Met Tyr Gln Leu Phe Arg Ser Leu Ala Tyr Ile His Ser Phe Gly
165 170 175

Ile Cys His Arg Asp Ile Lys Pro Gln Asn Leu Leu Leu Asp Pro Asp
180 185 190

Thr Ala Val Leu Lys Leu Cys Asp Phe Gly Ser Ala Lys Gln Leu Val
195 200 205

Arg Gly Glu Pro Asn Val Ser Tyr Ile Cys Ser Arg Tyr Tyr Arg Ala
210 215 220

Pro Glu Leu Ile Phe Gly Ala Thr Asp Tyr Thr Ser Ser Ile Asp Val
225 230 235 240

Trp Ser Ala Gly Cys Val Leu Ala Glu Leu Leu Leu Gly Gln Pro Ile
245 250 255

Phe Pro Gly Asp Ser Gly Val Asp Gln Leu Val Glu Ile Ile Lys Val
260 265 270

Leu Gly Thr Pro Thr Arg Glu Gln Ile Arg Glu Met Asn Pro Asn Tyr
275 280 285

Thr Glu Phe Lys Phe Pro Gln Ile Lys Ala His Pro Trp Thr Lys Asp
290 295 300

Ser Ser Gly Thr Gly His Phe Thr Ser Gly Val Arg Val Phe Arg Pro
305 310 315 320

Arg Thr Pro Pro Glu Ala Ile Ala Leu Cys Ser Arg Leu Leu Glu Tyr
325 330 335

Thr Pro Thr Ala Arg Leu Thr Pro Leu Glu Ala Cys Ala His Ser Phe
340 345 350

Phe Asp Glu Leu Arg Asp Pro Asn Val Lys Leu Pro Asn Gly Arg Asp
355 360 365

Thr Pro Ala Leu Phe Asn Phe Thr Thr Gln Glu Leu Ser Ser Asn Pro
370 375 380

Pro Leu Ala Thr Ile Leu Ile Pro Pro His Ala Arg Ile Gln Ala Ala 385 390 395 400

Ala Ser Thr Pro Thr Asn Ala Thr Ala Ala Ser Asp Ala Asn Thr Gly
405 410 415

Asp Arg Gly Gln Thr Asn Asn Ala Ala Ser Ala Ser Ala Ser Asn Ser
420 425 430

Thr

<210> SEQ ID NO 29
<211> LENGTH: 488
<212> TYPE: PRT
<213> ORGANISM: Homo sapiens

<400> SEQUENCE: 29

Met Ala Pro Ala Ala Trp Leu Arg Ser Ala Ala Ala Arg Ala Leu Leu
1 5 10 15

Pro Pro Met Leu Leu Leu Leu Leu Gln Pro Pro Pro Leu Leu Ala Arg
20 25 30

Ala Leu Pro Pro Asp Ala His His Leu His Ala Glu Arg Arg Gly Pro
35 40 45

Gln Pro Trp His Ala Ala Leu Pro Ser Ser Pro Ala Pro Ala Pro Ala
50 55 60

Thr Gln Glu Ala Pro Arg Pro Ala Ser Ser Leu Arg Pro Pro Arg Cys
65 70 75 80

Gly Val Pro Asp Pro Ser Asp Gly Leu Ser Ala Arg Asn Arg Gln Lys
85 90 95

Arg Phe Val Leu Ser Gly Gly Arg Trp Glu Lys Thr Asp Leu Thr Tyr
100 105 110

Arg Ile Leu Arg Phe Pro Trp Gln Leu Val Gln Glu Gln Val Arg Gln
115 120 125

Thr Met Ala Glu Ala Leu Lys Val Trp Ser Asp Val Thr Pro Leu Thr
130 135 140

Phe Thr Glu Val His Glu Gly Arg Ala Asp Ile Met Ile Asp Phe Ala
145 150 155 160

Arg Tyr Trp His Gly Asp Asp Leu Pro Phe Asp Gly Pro Gly Gly Ile
165 170 175

Leu Ala His Ala Phe Phe Pro Lys Thr His Arg Glu Gly Asp Val His
180 185 190

Phe Asp Tyr Asp Glu Thr Trp Thr Ile Gly Asp Asp Gln Gly Thr Asp
195 200 205

Leu Leu Gln Val Ala Ala His Glu Phe Gly His Val Leu Gly Leu Gln
210 215 220

His Thr Thr Ala Ala Lys Ala Leu Met Ser Ala Phe Tyr Thr Phe Arg
225 230 235 240

Tyr Pro Leu Ser Leu Ser Pro Asp Asp Cys Arg Gly Val Gln His Leu
245 250 255

Tyr Gly Gln Pro Trp Pro Thr Val Thr Ser Arg Thr Pro Ala Leu Gly
260 265 270

Pro Gln Ala Gly Ile Asp Thr Asn Glu Ile Ala Pro Leu Glu Pro Asp
275 280 285

Ala Pro Pro Asp Ala Cys Glu Ala Ser Phe Asp Ala Val Ser Thr Ile
290 295 300

Arg Gly Glu Leu Phe Phe Phe Lys Ala Gly Phe Val Trp Arg Leu Arg
305 310 315 320

Gly Gly Gln Leu Gln Pro Gly Tyr Pro Ala Leu Ala Ser Arg His Trp
325 330 335

Gln Gly Leu Pro Ser Pro Val Asp Ala Ala Phe Glu Asp Ala Gln Gly
340 345 350

His Ile Trp Phe Phe Gln Gly Ala Gln Tyr Trp Val Tyr Asp Gly Glu
355 360 365

Lys Pro Val Leu Gly Pro Ala Pro Leu Thr Glu Leu Gly Leu Val Arg
370 375 380

Phe Pro Val His Ala Ala Leu Val Trp Gly Pro Glu Lys Asn Lys Ile
385 390 395 400

Tyr Phe Phe Arg Gly Arg Asp Tyr Trp Arg Phe His Pro Ser Thr Arg
405 410 415

Arg Val Asp Ser Pro Val Pro Arg Arg Ala Thr Asp Trp Arg Gly Val
420 425 430

Pro Ser Glu Ile Asp Ala Ala Phe Gln Asp Ala Asp Gly Tyr Ala Tyr
435 440 445

Phe Leu Arg Gly Arg Leu Tyr Trp Lys Phe Asp Pro Val Lys Val Lys
450 455 460

Ala Leu Glu Gly Phe Pro Arg Leu Val Gly Pro Asp Phe Phe Gly Cys
465 470 475 480

Ala Glu Pro Ala Asn Thr Phe Leu
485

<210> SEQ ID NO 30
<211> LENGTH: 334
<212> TYPE: PRT
<213> ORGANISM: Homo sapiens

<400> SEQUENCE: 30

Met Asn Leu Ser Leu Val Leu Ala Ala Phe Cys Leu Gly Ile Ala Ser
1 5 10 15

Ala Val Pro Lys Phe Asp Gln Asn Leu Asp Thr Lys Trp Tyr Gln Trp
20 25 30

Lys Ala Thr His Arg Arg Leu Tyr Gly Ala Asn Glu Glu Gly Trp Arg
35 40 45

Arg Ala Val Trp Glu Lys Asn Met Lys Met Ile Glu Leu His Asn Gly
50 55 60

Glu Tyr Ser Gln Gly Lys His Gly Phe Thr Met Ala Met Asn Ala Phe
65 70 75 80

Gly Asp Met Thr Asn Glu Glu Phe Arg Gln Met Met Gly Cys Phe Arg
85 90 95

Asn Gln Lys Phe Arg Lys Gly Lys Val Phe Arg Glu Pro Leu Phe Leu
100 105 110

Asp Leu Pro Lys Ser Val Asp Trp Arg Lys Lys Gly Tyr Val Thr Pro
115 120 125

Val Lys Asn Gln Lys Gln Cys Gly Ser Cys Trp Ala Phe Ser Ala Thr
130 135 140

Gly Ala Leu Glu Gly Gln Met Phe Arg Lys Thr Gly Lys Leu Val Ser
145 150 155 160

Leu Ser Glu Gln Asn Leu Val Asp Cys Ser Arg Pro Gln Gly Asn Gln
165 170 175

Gly Cys Asn Gly Gly Phe Met Ala Arg Ala Phe Gln Tyr Val Lys Glu
180 185 190

Asn Gly Gly Leu Asp Ser Glu Glu Ser Tyr Pro Tyr Val Ala Val Asp
195 200 205

Glu Ile Cys Lys Tyr Arg Pro Glu Asn Ser Val Ala Asn Asp Thr Gly
210 215 220

Phe Thr Val Val Ala Pro Gly Lys Glu Lys Ala Leu Met Lys Ala Val
225 230 235 240

Ala Thr Val Gly Pro Ile Ser Val Ala Met Asp Ala Gly His Ser Ser
245 250 255

Phe Gln Phe Tyr Lys Ser Gly Ile Tyr Phe Glu Pro Asp Cys Ser Ser
260 265 270

Lys Asn Leu Asp His Gly Val Leu Val Val Gly Tyr Gly Phe Glu Gly
275 280 285

Ala Asn Ser Asn Asn Ser Lys Tyr Trp Leu Val Lys Asn Ser Trp Gly
290 295 300

Pro Glu Trp Gly Ser Asn Gly Tyr Val Lys Ile Ala Lys Asp Lys Asn
305 310 315 320

Asn His Cys Gly Ile Ala Thr Ala Ala Ser Tyr Pro Asn Val
325 330

<210> SEQ ID NO 31
<211> LENGTH: 433
<212> TYPE: PRT
<213> ORGANISM: Homo sapiens

<400> SEQUENCE: 31

Met Ala Leu Arg Val Thr Arg Asn Ser Lys Ile Asn Ala Glu Asn Lys
1 5 10 15

Ala Lys Ile Asn Met Ala Gly Ala Lys Arg Val Pro Thr Ala Pro Ala
20 25 30

Ala Thr Ser Lys Pro Gly Leu Arg Pro Arg Thr Ala Leu Gly Asp Ile
35 40 45

Gly Asn Lys Val Ser Glu Gln Leu Gln Ala Lys Met Pro Met Lys Lys
50 55 60

Glu Ala Lys Pro Ser Ala Thr Gly Lys Val Ile Asp Lys Lys Leu Pro
65 70 75 80

Lys Pro Leu Glu Lys Val Pro Met Leu Val Pro Val Pro Val Ser Glu
85 90 95

Pro Val Pro Glu Pro Glu Pro Glu Pro Glu Pro Glu Pro Val Lys Glu
100 105 110

Glu Lys Leu Ser Pro Glu Pro Ile Leu Val Asp Thr Ala Ser Pro Ser
115 120 125

Pro Met Glu Thr Ser Gly Cys Ala Pro Ala Glu Glu Asp Leu Cys Gln
130 135 140

Ala Phe Ser Asp Val Ile Leu Ala Val Asn Asp Val Asp Ala Glu Asp
145 150 155 160

Gly Ala Asp Pro Asn Leu Cys Ser Glu Tyr Val Lys Asp Ile Tyr Ala
165 170 175

Tyr Leu Arg Gln Leu Glu Glu Glu Gln Ala Val Arg Pro Lys Tyr Leu
180 185 190

Leu Gly Arg Glu Val Thr Gly Asn Met Arg Ala Ile Leu Ile Asp Trp
195 200 205

Leu Val Gln Val Gln Met Lys Phe Arg Leu Leu Gln Glu Thr Met Tyr
210 215 220

Met Thr Val Ser Ile Ile Asp Arg Phe Met Gln Asn Asn Cys Val Pro
225 230 235 240

Lys Lys Met Leu Gln Leu Val Gly Val Thr Ala Met Phe Ile Ala Ser
245 250 255

Lys Tyr Glu Glu Met Tyr Pro Pro Glu Ile Gly Asp Phe Ala Phe Val
260 265 270

Thr Asp Asn Thr Tyr Thr Lys His Gln Ile Arg Gln Met Glu Met Lys
275 280 285

Ile Leu Arg Ala Leu Asn Phe Gly Leu Gly Arg Pro Leu Pro Leu His
290 295 300

Phe Leu Arg Arg Ala Ser Lys Ile Gly Glu Val Asp Val Glu Gln His
305 310 315 320

Thr Leu Ala Lys Tyr Leu Met Glu Leu Thr Met Leu Asp Tyr Asp Met
325 330 335

Val His Phe Pro Pro Ser Gln Ile Ala Ala Gly Ala Phe Cys Leu Ala
340 345 350

Leu Lys Ile Leu Asp Asn Gly Glu Trp Thr Pro Thr Leu Gln His Tyr
355 360 365

Leu Ser Tyr Thr Glu Glu Ser Leu Leu Pro Val Met Gln His Leu Ala
370 375 380

Lys Asn Val Val Met Val Asn Gln Gly Leu Thr Lys His Met Thr Val
385 390 395 400

Lys Asn Lys Tyr Ala Thr Ser Lys His Ala Lys Ile Ser Thr Leu Pro
405 410 415

Gln Leu Asn Ser Ala Leu Val Gln Asp Leu Ala Lys Ala Val Ala Lys
420 425 430

Val

<210> SEQ ID NO 32
<211> LENGTH: 142
<212> TYPE: PRT
<213> ORGANISM: Homo sapiens

<400> SEQUENCE: 32

Met Gly Ala Pro Thr Leu Pro Pro Ala Trp Gln Pro Phe Leu Lys Asp
1 5 10 15

His Arg Ile Ser Thr Phe Lys Asn Trp Pro Phe Leu Glu Gly Cys Ala
20 25 30

Cys Thr Pro Glu Arg Met Ala Glu Ala Gly Phe Ile His Cys Pro Thr
35 40 45

Glu Asn Glu Pro Asp Leu Ala Gln Cys Phe Phe Cys Phe Lys Glu Leu
50 55 60

Glu Gly Trp Glu Pro Asp Asp Asp Pro Ile Glu Glu His Lys Lys His
65 70 75 80

Ser Ser Gly Cys Ala Phe Leu Ser Val Lys Lys Gln Phe Glu Glu Leu
85 90 95

Thr Leu Gly Glu Phe Leu Lys Leu Asp Arg Glu Arg Ala Lys Asn Lys
100 105 110

Ile Ala Lys Glu Thr Asn Asn Lys Lys Lys Glu Phe Glu Glu Thr Ala
115 120 125

Glu Lys Val Arg Arg Ala Ile Glu Gln Leu Ala Ala Met Asp
130 135 140

<210> SEQ ID NO 33
<211> LENGTH: 3256
<212> TYPE: PRT
<213> ORGANISM: Homo sapiens

<400> SEQUENCE: 33

Met Trp Pro Thr Arg Arg Leu Val Thr Ile Lys Arg Ser Gly Val Asp
1 5 10 15

Gly Pro His Phe Pro Leu Ser Leu Ser Thr Cys Leu Phe Gly Arg Gly

```
            20                  25                  30

Ile Glu Cys Asp Ile Arg Ile Gln Leu Pro Val Val Ser Lys Gln His
        35                  40                  45

Cys Lys Ile Glu Ile His Glu Gln Glu Ala Ile Leu His Asn Phe Ser
    50                  55                  60

Ser Thr Asn Pro Thr Gln Val Asn Gly Ser Val Ile Asp Glu Pro Val
65                  70                  75                  80

Arg Leu Lys His Gly Asp Val Ile Thr Ile Ile Asp Arg Ser Phe Arg
                85                  90                  95

Tyr Glu Asn Glu Ser Leu Gln Asn Gly Arg Lys Ser Thr Glu Phe Pro
            100                 105                 110

Arg Lys Ile Arg Glu Gln Glu Pro Ala Arg Arg Val Ser Arg Ser Ser
        115                 120                 125

Phe Ser Ser Asp Pro Asp Glu Lys Ala Gln Asp Ser Lys Ala Tyr Ser
    130                 135                 140

Lys Ile Thr Glu Gly Lys Val Ser Gly Asn Pro Gln Val His Ile Lys
145                 150                 155                 160

Asn Val Lys Glu Asp Ser Thr Ala Asp Asp Ser Lys Asp Ser Val Ala
                165                 170                 175

Gln Gly Thr Thr Asn Val His Ser Ser Glu His Ala Gly Arg Asn Gly
            180                 185                 190

Arg Asn Ala Ala Asp Pro Ile Ser Gly Asp Phe Lys Glu Ile Ser Ser
        195                 200                 205

Val Lys Leu Val Ser Arg Tyr Gly Glu Leu Lys Ser Val Pro Thr Thr
    210                 215                 220

Gln Cys Leu Asp Asn Ser Lys Lys Asn Glu Ser Pro Phe Trp Lys Leu
225                 230                 235                 240

Tyr Glu Ser Val Lys Lys Glu Leu Asp Val Lys Ser Gln Lys Glu Asn
                245                 250                 255

Val Leu Gln Tyr Cys Arg Lys Ser Gly Leu Gln Thr Asp Tyr Ala Thr
            260                 265                 270

Glu Lys Glu Ser Ala Asp Gly Leu Gln Gly Glu Thr Gln Leu Leu Val
        275                 280                 285

Ser Arg Lys Ser Arg Pro Lys Ser Gly Gly Ser Gly His Ala Val Ala
    290                 295                 300

Glu Pro Ala Ser Pro Glu Gln Glu Leu Asp Gln Asn Lys Gly Lys Gly
305                 310                 315                 320

Arg Asp Val Glu Ser Val Gln Thr Pro Ser Lys Ala Val Gly Ala Ser
                325                 330                 335

Phe Pro Leu Tyr Glu Pro Ala Lys Met Lys Thr Pro Val Gln Tyr Ser
            340                 345                 350

Gln Gln Gln Asn Ser Pro Gln Lys His Lys Asn Lys Asp Leu Tyr Thr
        355                 360                 365

Thr Gly Arg Arg Glu Ser Val Asn Leu Gly Lys Ser Glu Gly Phe Lys
    370                 375                 380

Ala Gly Asp Lys Thr Leu Thr Pro Arg Lys Leu Ser Thr Arg Asn Arg
385                 390                 395                 400

Thr Pro Ala Lys Val Glu Asp Ala Ala Asp Ser Ala Thr Lys Pro Glu
                405                 410                 415

Asn Leu Ser Ser Lys Thr Arg Gly Ser Ile Pro Thr Asp Val Glu Val
            420                 425                 430

Leu Pro Thr Glu Thr Glu Ile His Asn Glu Pro Phe Leu Thr Leu Trp
        435                 440                 445
```

-continued

```
Leu Thr Gln Val Glu Arg Lys Ile Gln Lys Asp Ser Leu Ser Lys Pro
    450                 455                 460

Glu Lys Leu Gly Thr Thr Ala Gly Gln Met Cys Ser Gly Leu Pro Gly
465                 470                 475                 480

Leu Ser Ser Val Asp Ile Asn Asn Phe Gly Asp Ser Ile Asn Glu Ser
                485                 490                 495

Glu Gly Ile Pro Leu Lys Arg Arg Arg Val Ser Phe Gly Gly His Leu
            500                 505                 510

Arg Pro Glu Leu Phe Asp Glu Asn Leu Pro Pro Asn Thr Pro Leu Lys
        515                 520                 525

Arg Gly Glu Ala Pro Thr Lys Arg Lys Ser Leu Val Met His Thr Pro
    530                 535                 540

Pro Val Leu Lys Lys Ile Ile Lys Glu Gln Pro Gln Pro Ser Gly Lys
545                 550                 555                 560

Gln Glu Ser Gly Ser Glu Ile His Val Glu Val Lys Ala Gln Ser Leu
                565                 570                 575

Val Ile Ser Pro Pro Ala Pro Ser Pro Arg Lys Thr Pro Val Ala Ser
            580                 585                 590

Asp Gln Arg Arg Arg Ser Cys Lys Thr Ala Pro Ala Ser Ser Ser Lys
        595                 600                 605

Ser Gln Thr Glu Val Pro Lys Arg Gly Gly Arg Lys Ser Gly Asn Leu
    610                 615                 620

Pro Ser Lys Arg Val Ser Ile Ser Arg Ser Gln His Asp Ile Leu Gln
625                 630                 635                 640

Met Ile Cys Ser Lys Arg Arg Ser Gly Ala Ser Glu Ala Asn Leu Ile
                645                 650                 655

Val Ala Lys Ser Trp Ala Asp Val Val Lys Leu Gly Ala Lys Gln Thr
            660                 665                 670

Gln Thr Lys Val Ile Lys His Gly Pro Gln Arg Ser Met Asn Lys Arg
        675                 680                 685

Gln Arg Arg Pro Ala Thr Pro Lys Lys Pro Val Gly Glu Val His Ser
    690                 695                 700

Gln Phe Ser Thr Gly His Ala Asn Ser Pro Cys Thr Ile Ile Ile Gly
705                 710                 715                 720

Lys Ala His Thr Glu Lys Val His Val Pro Ala Arg Pro Tyr Arg Val
                725                 730                 735

Leu Asn Asn Phe Ile Ser Asn Gln Lys Met Asp Phe Lys Glu Asp Leu
            740                 745                 750

Ser Gly Ile Ala Glu Met Phe Lys Thr Pro Val Lys Glu Gln Pro Gln
        755                 760                 765

Leu Thr Ser Thr Cys His Ile Ala Ile Ser Asn Ser Glu Asn Leu Leu
    770                 775                 780

Gly Lys Gln Phe Gln Gly Thr Asp Ser Gly Glu Glu Pro Leu Leu Pro
785                 790                 795                 800

Thr Ser Glu Ser Phe Gly Gly Asn Val Phe Phe Ser Ala Gln Asn Ala
                805                 810                 815

Ala Lys Gln Pro Ser Asp Lys Cys Ser Ala Ser Pro Pro Leu Arg Arg
            820                 825                 830

Gln Cys Ile Arg Glu Asn Gly Asn Val Ala Lys Thr Pro Arg Asn Thr
        835                 840                 845

Tyr Lys Met Thr Ser Leu Glu Thr Lys Thr Ser Asp Thr Glu Thr Glu
    850                 855                 860

Pro Ser Lys Thr Val Ser Thr Ala Asn Arg Ser Gly Arg Ser Thr Glu
865                 870                 875                 880
```

```
Phe Arg Asn Ile Gln Lys Leu Pro Val Glu Ser Lys Ser Glu Glu Thr
                885                 890                 895

Asn Thr Glu Ile Val Glu Cys Ile Leu Lys Arg Gly Gln Lys Ala Thr
            900                 905                 910

Leu Leu Gln Gln Arg Arg Glu Gly Glu Met Lys Glu Ile Glu Arg Pro
        915                 920                 925

Phe Glu Thr Tyr Lys Glu Asn Ile Glu Leu Lys Glu Asn Asp Glu Lys
    930                 935                 940

Met Lys Ala Met Lys Arg Ser Arg Thr Trp Gly Gln Lys Cys Ala Pro
945                 950                 955                 960

Met Ser Asp Leu Thr Asp Leu Lys Ser Leu Pro Asp Thr Glu Leu Met
                965                 970                 975

Lys Asp Thr Ala Arg Gly Gln Asn Leu Leu Gln Thr Gln Asp His Ala
            980                 985                 990

Lys Ala Pro Lys Ser Glu Lys Gly  Lys Ile Thr Lys Met  Pro Cys Gln
        995                 1000                1005

Ser Leu  Gln Pro Glu Pro Ile  Asn Thr Pro Thr His  Thr Lys Gln
    1010                1015                1020

Gln Leu  Lys Ala Ser Leu Gly  Lys Val Gly Val Lys  Glu Glu Leu
    1025                1030                1035

Leu Ala  Val Gly Lys Phe Thr  Arg Thr Ser Gly Glu  Thr Thr His
    1040                1045                1050

Thr His  Arg Glu Pro Ala Gly  Asp Gly Lys Ser Ile  Arg Thr Phe
    1055                1060                1065

Lys Glu  Ser Pro Lys Gln Ile  Leu Asp Pro Ala Ala  Arg Val Thr
    1070                1075                1080

Gly Met  Lys Lys Trp Pro Arg  Thr Pro Lys Glu Glu  Ala Gln Ser
    1085                1090                1095

Leu Glu  Asp Leu Ala Gly Phe  Lys Glu Leu Phe Gln  Thr Pro Gly
    1100                1105                1110

Pro Ser  Glu Glu Ser Met Thr  Asp Glu Lys Thr Thr  Lys Ile Ala
    1115                1120                1125

Cys Lys  Ser Pro Pro Pro Glu  Ser Val Asp Thr Pro  Thr Ser Thr
    1130                1135                1140

Lys Gln  Trp Pro Lys Arg Ser  Leu Arg Lys Ala Asp  Val Glu Glu
    1145                1150                1155

Glu Phe  Leu Ala Leu Arg Lys  Leu Thr Pro Ser Ala  Gly Lys Ala
    1160                1165                1170

Met Leu  Thr Pro Lys Pro Ala  Gly Gly Asp Glu Lys  Asp Ile Lys
    1175                1180                1185

Ala Phe  Met Gly Thr Pro Val  Gln Lys Leu Asp Leu  Ala Gly Thr
    1190                1195                1200

Leu Pro  Gly Ser Lys Arg Gln  Leu Gln Thr Pro Lys  Glu Lys Ala
    1205                1210                1215

Gln Ala  Leu Glu Asp Leu Ala  Gly Phe Lys Glu Leu  Phe Gln Thr
    1220                1225                1230

Pro Gly  His Thr Glu Glu Leu  Val Ala Ala Gly Lys  Thr Thr Lys
    1235                1240                1245

Ile Pro  Cys Asp Ser Pro Gln  Ser Asp Pro Val Asp  Thr Pro Thr
    1250                1255                1260

Ser Thr  Lys Gln Arg Pro Lys  Arg Ser Ile Arg Lys  Ala Asp Val
    1265                1270                1275

Glu Gly  Glu Leu Leu Ala Cys  Arg Asn Leu Met Pro  Ser Ala Gly
```

-continued

```
    1280                1285                1290

Lys Ala  Met His Thr Pro Lys  Pro Ser Val Gly Glu  Glu Lys Asp
    1295                1300                1305

Ile Ile  Ile Phe Val Gly Thr  Pro Val Gln Lys Leu  Asp Leu Thr
    1310                1315                1320

Glu Asn  Leu Thr Gly Ser Lys  Arg Arg Pro Gln Thr  Pro Lys Glu
    1325                1330                1335

Glu Ala  Gln Ala Leu Glu Asp  Leu Thr Gly Phe Lys  Glu Leu Phe
    1340                1345                1350

Gln Thr  Pro Gly His Thr Glu  Glu Ala Val Ala Ala  Gly Lys Thr
    1355                1360                1365

Thr Lys  Met Pro Cys Glu Ser  Ser Pro Pro Glu Ser  Ala Asp Thr
    1370                1375                1380

Pro Thr  Ser Thr Arg Arg Gln  Pro Lys Thr Pro Leu  Glu Lys Arg
    1385                1390                1395

Asp Val  Gln Lys Glu Leu Ser  Ala Leu Lys Lys Leu  Thr Gln Thr
    1400                1405                1410

Ser Gly  Glu Thr Thr His Thr  Asp Lys Val Pro Gly  Gly Glu Asp
    1415                1420                1425

Lys Ser  Ile Asn Ala Phe Arg  Glu Thr Ala Lys Gln  Lys Leu Asp
    1430                1435                1440

Pro Ala  Ala Ser Val Thr Gly  Ser Lys Arg His Pro  Lys Thr Lys
    1445                1450                1455

Glu Lys  Ala Gln Pro Leu Glu  Asp Leu Ala Gly Leu  Lys Glu Leu
    1460                1465                1470

Phe Gln  Thr Pro Val Cys Thr  Asp Lys Pro Thr Thr  His Glu Lys
    1475                1480                1485

Thr Thr  Lys Ile Ala Cys Arg  Ser Gln Pro Asp Pro  Val Asp Thr
    1490                1495                1500

Pro Thr  Ser Ser Lys Pro Gln  Ser Lys Arg Ser Leu  Arg Lys Val
    1505                1510                1515

Asp Val  Glu Glu Glu Phe Phe  Ala Leu Arg Lys Arg  Thr Pro Ser
    1520                1525                1530

Ala Gly  Lys Ala Met His Thr  Pro Lys Pro Ala Val  Ser Gly Glu
    1535                1540                1545

Lys Asn  Ile Tyr Ala Phe Met  Gly Thr Pro Val Gln  Lys Leu Asp
    1550                1555                1560

Leu Thr  Glu Asn Leu Thr Gly  Ser Lys Arg Arg Leu  Gln Thr Pro
    1565                1570                1575

Lys Glu  Lys Ala Gln Ala Leu  Glu Asp Leu Ala Gly  Phe Lys Glu
    1580                1585                1590

Leu Phe  Gln Thr Arg Gly His  Thr Glu Glu Ser Met  Thr Asn Asp
    1595                1600                1605

Lys Thr  Ala Lys Val Ala Cys  Lys Ser Ser Gln Pro  Asp Pro Asp
    1610                1615                1620

Lys Asn  Pro Ala Ser Ser Lys  Arg Arg Leu Lys Thr  Ser Leu Gly
    1625                1630                1635

Lys Val  Gly Val Lys Glu Glu  Leu Leu Ala Val Gly  Lys Leu Thr
    1640                1645                1650

Gln Thr  Ser Gly Glu Thr Thr  His Thr His Thr Glu  Pro Thr Gly
    1655                1660                1665

Asp Gly  Lys Ser Met Lys Ala  Phe Met Glu Ser Pro  Lys Gln Ile
    1670                1675                1680
```

Leu Asp Ser Ala Ala Ser Leu Thr Gly Ser Lys Arg Gln Leu Arg
1685 1690 1695

Thr Pro Lys Gly Lys Ser Glu Val Pro Glu Asp Leu Ala Gly Phe
1700 1705 1710

Ile Glu Leu Phe Gln Thr Pro Ser His Thr Lys Glu Ser Met Thr
1715 1720 1725

Asn Glu Lys Thr Thr Lys Val Ser Tyr Arg Ala Ser Gln Pro Asp
1730 1735 1740

Leu Val Asp Thr Pro Thr Ser Ser Lys Pro Gln Pro Lys Arg Ser
1745 1750 1755

Leu Arg Lys Ala Asp Thr Glu Glu Glu Phe Leu Ala Phe Arg Lys
1760 1765 1770

Gln Thr Pro Ser Ala Gly Lys Ala Met His Thr Pro Lys Pro Ala
1775 1780 1785

Val Gly Glu Glu Lys Asp Ile Asn Thr Phe Leu Gly Thr Pro Val
1790 1795 1800

Gln Lys Leu Asp Gln Pro Gly Asn Leu Pro Gly Ser Asn Arg Arg
1805 1810 1815

Leu Gln Thr Arg Lys Glu Lys Ala Gln Ala Leu Glu Glu Leu Thr
1820 1825 1830

Gly Phe Arg Glu Leu Phe Gln Thr Pro Cys Thr Asp Asn Pro Thr
1835 1840 1845

Thr Asp Glu Lys Thr Thr Lys Lys Ile Leu Cys Lys Ser Pro Gln
1850 1855 1860

Ser Asp Pro Ala Asp Thr Pro Thr Asn Thr Lys Gln Arg Pro Lys
1865 1870 1875

Arg Ser Leu Lys Lys Ala Asp Val Glu Glu Glu Phe Leu Ala Phe
1880 1885 1890

Arg Lys Leu Thr Pro Ser Ala Gly Lys Ala Met His Thr Pro Lys
1895 1900 1905

Ala Ala Val Gly Glu Glu Lys Asp Ile Asn Thr Phe Val Gly Thr
1910 1915 1920

Pro Val Glu Lys Leu Asp Leu Leu Gly Asn Leu Pro Gly Ser Lys
1925 1930 1935

Arg Arg Pro Gln Thr Pro Lys Glu Lys Ala Lys Ala Leu Glu Asp
1940 1945 1950

Leu Ala Gly Phe Lys Glu Leu Phe Gln Thr Pro Gly His Thr Glu
1955 1960 1965

Glu Ser Met Thr Asp Asp Lys Ile Thr Glu Val Ser Cys Lys Ser
1970 1975 1980

Pro Gln Pro Asp Pro Val Lys Thr Pro Thr Ser Ser Lys Gln Arg
1985 1990 1995

Leu Lys Ile Ser Leu Gly Lys Val Gly Val Lys Glu Glu Val Leu
2000 2005 2010

Pro Val Gly Lys Leu Thr Gln Thr Ser Gly Lys Thr Thr Gln Thr
2015 2020 2025

His Arg Glu Thr Ala Gly Asp Gly Lys Ser Ile Lys Ala Phe Lys
2030 2035 2040

Glu Ser Ala Lys Gln Met Leu Asp Pro Ala Asn Tyr Gly Thr Gly
2045 2050 2055

Met Glu Arg Trp Pro Arg Thr Pro Lys Glu Glu Ala Gln Ser Leu
2060 2065 2070

Glu Asp Leu Ala Gly Phe Lys Glu Leu Phe Gln Thr Pro Asp His
2075 2080 2085

```
Thr Glu  Glu Ser Thr Thr Asp  Asp Lys Thr Thr Lys  Ile Ala Cys
    2090                 2095                 2100

Lys Ser  Pro Pro Pro Glu Ser  Met Asp Thr Pro Thr  Ser Thr Arg
    2105                 2110                 2115

Arg Arg  Pro Lys Thr Pro Leu  Gly Lys Arg Asp Ile  Val Glu Glu
    2120                 2125                 2130

Leu Ser  Ala Leu Lys Gln Leu  Thr Gln Thr Thr His  Thr Asp Lys
    2135                 2140                 2145

Val Pro  Gly Asp Glu Asp Lys  Gly Ile Asn Val Phe  Arg Glu Thr
    2150                 2155                 2160

Ala Lys  Gln Lys Leu Asp Pro  Ala Ala Ser Val Thr  Gly Ser Lys
    2165                 2170                 2175

Arg Gln  Pro Arg Thr Pro Lys  Gly Lys Ala Gln Pro  Leu Glu Asp
    2180                 2185                 2190

Leu Ala  Gly Leu Lys Glu Leu  Phe Gln Thr Pro Ile  Cys Thr Asp
    2195                 2200                 2205

Lys Pro  Thr Thr His Glu Lys  Thr Thr Lys Ile Ala  Cys Arg Ser
    2210                 2215                 2220

Pro Gln  Pro Asp Pro Val Gly  Thr Pro Thr Ile Phe  Lys Pro Gln
    2225                 2230                 2235

Ser Lys  Arg Ser Leu Arg Lys  Ala Asp Val Glu Glu  Glu Ser Leu
    2240                 2245                 2250

Ala Leu  Arg Lys Arg Thr Pro  Ser Val Gly Lys Ala  Met Asp Thr
    2255                 2260                 2265

Pro Lys  Pro Ala Gly Gly Asp  Glu Lys Asp Met Lys  Ala Phe Met
    2270                 2275                 2280

Gly Thr  Pro Val Gln Lys Leu  Asp Leu Pro Gly Asn  Leu Pro Gly
    2285                 2290                 2295

Ser Lys  Arg Trp Pro Gln Thr  Pro Lys Glu Lys Ala  Gln Ala Leu
    2300                 2305                 2310

Glu Asp  Leu Ala Gly Phe Lys  Glu Leu Phe Gln Thr  Pro Gly Thr
    2315                 2320                 2325

Asp Lys  Pro Thr Thr Asp Glu  Lys Thr Thr Lys Ile  Ala Cys Lys
    2330                 2335                 2340

Ser Pro  Gln Pro Asp Pro Val  Asp Thr Pro Ala Ser  Thr Lys Gln
    2345                 2350                 2355

Arg Pro  Lys Arg Asn Leu Arg  Lys Ala Asp Val Glu  Glu Glu Phe
    2360                 2365                 2370

Leu Ala  Leu Arg Lys Arg Thr  Pro Ser Ala Gly Lys  Ala Met Asp
    2375                 2380                 2385

Thr Pro  Lys Pro Ala Val Ser  Asp Glu Lys Asn Ile  Asn Thr Phe
    2390                 2395                 2400

Val Glu  Thr Pro Val Gln Lys  Leu Asp Leu Leu Gly  Asn Leu Pro
    2405                 2410                 2415

Gly Ser  Lys Arg Gln Pro Gln  Thr Pro Lys Glu Lys  Ala Glu Ala
    2420                 2425                 2430

Leu Glu  Asp Leu Val Gly Phe  Lys Glu Leu Phe Gln  Thr Pro Gly
    2435                 2440                 2445

His Thr  Glu Glu Ser Met Thr  Asp Asp Lys Ile Thr  Glu Val Ser
    2450                 2455                 2460

Cys Lys  Ser Pro Gln Pro Glu  Ser Phe Lys Thr Ser  Arg Ser Ser
    2465                 2470                 2475

Lys Gln  Arg Leu Lys Ile Pro  Leu Val Lys Val Asp  Met Lys Glu
```

```
    2480                2485                2490

Glu Pro  Leu Ala Val Ser Lys  Leu Thr Arg Thr Ser  Gly Glu Thr
    2495                2500                2505

Thr Gln  Thr His Thr Glu Pro  Thr Gly Asp Ser Lys  Ser Ile Lys
    2510                2515                2520

Ala Phe  Lys Glu Ser Pro Lys  Gln Ile Leu Asp Pro  Ala Ala Ser
    2525                2530                2535

Val Thr  Gly Ser Arg Arg Gln  Leu Arg Thr Arg Lys  Glu Lys Ala
    2540                2545                2550

Arg Ala  Leu Glu Asp Leu Val  Asp Phe Lys Glu Leu  Phe Ser Ala
    2555                2560                2565

Pro Gly  His Thr Glu Glu Ser  Met Thr Ile Asp Lys  Asn Thr Lys
    2570                2575                2580

Ile Pro  Cys Lys Ser Pro Pro  Pro Glu Leu Thr Asp  Thr Ala Thr
    2585                2590                2595

Ser Thr  Lys Arg Cys Pro Lys  Thr Arg Pro Arg Lys  Glu Val Lys
    2600                2605                2610

Glu Glu  Leu Ser Ala Val Glu  Arg Leu Thr Gln Thr  Ser Gly Gln
    2615                2620                2625

Ser Thr  His Thr His Lys Glu  Pro Ala Ser Gly Asp  Glu Gly Ile
    2630                2635                2640

Lys Val  Leu Lys Gln Arg Ala  Lys Lys Lys Pro Asn  Pro Val Glu
    2645                2650                2655

Glu Glu  Pro Ser Arg Arg Arg  Pro Arg Ala Pro Lys  Glu Lys Ala
    2660                2665                2670

Gln Pro  Leu Glu Asp Leu Ala  Gly Phe Thr Glu Leu  Ser Glu Thr
    2675                2680                2685

Ser Gly  His Thr Gln Glu Ser  Leu Thr Ala Gly Lys  Ala Thr Lys
    2690                2695                2700

Ile Pro  Cys Glu Ser Pro Pro  Leu Glu Val Val Asp  Thr Thr Ala
    2705                2710                2715

Ser Thr  Lys Arg His Leu Arg  Thr Arg Val Gln Lys  Val Gln Val
    2720                2725                2730

Lys Glu  Glu Pro Ser Ala Val  Lys Phe Thr Gln Thr  Ser Gly Glu
    2735                2740                2745

Thr Thr  Asp Ala Asp Lys Glu  Pro Ala Gly Glu Asp  Lys Gly Ile
    2750                2755                2760

Lys Ala  Leu Lys Glu Ser Ala  Lys Gln Thr Pro Ala  Pro Ala Ala
    2765                2770                2775

Ser Val  Thr Gly Ser Arg Arg  Arg Pro Arg Ala Pro  Arg Glu Ser
    2780                2785                2790

Ala Gln  Ala Ile Glu Asp Leu  Ala Gly Phe Lys Asp  Pro Ala Ala
    2795                2800                2805

Gly His  Thr Glu Glu Ser Met  Thr Asp Asp Lys Thr  Thr Lys Ile
    2810                2815                2820

Pro Cys  Lys Ser Ser Pro Glu  Leu Glu Asp Thr Ala  Thr Ser Ser
    2825                2830                2835

Lys Arg  Arg Pro Arg Thr Arg  Ala Gln Lys Val Glu  Val Lys Glu
    2840                2845                2850

Glu Leu  Leu Ala Val Gly Lys  Leu Thr Gln Thr Ser  Gly Glu Thr
    2855                2860                2865

Thr His  Thr Asp Lys Glu Pro  Val Gly Glu Gly Lys  Gly Thr Lys
    2870                2875                2880
```

Ala Phe Lys Gln Pro Ala Lys Arg Lys Leu Asp Ala Glu Asp Val
2885 2890 2895

Ile Gly Ser Arg Arg Gln Pro Arg Ala Pro Lys Glu Lys Ala Gln
2900 2905 2910

Pro Leu Glu Asp Leu Ala Ser Phe Gln Glu Leu Ser Gln Thr Pro
2915 2920 2925

Gly His Thr Glu Glu Leu Ala Asn Gly Ala Ala Asp Ser Phe Thr
2930 2935 2940

Ser Ala Pro Lys Gln Thr Pro Asp Ser Gly Lys Pro Leu Lys Ile
2945 2950 2955

Ser Arg Arg Val Leu Arg Ala Pro Lys Val Glu Pro Val Gly Asp
2960 2965 2970

Val Val Ser Thr Arg Asp Pro Val Lys Ser Gln Ser Lys Ser Asn
2975 2980 2985

Thr Ser Leu Pro Pro Leu Pro Phe Lys Arg Gly Gly Gly Lys Asp
2990 2995 3000

Gly Ser Val Thr Gly Thr Lys Arg Leu Arg Cys Met Pro Ala Pro
3005 3010 3015

Glu Glu Ile Val Glu Glu Leu Pro Ala Ser Lys Lys Gln Arg Val
3020 3025 3030

Ala Pro Arg Ala Arg Gly Lys Ser Ser Glu Pro Val Val Ile Met
3035 3040 3045

Lys Arg Ser Leu Arg Thr Ser Ala Lys Arg Ile Glu Pro Ala Glu
3050 3055 3060

Glu Leu Asn Ser Asn Asp Met Lys Thr Asn Lys Glu Glu His Lys
3065 3070 3075

Leu Gln Asp Ser Val Pro Glu Asn Lys Gly Ile Ser Leu Arg Ser
3080 3085 3090

Arg Arg Gln Asn Lys Thr Glu Ala Glu Gln Gln Ile Thr Glu Val
3095 3100 3105

Phe Val Leu Ala Glu Arg Ile Glu Ile Asn Arg Asn Glu Lys Lys
3110 3115 3120

Pro Met Lys Thr Ser Pro Glu Met Asp Ile Gln Asn Pro Asp Asp
3125 3130 3135

Gly Ala Arg Lys Pro Ile Pro Arg Asp Lys Val Thr Glu Asn Lys
3140 3145 3150

Arg Cys Leu Arg Ser Ala Arg Gln Asn Glu Ser Ser Gln Pro Lys
3155 3160 3165

Val Ala Glu Glu Ser Gly Gly Gln Lys Ser Ala Lys Val Leu Met
3170 3175 3180

Gln Asn Gln Lys Gly Lys Gly Glu Ala Gly Asn Ser Asp Ser Met
3185 3190 3195

Cys Leu Arg Ser Arg Lys Thr Lys Ser Gln Pro Ala Ala Ser Thr
3200 3205 3210

Leu Glu Ser Lys Ser Val Gln Arg Val Thr Arg Ser Val Lys Arg
3215 3220 3225

Cys Ala Glu Asn Pro Lys Lys Ala Glu Asp Asn Val Cys Val Lys
3230 3235 3240

Lys Ile Arg Thr Arg Ser His Arg Asp Ser Glu Asp Ile
3245 3250 3255

<210> SEQ ID NO 34
<211> LENGTH: 403
<212> TYPE: PRT
<213> ORGANISM: Homo sapiens

<400> SEQUENCE: 34

Met Asp Arg Ser Lys Glu Asn Cys Ile Ser Gly Pro Val Lys Ala Thr
1 5 10 15

Ala Pro Val Gly Gly Pro Lys Arg Val Leu Val Thr Gln Gln Phe Pro
20 25 30

Cys Gln Asn Pro Leu Pro Val Asn Ser Gly Gln Ala Gln Arg Val Leu
35 40 45

Cys Pro Ser Asn Ser Ser Gln Arg Ile Pro Leu Gln Ala Gln Lys Leu
50 55 60

Val Ser Ser His Lys Pro Val Gln Asn Gln Lys Gln Lys Gln Leu Gln
65 70 75 80

Ala Thr Ser Val Pro His Pro Val Ser Arg Pro Leu Asn Asn Thr Gln
85 90 95

Lys Ser Lys Gln Pro Leu Pro Ser Ala Pro Glu Asn Asn Pro Glu Glu
100 105 110

Glu Leu Ala Ser Lys Gln Lys Asn Glu Glu Ser Lys Lys Arg Gln Trp
115 120 125

Ala Leu Glu Asp Phe Glu Ile Gly Arg Pro Leu Gly Lys Gly Lys Phe
130 135 140

Gly Asn Val Tyr Leu Ala Arg Glu Lys Gln Ser Lys Phe Ile Leu Ala
145 150 155 160

Leu Lys Val Leu Phe Lys Ala Gln Leu Glu Lys Ala Gly Val Glu His
165 170 175

Gln Leu Arg Arg Glu Val Glu Ile Gln Ser His Leu Arg His Pro Asn
180 185 190

Ile Leu Arg Leu Tyr Gly Tyr Phe His Asp Ala Thr Arg Val Tyr Leu
195 200 205

Ile Leu Glu Tyr Ala Pro Leu Gly Thr Val Tyr Arg Glu Leu Gln Lys
210 215 220

Leu Ser Lys Phe Asp Glu Gln Arg Thr Ala Thr Tyr Ile Thr Glu Leu
225 230 235 240

Ala Asn Ala Leu Ser Tyr Cys His Ser Lys Arg Val Ile His Arg Asp
245 250 255

Ile Lys Pro Glu Asn Leu Leu Leu Gly Ser Ala Gly Glu Leu Lys Ile
260 265 270

Ala Asp Phe Gly Trp Ser Val His Ala Pro Ser Ser Arg Arg Thr Thr
275 280 285

Leu Cys Gly Thr Leu Asp Tyr Leu Pro Pro Glu Met Ile Glu Gly Arg
290 295 300

Met His Asp Glu Lys Val Asp Leu Trp Ser Leu Gly Val Leu Cys Tyr
305 310 315 320

Glu Phe Leu Val Gly Lys Pro Pro Phe Glu Ala Asn Thr Tyr Gln Glu
325 330 335

Thr Tyr Lys Arg Ile Ser Arg Val Glu Phe Thr Phe Pro Asp Phe Val
340 345 350

Thr Glu Gly Ala Arg Asp Leu Ile Ser Arg Leu Leu Lys His Asn Pro
355 360 365

Ser Gln Arg Pro Met Leu Arg Glu Val Leu Glu His Pro Trp Ile Thr
370 375 380

Ala Asn Ser Ser Lys Pro Ser Asn Cys Gln Asn Lys Glu Ser Ala Ser
385 390 395 400

Lys Gln Ser

<210> SEQ ID NO 35
<211> LENGTH: 480
<212> TYPE: PRT
<213> ORGANISM: Homo sapiens

<400> SEQUENCE: 35

```
Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380
```

Lys Lys Asp Pro Lys Gln Arg Leu Gly Gly Gly Ser Glu Asp Ala Lys
385 390 395 400

Glu Ile Met Gln His Arg Phe Phe Ala Gly Ile Val Trp Gln His Val
405 410 415

Tyr Glu Lys Lys Leu Ser Pro Pro Phe Lys Pro Gln Val Thr Ser Glu
420 425 430

Thr Asp Thr Arg Tyr Phe Asp Glu Glu Phe Thr Ala Gln Met Ile Thr
435 440 445

Ile Thr Pro Pro Asp Gln Asp Asp Ser Met Glu Cys Val Asp Ser Glu
450 455 460

Arg Arg Pro His Phe Pro Gln Phe Ser Tyr Ser Ala Ser Gly Thr Ala
465 470 475 480

<210> SEQ ID NO 36
<211> LENGTH: 354
<212> TYPE: PRT
<213> ORGANISM: Homo sapiens

<400> SEQUENCE: 36

Met Arg Leu Ala Val Leu Phe Ser Gly Ala Leu Leu Gly Leu Leu Ala
1 5 10 15

Ala Gln Gly Thr Gly Asn Asp Cys Pro His Lys Lys Ser Ala Thr Leu
20 25 30

Leu Pro Ser Phe Thr Val Thr Pro Thr Val Thr Glu Ser Thr Gly Thr
35 40 45

Thr Ser His Arg Thr Thr Lys Ser His Lys Thr Thr Thr His Arg Thr
50 55 60

Thr Thr Thr Gly Thr Thr Ser His Gly Pro Thr Thr Ala Thr His Asn
65 70 75 80

Pro Thr Thr Thr Ser His Gly Asn Val Thr Val His Pro Thr Ser Asn
85 90 95

Ser Thr Ala Thr Ser Gln Gly Pro Ser Thr Ala Thr His Ser Pro Ala
100 105 110

Thr Thr Ser His Gly Asn Ala Thr Val His Pro Thr Ser Asn Ser Thr
115 120 125

Ala Thr Ser Pro Gly Phe Thr Ser Ser Ala His Pro Glu Pro Pro Pro
130 135 140

Pro Ser Pro Ser Pro Ser Pro Thr Ser Lys Glu Thr Ile Gly Asp Tyr
145 150 155 160

Thr Trp Thr Asn Gly Ser Gln Pro Cys Val His Leu Gln Ala Gln Ile
165 170 175

Gln Ile Arg Val Met Tyr Thr Thr Gln Gly Gly Gly Glu Ala Trp Gly
180 185 190

Ile Ser Val Leu Asn Pro Asn Lys Thr Lys Val Gln Gly Ser Cys Glu
195 200 205

Gly Ala His Pro His Leu Leu Leu Ser Phe Pro Tyr Gly His Leu Ser
210 215 220

Phe Gly Phe Met Gln Asp Leu Gln Gln Lys Val Val Tyr Leu Ser Tyr
225 230 235 240

Met Ala Val Glu Tyr Asn Val Ser Phe Pro His Ala Ala Gln Trp Thr
245 250 255

Phe Ser Ala Gln Asn Ala Ser Leu Arg Asp Leu Gln Ala Pro Leu Gly
260 265 270

Gln Ser Phe Ser Cys Ser Asn Ser Ser Ile Ile Leu Ser Pro Ala Val
275 280 285

-continued

```
His Leu Asp Leu Leu Ser Leu Arg Leu Gln Ala Ala Gln Leu Pro His
    290                 295                 300

Thr Gly Val Phe Gly Gln Ser Phe Ser Cys Pro Ser Asp Arg Ser Ile
305                 310                 315                 320

Leu Leu Pro Leu Ile Ile Gly Leu Ile Leu Leu Gly Leu Leu Ala Leu
                325                 330                 335

Val Leu Ile Ala Phe Cys Ile Ile Arg Arg Arg Pro Ser Ala Tyr Gln
            340                 345                 350

Ala Leu


<210> SEQ ID NO 37
<211> LENGTH: 345
<212> TYPE: PRT
<213> ORGANISM: Homo sapiens

<400> SEQUENCE: 37

Met Ala Gln Arg Gly Gly Ala Arg Arg Pro Arg Gly Asp Arg Glu Arg
1               5                   10                  15

Leu Gly Ser Arg Leu Arg Ala Leu Arg Pro Gly Arg Glu Pro Arg Gln
            20                  25                  30

Ser Glu Pro Pro Ala Gln Arg Gly Pro Pro Pro Ser Gly Arg Pro Pro
        35                  40                  45

Ala Arg Ser Thr Ala Ser Gly His Asp Arg Pro Thr Arg Gly Ala Ala
    50                  55                  60

Ala Gly Ala Arg Arg Pro Arg Met Lys Lys Lys Thr Arg Arg Arg Ser
65                  70                  75                  80

Thr Arg Ser Glu Glu Leu Thr Arg Ser Glu Glu Leu Thr Leu Ser Glu
                85                  90                  95

Glu Ala Thr Trp Ser Glu Glu Ala Thr Gln Ser Glu Glu Ala Thr Gln
            100                 105                 110

Gly Glu Glu Met Asn Arg Ser Gln Glu Val Thr Arg Asp Glu Glu Ser
        115                 120                 125

Thr Arg Ser Glu Glu Val Thr Arg Glu Glu Met Ala Ala Ala Gly Leu
    130                 135                 140

Thr Val Thr Val Thr His Ser Asn Glu Lys His Asp Leu His Val Thr
145                 150                 155                 160

Ser Gln Gln Gly Ser Ser Glu Pro Val Val Gln Asp Leu Ala Gln Val
                165                 170                 175

Val Glu Glu Val Ile Gly Val Pro Gln Ser Phe Gln Lys Leu Ile Phe
            180                 185                 190

Lys Gly Lys Ser Leu Lys Glu Met Glu Thr Pro Leu Ser Ala Leu Gly
        195                 200                 205

Ile Gln Asp Gly Cys Arg Val Met Leu Ile Gly Lys Lys Asn Ser Pro
    210                 215                 220

Gln Glu Glu Val Glu Leu Lys Lys Leu Lys His Leu Glu Lys Ser Val
225                 230                 235                 240

Glu Lys Ile Ala Asp Gln Leu Glu Glu Leu Asn Lys Glu Leu Thr Gly
                245                 250                 255

Ile Gln Gln Gly Phe Leu Pro Lys Asp Leu Gln Ala Glu Ala Leu Cys
            260                 265                 270

Lys Leu Asp Arg Arg Val Lys Ala Thr Ile Glu Gln Phe Met Lys Ile
        275                 280                 285

Leu Glu Glu Ile Asp Thr Leu Ile Leu Pro Glu Asn Phe Lys Asp Ser
    290                 295                 300

Arg Leu Lys Arg Lys Gly Leu Val Lys Lys Val Gln Ala Phe Leu Ala
```

305 310 315 320

Glu Cys Asp Thr Val Glu Gln Asn Ile Cys Gln Glu Thr Glu Arg Leu
325 330 335

Gln Ser Thr Asn Phe Ala Leu Ala Glu
340 345

<210> SEQ ID NO 38
<211> LENGTH: 181
<212> TYPE: PRT
<213> ORGANISM: Homo sapiens

<400> SEQUENCE: 38

Met Pro Met Ile Leu Gly Tyr Trp Asp Ile Arg Gly Leu Ala His Ala
1 5 10 15

Ile Arg Leu Leu Leu Glu Tyr Thr Asp Ser Ser Tyr Glu Glu Lys Lys
20 25 30

Tyr Thr Met Gly Asp Ala Pro Asp Tyr Asp Arg Ser Gln Trp Leu Asn
35 40 45

Glu Lys Phe Lys Leu Gly Leu Asp Phe Pro Asn Leu Pro Tyr Leu Ile
50 55 60

Asp Gly Ala His Lys Ile Thr Gln Ser Asn Ala Ile Leu Cys Tyr Ile
65 70 75 80

Ala Arg Lys His Asn Leu Cys Gly Glu Thr Glu Glu Glu Lys Ile Arg
85 90 95

Val Asp Ile Leu Glu Asn Gln Thr Met Asp Asn His Met Gln Leu Gly
100 105 110

Met Ile Cys Tyr Asn Pro Glu Phe Glu Lys Leu Lys Pro Lys Tyr Leu
115 120 125

Glu Glu Leu Pro Glu Lys Leu Lys Leu Tyr Ser Glu Phe Leu Gly Lys
130 135 140

Arg Pro Trp Phe Ala Gly Asn Lys Gly Leu Glu Lys Ile Ser Ala Tyr
145 150 155 160

Met Lys Ser Ser Arg Phe Leu Pro Arg Pro Val Phe Ser Lys Met Ala
165 170 175

Val Trp Gly Asn Lys
180

<210> SEQ ID NO 39
<211> LENGTH: 375
<212> TYPE: PRT
<213> ORGANISM: Homo sapiens

<400> SEQUENCE: 39

Met Asp Asp Asp Ile Ala Ala Leu Val Val Asp Asn Gly Ser Gly Met
1 5 10 15

Cys Lys Ala Gly Phe Ala Gly Asp Asp Ala Pro Arg Ala Val Phe Pro
20 25 30

Ser Ile Val Gly Arg Pro Arg His Gln Gly Val Met Val Gly Met Gly
35 40 45

Gln Lys Asp Ser Tyr Val Gly Asp Glu Ala Gln Ser Lys Arg Gly Ile
50 55 60

Leu Thr Leu Lys Tyr Pro Ile Glu His Gly Ile Val Thr Asn Trp Asp
65 70 75 80

Asp Met Glu Lys Ile Trp His His Thr Phe Tyr Asn Glu Leu Arg Val
85 90 95

Ala Pro Glu Glu His Pro Val Leu Leu Thr Glu Ala Pro Leu Asn Pro
100 105 110

```
Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Ala Thr Ala Ala Ser Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
    290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365

Ile Val His Arg Lys Cys Phe
    370                 375
```

<210> SEQ ID NO 40
<211> LENGTH: 335
<212> TYPE: PRT
<213> ORGANISM: Homo sapiens

<400> SEQUENCE: 40

```
Met Gly Lys Val Lys Val Gly Val Asn Gly Phe Gly Arg Ile Gly Arg
1               5                   10                  15

Leu Val Thr Arg Ala Ala Phe Asn Ser Gly Lys Val Asp Ile Val Ala
            20                  25                  30

Ile Asn Asp Pro Phe Ile Asp Leu Asn Tyr Met Val Tyr Met Phe Gln
        35                  40                  45

Tyr Asp Ser Thr His Gly Lys Phe His Gly Thr Val Lys Ala Glu Asn
    50                  55                  60

Gly Lys Leu Val Ile Asn Gly Asn Pro Ile Thr Ile Phe Gln Glu Arg
65                  70                  75                  80

Asp Pro Ser Lys Ile Lys Trp Gly Asp Ala Gly Ala Glu Tyr Val Val
                85                  90                  95

Glu Ser Thr Gly Val Phe Thr Thr Met Glu Lys Ala Gly Ala His Leu
            100                 105                 110
```

Gln Gly Gly Ala Lys Arg Val Ile Ile Ser Ala Pro Ser Ala Asp Ala
115 120 125

Pro Met Phe Val Met Gly Val Asn His Glu Lys Tyr Asp Asn Ser Leu
130 135 140

Lys Ile Ile Ser Asn Ala Ser Cys Thr Thr Asn Cys Leu Ala Pro Leu
145 150 155 160

Ala Lys Val Ile His Asp Asn Phe Gly Ile Val Glu Gly Leu Met Thr
165 170 175

Thr Val His Ala Ile Thr Ala Thr Gln Lys Thr Val Asp Gly Pro Ser
180 185 190

Gly Lys Leu Trp Arg Asp Gly Arg Gly Ala Leu Gln Asn Ile Ile Pro
195 200 205

Ala Ser Thr Gly Ala Ala Lys Ala Val Gly Lys Val Ile Pro Glu Leu
210 215 220

Asn Gly Lys Leu Thr Gly Met Ala Phe Arg Val Pro Thr Ala Asn Val
225 230 235 240

Ser Val Val Asp Leu Thr Cys Arg Leu Glu Lys Pro Ala Lys Tyr Asp
245 250 255

Asp Ile Lys Lys Val Val Lys Gln Ala Ser Glu Gly Pro Leu Lys Gly
260 265 270

Ile Leu Gly Tyr Thr Glu His Gln Val Val Ser Ser Asp Phe Asn Ser
275 280 285

Asp Thr His Ser Ser Thr Phe Asp Ala Gly Ala Gly Ile Ala Leu Asn
290 295 300

Asp His Phe Val Lys Leu Ile Ser Trp Tyr Asp Asn Glu Phe Gly Tyr
305 310 315 320

Ser Asn Arg Val Val Asp Leu Met Ala His Met Ala Ser Lys Glu
325 330 335

<210> SEQ ID NO 41
<211> LENGTH: 651
<212> TYPE: PRT
<213> ORGANISM: Homo sapiens

<400> SEQUENCE: 41

Met Ala Arg Gly Ser Ala Val Ala Trp Ala Ala Leu Gly Pro Leu Leu
1 5 10 15

Trp Gly Cys Ala Leu Gly Leu Gln Gly Gly Met Leu Tyr Pro Gln Glu
20 25 30

Ser Pro Ser Arg Glu Cys Lys Glu Leu Asp Gly Leu Trp Ser Phe Arg
35 40 45

Ala Asp Phe Ser Asp Asn Arg Arg Arg Gly Phe Glu Glu Gln Trp Tyr
50 55 60

Arg Arg Pro Leu Trp Glu Ser Gly Pro Thr Val Asp Met Pro Val Pro
65 70 75 80

Ser Ser Phe Asn Asp Ile Ser Gln Asp Trp Arg Leu Arg His Phe Val
85 90 95

Gly Trp Val Trp Tyr Glu Arg Glu Val Ile Leu Pro Glu Arg Trp Thr
100 105 110

Gln Asp Leu Arg Thr Arg Val Val Leu Arg Ile Gly Ser Ala His Ser
115 120 125

Tyr Ala Ile Val Trp Val Asn Gly Val Asp Thr Leu Glu His Glu Gly
130 135 140

Gly Tyr Leu Pro Phe Glu Ala Asp Ile Ser Asn Leu Val Gln Val Gly
145 150 155 160

```
Pro Leu Pro Ser Arg Leu Arg Ile Thr Ile Ala Ile Asn Asn Thr Leu
                165                 170                 175

Thr Pro Thr Thr Leu Pro Pro Gly Thr Ile Gln Tyr Leu Thr Asp Thr
            180                 185                 190

Ser Lys Tyr Pro Lys Gly Tyr Phe Val Gln Asn Thr Tyr Phe Asp Phe
        195                 200                 205

Phe Asn Tyr Ala Gly Leu Gln Arg Ser Val Leu Leu Tyr Thr Thr Pro
    210                 215                 220

Thr Thr Tyr Ile Asp Asp Ile Thr Val Thr Thr Ser Val Glu Gln Asp
225                 230                 235                 240

Ser Gly Leu Val Asn Tyr Gln Ile Ser Val Lys Gly Ser Asn Leu Phe
                245                 250                 255

Lys Leu Glu Val Arg Leu Leu Asp Ala Glu Asn Lys Val Val Ala Asn
            260                 265                 270

Gly Thr Gly Thr Gln Gly Gln Leu Lys Val Pro Gly Val Ser Leu Trp
        275                 280                 285

Trp Pro Tyr Leu Met His Glu Arg Pro Ala Tyr Leu Tyr Ser Leu Glu
    290                 295                 300

Val Gln Leu Thr Ala Gln Thr Ser Leu Gly Pro Val Ser Asp Phe Tyr
305                 310                 315                 320

Thr Leu Pro Val Gly Ile Arg Thr Val Ala Val Thr Lys Ser Gln Phe
                325                 330                 335

Leu Ile Asn Gly Lys Pro Phe Tyr Phe His Gly Val Asn Lys His Glu
            340                 345                 350

Asp Ala Asp Ile Arg Gly Lys Gly Phe Asp Trp Pro Leu Leu Val Lys
        355                 360                 365

Asp Phe Asn Leu Leu Arg Trp Leu Gly Ala Asn Ala Phe Arg Thr Ser
    370                 375                 380

His Tyr Pro Tyr Ala Glu Glu Val Met Gln Met Cys Asp Arg Tyr Gly
385                 390                 395                 400

Ile Val Val Ile Asp Glu Cys Pro Gly Val Gly Leu Ala Leu Pro Gln
                405                 410                 415

Phe Phe Asn Asn Val Ser Leu His His His Met Gln Val Met Glu Glu
            420                 425                 430

Val Val Arg Arg Asp Lys Asn His Pro Ala Val Val Met Trp Ser Val
        435                 440                 445

Ala Asn Glu Pro Ala Ser His Leu Glu Ser Ala Gly Tyr Tyr Leu Lys
    450                 455                 460

Met Val Ile Ala His Thr Lys Ser Leu Asp Pro Ser Arg Pro Val Thr
465                 470                 475                 480

Phe Val Ser Asn Ser Asn Tyr Ala Ala Asp Lys Gly Ala Pro Tyr Val
                485                 490                 495

Asp Val Ile Cys Leu Asn Ser Tyr Tyr Ser Trp Tyr His Asp Tyr Gly
            500                 505                 510

His Leu Glu Leu Ile Gln Leu Gln Leu Ala Thr Gln Phe Glu Asn Trp
        515                 520                 525

Tyr Lys Lys Tyr Gln Lys Pro Ile Ile Gln Ser Glu Tyr Gly Ala Glu
    530                 535                 540

Thr Ile Ala Gly Phe His Gln Asp Pro Pro Leu Met Phe Thr Glu Glu
545                 550                 555                 560

Tyr Gln Lys Ser Leu Leu Glu Gln Tyr His Leu Gly Leu Asp Gln Lys
                565                 570                 575

Arg Arg Lys Tyr Val Val Gly Glu Leu Ile Trp Asn Phe Ala Asp Phe
```

```
            580                 585                 590

Met Thr Glu Gln Ser Pro Thr Arg Val Leu Gly Asn Lys Lys Gly Ile
        595                 600                 605

Phe Thr Arg Gln Arg Gln Pro Lys Ser Ala Ala Phe Leu Leu Arg Glu
    610                 615                 620

Arg Tyr Trp Lys Ile Ala Asn Glu Thr Arg Tyr Pro His Ser Val Ala
625                 630                 635                 640

Lys Ser Gln Cys Leu Glu Asn Ser Pro Phe Thr
                645                 650


<210> SEQ ID NO 42
<211> LENGTH: 317
<212> TYPE: PRT
<213> ORGANISM: Homo sapiens

<400> SEQUENCE: 42

Met Pro Arg Glu Asp Arg Ala Thr Trp Lys Ser Asn Tyr Phe Leu Lys
1               5                   10                  15

Ile Ile Gln Leu Leu Asp Asp Tyr Pro Lys Cys Phe Ile Val Gly Ala
            20                  25                  30

Asp Asn Val Gly Ser Lys Gln Met Gln Gln Ile Arg Met Ser Leu Arg
        35                  40                  45

Gly Lys Ala Val Val Leu Met Gly Lys Asn Thr Met Met Arg Lys Ala
    50                  55                  60

Ile Arg Gly His Leu Glu Asn Asn Pro Ala Leu Glu Lys Leu Leu Pro
65                  70                  75                  80

His Ile Arg Gly Asn Val Gly Phe Val Phe Thr Lys Glu Asp Leu Thr
                85                  90                  95

Glu Ile Arg Asp Met Leu Leu Ala Asn Lys Val Pro Ala Ala Ala Arg
            100                 105                 110

Ala Gly Ala Ile Ala Pro Cys Glu Val Thr Val Pro Ala Gln Asn Thr
        115                 120                 125

Gly Leu Gly Pro Glu Lys Thr Ser Phe Phe Gln Ala Leu Gly Ile Thr
    130                 135                 140

Thr Lys Ile Ser Arg Gly Thr Ile Glu Ile Leu Ser Asp Val Gln Leu
145                 150                 155                 160

Ile Lys Thr Gly Asp Lys Val Gly Ala Ser Glu Ala Thr Leu Leu Asn
                165                 170                 175

Met Leu Asn Ile Ser Pro Phe Ser Phe Gly Leu Val Ile Gln Gln Val
            180                 185                 190

Phe Asp Asn Gly Ser Ile Tyr Asn Pro Glu Val Leu Asp Ile Thr Glu
        195                 200                 205

Glu Thr Leu His Ser Arg Phe Leu Glu Gly Val Arg Asn Val Ala Ser
    210                 215                 220

Val Cys Leu Gln Ile Gly Tyr Pro Thr Val Ala Ser Val Pro His Ser
225                 230                 235                 240

Ile Ile Asn Gly Tyr Lys Arg Val Leu Ala Leu Ser Val Glu Thr Asp
                245                 250                 255

Tyr Thr Phe Pro Leu Ala Glu Lys Val Lys Ala Phe Leu Ala Asp Pro
            260                 265                 270

Ser Ala Phe Val Ala Ala Ala Pro Val Ala Ala Ala Thr Thr Ala Ala
        275                 280                 285

Pro Ala Ala Ala Ala Ala Pro Ala Lys Val Glu Ala Lys Glu Glu Ser
    290                 295                 300

Glu Glu Ser Asp Glu Asp Met Gly Phe Gly Leu Phe Asp
```

305 310 315

<210> SEQ ID NO 43
<211> LENGTH: 760
<212> TYPE: PRT
<213> ORGANISM: Homo sapiens

<400> SEQUENCE: 43

Met Met Asp Gln Ala Arg Ser Ala Phe Ser Asn Leu Phe Gly Gly Glu
1 5 10 15

Pro Leu Ser Tyr Thr Arg Phe Ser Leu Ala Arg Gln Val Asp Gly Asp
20 25 30

Asn Ser His Val Glu Met Lys Leu Ala Val Asp Glu Glu Glu Asn Ala
35 40 45

Asp Asn Asn Thr Lys Ala Asn Val Thr Lys Pro Lys Arg Cys Ser Gly
50 55 60

Ser Ile Cys Tyr Gly Thr Ile Ala Val Ile Val Phe Phe Leu Ile Gly
65 70 75 80

Phe Met Ile Gly Tyr Leu Gly Tyr Cys Lys Gly Val Glu Pro Lys Thr
85 90 95

Glu Cys Glu Arg Leu Ala Gly Thr Glu Ser Pro Val Arg Glu Glu Pro
100 105 110

Gly Glu Asp Phe Pro Ala Ala Arg Arg Leu Tyr Trp Asp Asp Leu Lys
115 120 125

Arg Lys Leu Ser Glu Lys Leu Asp Ser Thr Asp Phe Thr Ser Thr Ile
130 135 140

Lys Leu Leu Asn Glu Asn Ser Tyr Val Pro Arg Glu Ala Gly Ser Gln
145 150 155 160

Lys Asp Glu Asn Leu Ala Leu Tyr Val Glu Asn Gln Phe Arg Glu Phe
165 170 175

Lys Leu Ser Lys Val Trp Arg Asp Gln His Phe Val Lys Ile Gln Val
180 185 190

Lys Asp Ser Ala Gln Asn Ser Val Ile Ile Val Asp Lys Asn Gly Arg
195 200 205

Leu Val Tyr Leu Val Glu Asn Pro Gly Gly Tyr Val Ala Tyr Ser Lys
210 215 220

Ala Ala Thr Val Thr Gly Lys Leu Val His Ala Asn Phe Gly Thr Lys
225 230 235 240

Lys Asp Phe Glu Asp Leu Tyr Thr Pro Val Asn Gly Ser Ile Val Ile
245 250 255

Val Arg Ala Gly Lys Ile Thr Phe Ala Glu Lys Val Ala Asn Ala Glu
260 265 270

Ser Leu Asn Ala Ile Gly Val Leu Ile Tyr Met Asp Gln Thr Lys Phe
275 280 285

Pro Ile Val Asn Ala Glu Leu Ser Phe Phe Gly His Ala His Leu Gly
290 295 300

Thr Gly Asp Pro Tyr Thr Pro Gly Phe Pro Ser Phe Asn His Thr Gln
305 310 315 320

Phe Pro Pro Ser Arg Ser Ser Gly Leu Pro Asn Ile Pro Val Gln Thr
325 330 335

Ile Ser Arg Ala Ala Ala Glu Lys Leu Phe Gly Asn Met Glu Gly Asp
340 345 350

Cys Pro Ser Asp Trp Lys Thr Asp Ser Thr Cys Arg Met Val Thr Ser
355 360 365

Glu Ser Lys Asn Val Lys Leu Thr Val Ser Asn Val Leu Lys Glu Ile

```
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760
```

<210> SEQ ID NO 44
<211> LENGTH: 114
<212> TYPE: PRT
<213> ORGANISM: Homo sapiens -continued

```
<400> SEQUENCE: 44

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro
```